United States Patent
Christensen

(10) Patent No.: US 8,133,984 B2
(45) Date of Patent: Mar. 13, 2012

(54) OLIGONUCLEOTIDES COMPRISING SIGNALLING PAIRS AND HYDROPHOBIC NUCLEOTIDES, STEMLESS BEACONS, FOR DETECTION OF NUCLEIC ACIDS, METHYLATION STATUS AND MUTANTS OF NUCLEIC ACIDS

(75) Inventor: Ulf Bech Christensen, Soendersoe (DK)

(73) Assignee: PENTABASE ApS, Soendersoe (DK)

( * ) Notice: Subject to any disclaimer, the term of this patent is extended or adjusted under 35 U.S.C. 154(b) by 514 days.

(21) Appl. No.: 12/293,201

(22) PCT Filed: Mar. 16, 2007

(86) PCT No.: PCT/DK2007/000134
§ 371 (c)(1),
(2), (4) Date: Sep. 16, 2008

(87) PCT Pub. No.: WO2007/104318
PCT Pub. Date: Sep. 20, 2007

(65) Prior Publication Data
US 2010/0068704 A1    Mar. 18, 2010

(30) Foreign Application Priority Data
Mar. 16, 2006   (DK) .................................. 2006 00379

(51) Int. Cl.
*C07H 21/02* (2006.01)
*C12Q 1/68* (2006.01)
*C12P 19/34* (2006.01)
(52) U.S. Cl. ..................... 536/23.1; 536/24.3; 435/6.11; 435/6.12; 435/91.2
(58) Field of Classification Search .......... None
See application file for complete search history.

(56) References Cited

U.S. PATENT DOCUMENTS

| | | | |
|---|---|---|---|
| 5,466,578 A | 11/1995 | Kidwell | |
| 5,925,517 A | 7/1999 | Tyagi et al. | |
| 6,037,130 A | 3/2000 | Tyagi et al. | |
| 6,103,476 A | 8/2000 | Tyagi et al. | |
| 6,150,097 A | 11/2000 | Tyagi et al. | |
| 6,355,421 B1 | 3/2002 | Coull et al. | |
| 2002/0064772 A1 | 5/2002 | Gildea et al. | |

(Continued)

FOREIGN PATENT DOCUMENTS

EP    1484337 A2    12/2004

(Continued)

OTHER PUBLICATIONS

International Search Report for PCT/DK2007/000134.

(Continued)

*Primary Examiner* — Samuel Woolwine
(74) *Attorney, Agent, or Firm* — Brooks Kushman P.C.

(57) ABSTRACT

The invention relates to novel oligonucleotides comprising a signalling pair and at least two hydrophobic nucleotides. The oligonucleotide analogues are useful for detecting the status of nucleic acid sequences, such as presence, expression, methylation and/or mutation, in particular single point mutations and other sequences where the variation between the correct target and other targets may vary in as little as one nucleotide. The invention also relates to new ways of detecting sequence differences and optimizing conditions by using oligonucleotide analogues and readily available instruments. In particular the invention relates to specifically detecting quantity of a target nucleic acids or detecting one sequence over others that may vary in as little as one nucleotide using oligonucleotides or oligonucleotide analogues comprising a signalling pair and at least two hydrophobic nucleotides, such as a nucleotide analogue comprising an intercalator.

14 Claims, 14 Drawing Sheets

U.S. PATENT DOCUMENTS

| | | | |
|---|---|---|---|
| 2005/0064463 A1 | 3/2005 | Hedgpeth et al. | |
| 2005/0158720 A1 | 7/2005 | Li et al. | |
| 2005/0227247 A1 | 10/2005 | Maynard | |
| 2005/0227257 A1 | 10/2005 | Abravaya et al. | |
| 2005/0233360 A1 | 10/2005 | Davies et al. | |

FOREIGN PATENT DOCUMENTS

| | | |
|---|---|---|
| JP | 11-332595 A | 12/1999 |
| WO | 99/14226 A2 | 3/1999 |
| WO | 99/21881 A1 | 5/1999 |
| WO | 01/73118 A2 | 10/2001 |
| WO | 03/043402 A2 | 5/2003 |
| WO | 03/051901 A2 | 6/2003 |
| WO | 03/052132 A2 | 6/2003 |
| WO | 03/052134 A2 | 6/2003 |
| WO | 03/072051 A2 | 9/2003 |
| WO | 2004/033726 A1 | 4/2004 |
| WO | 2005/019812 A1 | 3/2005 |

OTHER PUBLICATIONS

Afonina et al., Efficient Priming of PCR With Short Oligonucleotides Conjugated to a Minor Groove Binder, 1997, Nucleic Acids Research, vol. 25, No. 13, pp. 2657-2660.

Arya et al., Basic Principles of Real-Time Quantitative PCR, 2005, Expert Review of Molecular Diagnostics, vol. 5, No. 2, pp. 209-219.

Christensen et al., Intercalating Nucleic Acids: The Influence of Linker Length and Intercalator Type on Their Duplex Stabilities, 2004, Nucleosides, Nucleotides & Nucleic Acids, vol. 23, No. 1 & 2, pp. 207-225.

Filichev et al., Locked Nucleic Acids and Intercalating Nucleic Acids in the Design of Easily Denaturing Nucleic Acids: Thermal Stability Studies, 2004, ChemBioChem, vol. 5, pp. 1673-1679.

Freifelder, Chapter 15: Fluorescence Spectroscopy, Physical Biochemistry: Applications to Biochemistry and Molecular Biology, 1976, pp. 410-443.

Grompe, The Rapid Detection of Unknown Mutations in Nucleic Acids, Oct. 1993, Nature: Genetics, vol. 5, pp. 111-117.

Hunter et al., The Nature of Pi-Pi Interactions, Jul. 1990, Journal of the American Chemical Society, vol. 112, No. 14, pp. 5525-5534.

Kutyavin et al., 3'-Minor Groove Binder-DNA Probes Increase Sequence Specificity at PCR Extension Temperatures, 2000, Nucleic Acids Research, vol. 28, No. 2, pp. 655-661.

Lamture et al., Direct Detection of Nucleic Acid Hybridization on the Surface of a Charge Coupled Device, 1994, Nucleic Acids Research, vol. 22, No. 11, pp. 2121-2125.

Letertre et al., Evaluation of the Performance of LNA and MGB Probes in 5'-Nuclease PCR Assays, 2003, Molecular and Cellular Probes, vol. 17, pp. 307-311.

Moriguchi et al., Simple Method of Calculating Octanol/Water Partition Coefficient, 1992, Chemical & Pharmaceutical Bulletin, vol. 40, No. 1, pp. 127-130.

Poda et al., Towards Predictive ADME Profiling of Drug Candidates: Lipophilicity and Solubility, 2005, 229th ACS National Meeting, San Diego, CA.

Sahu et al., Estimation of Octanol-Water Partition Coefficients for Polycylic Aromatic Hydrocarbons Using Reverse-Phase HPLC, 2003, Journal of Liquid Chromatography & Related Technologies, vol. 26, No. 1, pp. 135-146.

Santalucia, Jr. et al., The Thermodynamics of DNA Structural Motifs, 2004, Annual Review of Biophysics and Biomolecular Structure, vol. 33, pp. 415-440.

Schena et al., Parallel Human Genome Analysis: Microarray-Based Expression Monitoring of 1000 Genes, Oct. 1996, Proc. Natl. Acad. Sci. USA, vol. 93, pp. 10614-10619.

Seitz, Solid-Phase Synthesis of Doubly Labeled Peptide Nucleic Acids as Probes for the Real-Time Detection of Hybridization, Sep. 15, 2000, Angewandte Chemie International Edition, vol. 39, No. 18, pp. 3249-3252.

Sosnowski et al., Rapid Determination of Single Base Mismatch Mutations in DNA Hybrids by Direct Electric Field Control, Feb. 1997, Proc. Natl. Acad. Sci. USA, vol. 94, pp. 1119-1123.

Southern, Detection of Specific Sequences Among DNA Fragments Separated by Gel Electrophoresis, 1975, Journal of Molecular Biology, vol. 98, pp. 503-517.

Tetko et al., Prediction of n-Octanol/Water Partition Coefficients From PHYSPROP Database Using Artificial Neural Networks and E-State Indices, 2001, Journal of Chemical Information and Computer Sciences, vol. 41, pp. 1407-1421.

Tetko et al., Estimation of Aqueous Solubility of Chemical Compounds Using E-State Indices, 2001, Journal of Chemical Information and Computer Sciences, vol. 41, pp. 1488-1493.

Tetko et al., Application of Associative Neural Networks for Prediction of Lipophilicity in ALOGPS 2.1 Program, 2002, Journal of Chemical Information and Computer Sciences, vol. 42, pp. 1136-1145.

Tetko et al., Application of ALOGPS 2.1 to Predict log D Distribution Coefficient for Pfizer Proprietary Compounds, 2004, Journal of Medicinal Chemistry, vol. 47, pp. 5601-5604.

Tetko et al., Application of ALOGPS to Predict 1-Octanol/Water Distribution Coefficients, logP, and logD of AstraZeneca In-House Database, Dec. 2004, Journal of Pharmaceutical Sciences, vol. 93, No. 12, pp. 3103-3110.

Tetko, Computing Chemistry on the Web, 2005, Drug Discovery Today, vol. 10, No. 22, pp. 1497-1500.

Tetko et al., Virtual Computational Chemistry Laboratory—Design and Description, 2005, Journal of Computer-Aided Molecular Design, vol. 19, pp. 453-463.

Tijssen, Practice and Theory of Enzyme Immunoassays, Chapter 2: Outline of the Strategies for Enzyme Immunoassays, 1985, Laboratory Techniques in Biochemistry and Molecular Biology, eds. Burdon & van Knippenberg, pp. 9-20.

Viswanadhan et al., Atomic Physicochemical Parameters for Three Dimensional Structure Directed Quantitative Structure—Activity Relationships. 4. Additional Parameters for Hydrophobic Dispersive Interactions and Their Application for an Automated Superposition of Certain Naturally Occurring Nucleoside Antibiotics, 1989, Journal of Chemical Information and Computer Sciences, vol. 29, pp. 163-172.

Yamana et al., Synthesis and Properties of Oligonucleotides Bearing a Pendant Pyrene Group, 1985, Nucleic Acids Research, Symposium Series No. 16, pp. 169-172.

Yershov et al., DNA Analysis and Diagnostics on Oligonucleotide Microchips, May 1996, Proc. Natl. Acad. Sci. USA, vol. 93, pp. 4913-4918.

Allart et al., D-Altritol Nucleic Acids (ANA): Hybridisation Properties, Stability and Initial Structural Analysis, 1999, Chemistry: A European Journal, vol. 5, No. 8, pp. 2424-2431.

Hossain et al., Oligonucleotides Composed of 2'-Deoxy-1', 5'-anhydro-D-mannitol Nucleosides with a Purine Base Moiety, 1998, Journal of Organic Chemistry, vol. 63, pp. 1574-1582.

Koshkin et al., LNA(Locked Nucleic Acids): Synthesis of the Adenine, Cytosine, Guanine, 5-Methylcytosine, Thymine and Uracil Bicyclonucleoside Monomers, Oligomerisation and Unprecedented Nucleic Acid Recognition, 1998, Tetrahedron, vol. 54, pp. 3607-3630.

Leumann, DNA Analogues: From Supramolecular Principles to Biological Properties, 2002, Bioorganic & Medicinal Chemistry, vol. 10, pp. 841-854.

Maurinsh et al., Synthesis and Pairing Properties of Oligonucleotides Containing 3-Hydroxy-4-hydroxymethyl-1-cyclohexanyl Nucleosides, 1999, Chemistry: A European Journal, vol. 5, No. 7, pp. 2139-2150.

Manoharan, 2'-Carbohydrate Modification in Antisense Oligonucleotide Therapy: Importance of Conformation, Configuration and Conjugation, 1999, Biochimica et Biophysica Acta, vol. 1489, pp. 117-130.

Nielsen et al., Sequence-Selective Recognition of DNA by Strand Displacement with a Thymine-Substituted Polyamide, Dec. 6, 1991, Science, vol. 254, pp. 1497-1500.

Obika et al., Synthesis of 2'-O, 4'-C Methyleneuridine and -cytidine. Novel Bicyclic Nucleosides Having a Fixed C3, -endo Sugar Puckering, 1997, Tetrahedron Letters, vol. 38, No. 50, pp. 8735-8738.

Rajwanshi et al., LNA Stereoisomers: xylo-LNA (b-d-xylo Configured Locked Nucleic Acid) and a-l-LNA (a-l-ribo Configured Locked Nucleic Acid), 1999, Chemical Communications, vol. 15, pp. 1395-1396.

Rajwanshi et al., The Eight Stereoisomers LNA(Locked Nucleic Acid): A Remarkable Family of Strong RNA Binding Molecules, 2000, Angewandte Chemie International Edition, vol. 39, No. 9, pp. 1656-1659.

Reck et al., L-a-Lyxopyranosyl (4'→3') Oligonucleotides: A Base-Pairing System Containing a Shortened Backbone, 1999, Organic Letters, vol. 1, No. 10, pp. 1531-1534.

Sayer et al., Covalent Nucleoside Adducts of Benzo[a]pyrene 7, 8-Diol 9, 10-Epoxides: Structural Reinvestigation and Characterization of a Novel Adenosine Adduct on the Ribose Moiety, 1991, Journal of Organic Chemistry, vol. 56, pp. 20-29.

Singh et al., LNA(Locked Nucleic Acids): Synthesis and High-Affinity Nucleic Acid Recognition, 1998, Chemical Communications, vol. 4, pp. 455-456.

Van Aerschot et al., 1, 5-Anhydrohexitol Nucleic Acids, a New Promising Antisense Construct, 1995, Angewandte Chemie International Edition in English, vol. 34, No. 12, pp. 1338-1339.

Wang et al., Conformationally Locked Nucleosides, Synthesis and Stereochemical Assignments of 2'-C, 4'-C-Bridged Bicyclonucleosides, 1999, Tetrahedron, vol. 55, pp. 7707-7724.

Wang et al., Cyclohexene Nucleic Acids (CeNA): Serum Stable Oligonucleotides That Activate RNase H and Increase Duplex Stability With Complementary RNA, 2000, Journal of the American Chemical Society, vol. 122, pp. 8595-8602.

Wu et al., Base-Pairing Systems Related to TNA: a-Threofuranosyl Oligonucleotides Containing Phosphoramidate Linkages, 2002, Organic Letters, vol. 4, No. 8, pp. 1279-1282.

Fig. 1
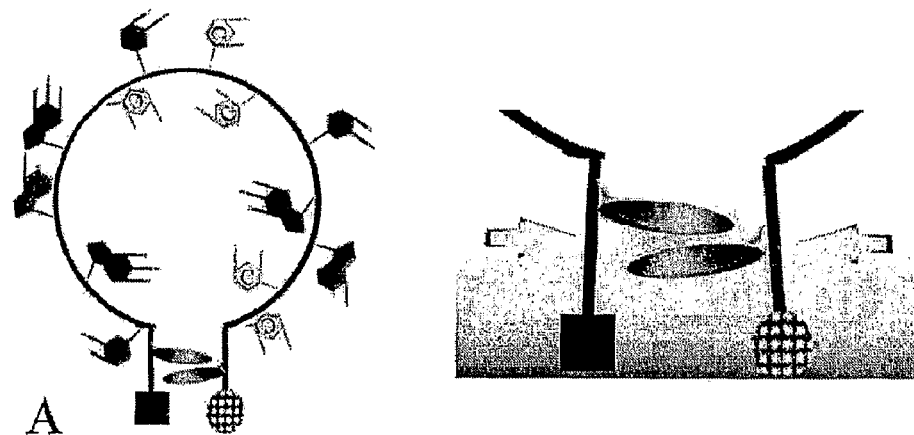
A
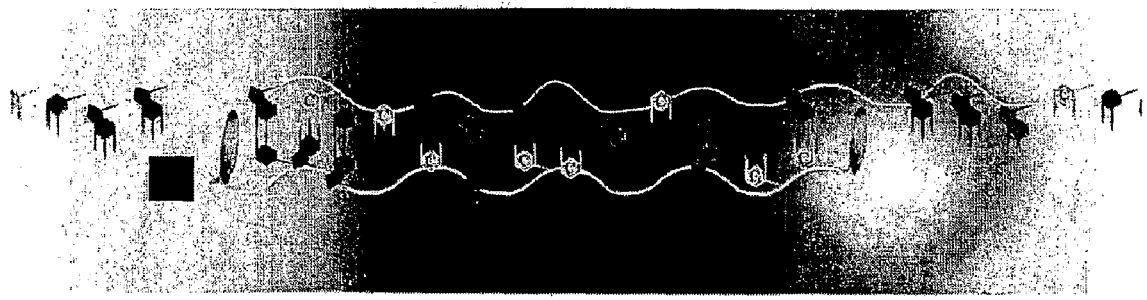
B
C

Fig. 4
A
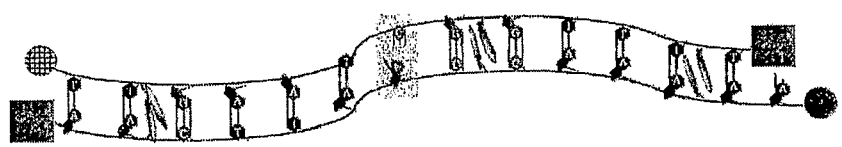
B
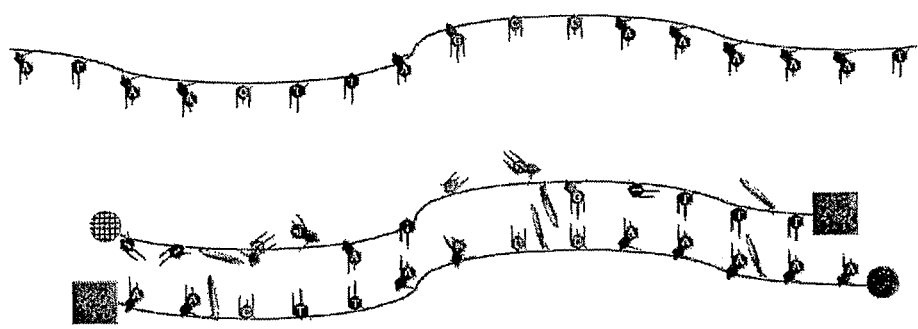
C
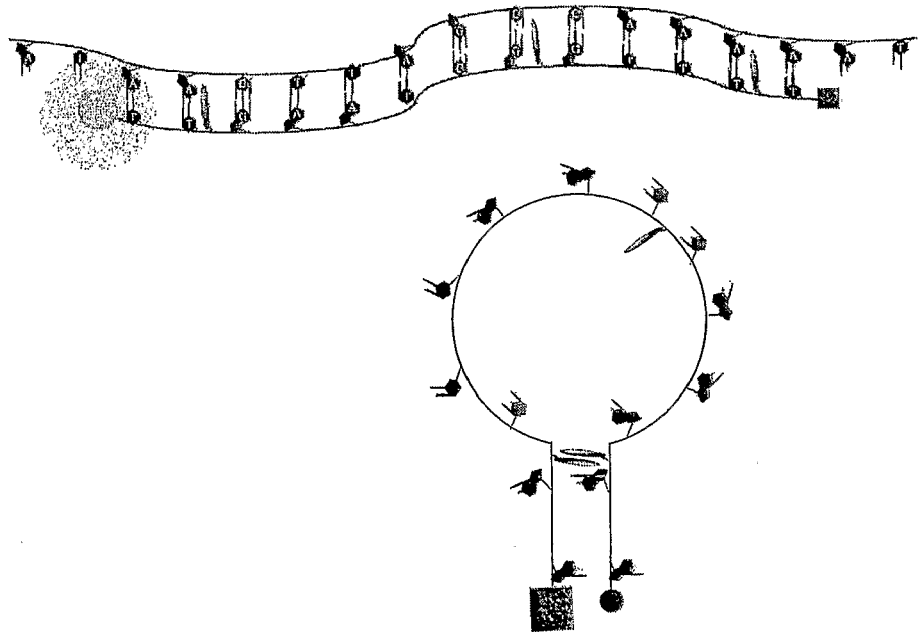

Fig. 5
A
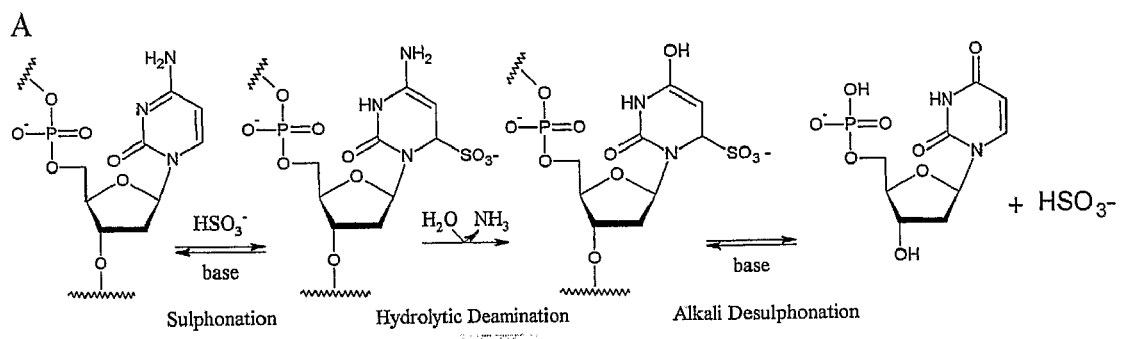
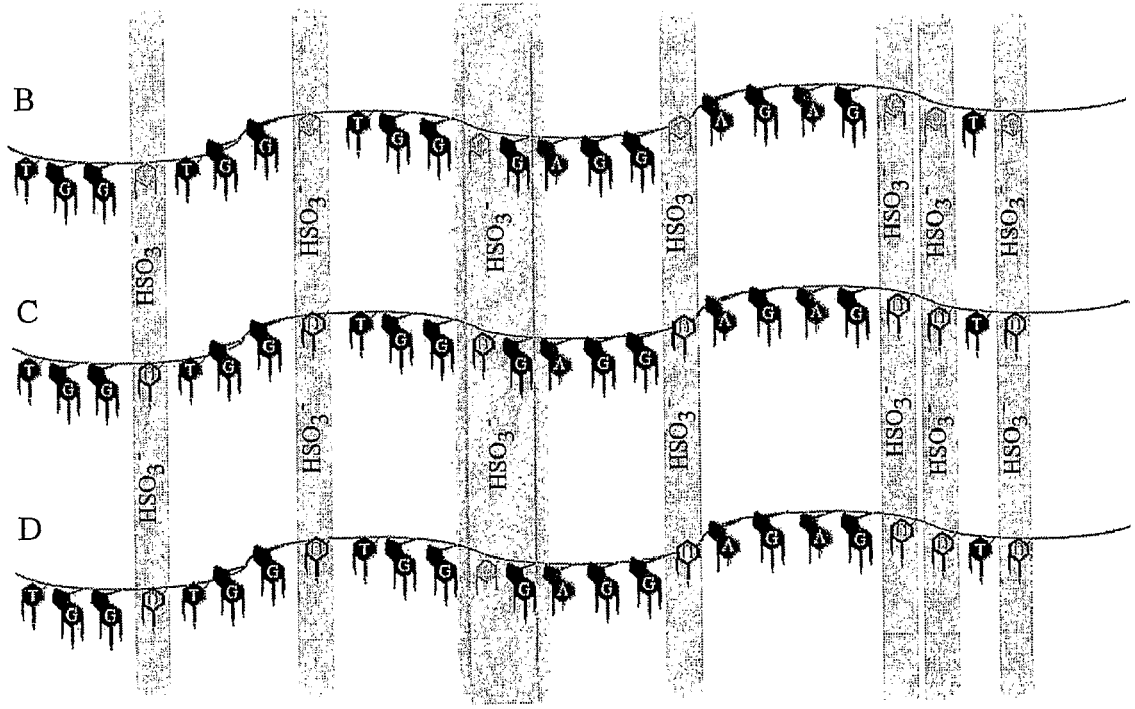

Fig. 8
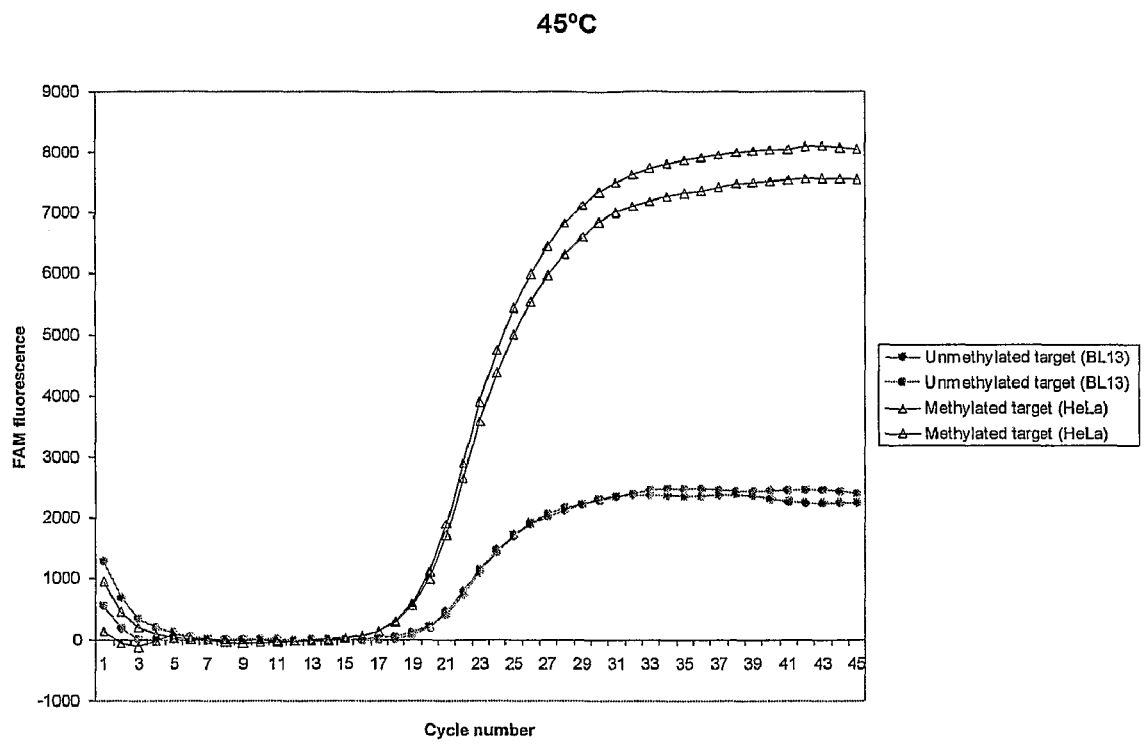
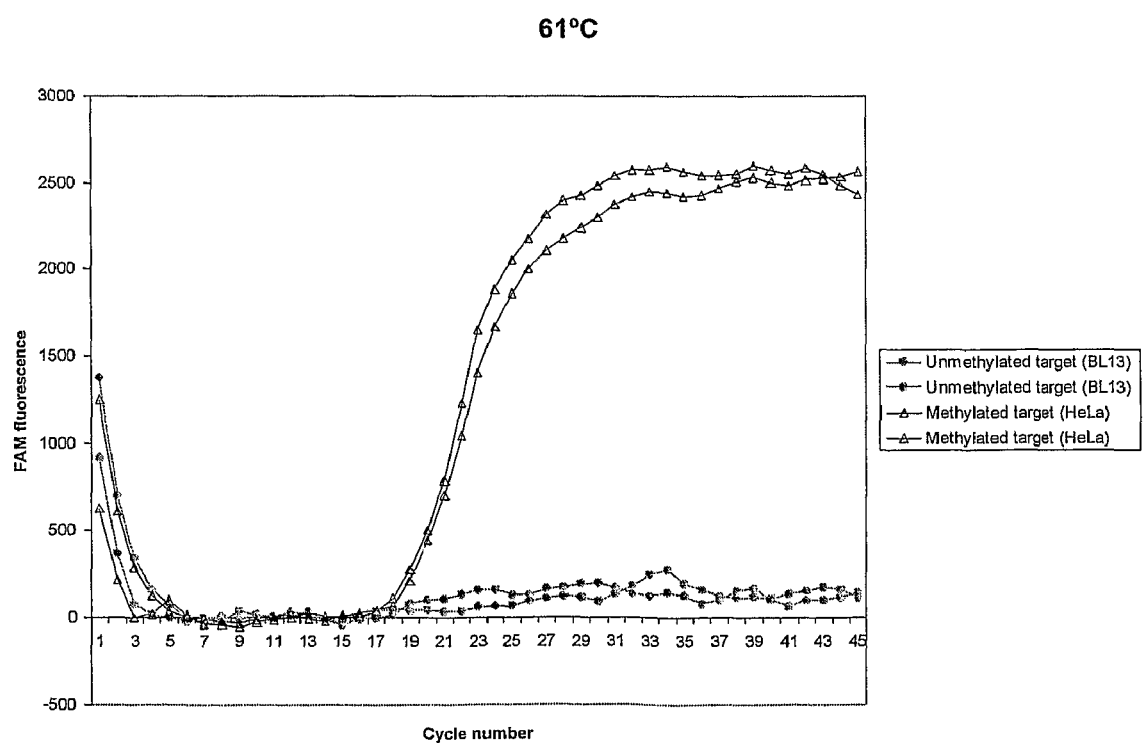

Fig. 10
Profile
| Cycle | Cycle Point |
|---|---|
| Hold @ 95°c, 2 min 0 secs | |
| Cycling (50 repeats) | Step 1 @ 94°c, hold 10 secs |
| | Step 2 @ 60°c, hold 30 secs, acquiring to Cycling A([Green][1][1]) |
Raw Data For Cycling A.Green
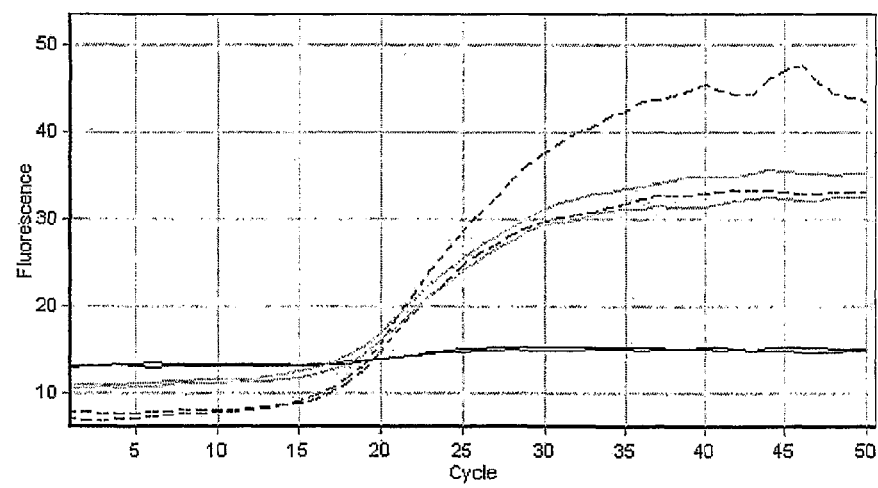
Quantitation data for Cycling A.Green
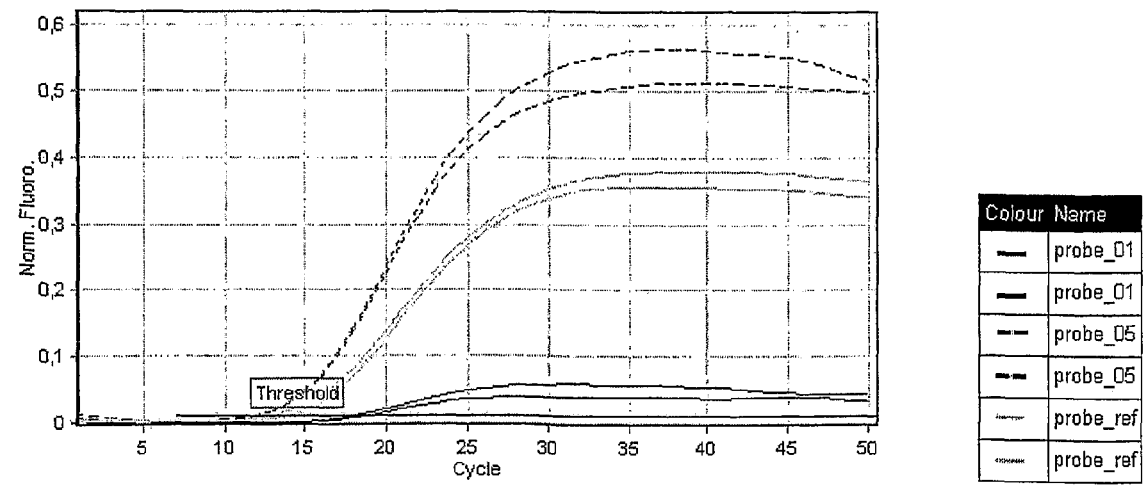
| Colour | Name |
|---|---|
| — | probe_01 |
| — | probe_01 |
| -- | probe_05 |
| -- | probe_05 |
| ⋯ | probe_ref |
| ⋯ | probe_ref |

Fig. 11

Detection of target by melting temperature

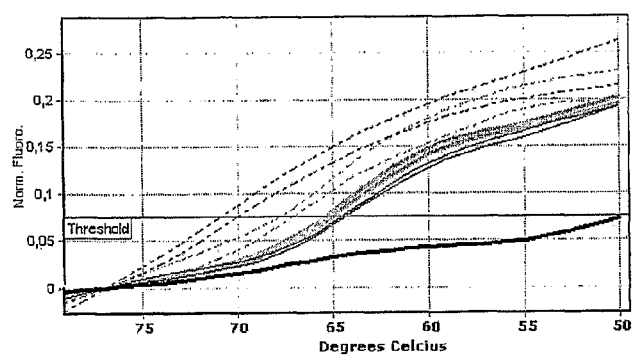

| No. | Colour | Name | Type | Ct |
|---|---|---|---|---|
| 3 |  | probe_02 + amplified Beta-gal wt target | Unknown | 12,89 |
| 4 |  | probe_02 + amplified Beta-gal wt target | Unknown | 12,22 |
| 5 |  | probe_03 + amplified Beta-gal wt target | Unknown | 14,60 |
| 6 |  | probe_03 + amplified Beta-gal wt target | Unknown | 14,96 |
| 7 |  | probe_05 + amplified Beta-gal wt target | Unknown | 9,08 |
| 8 |  | probe_05 + amplified Beta-gal wt target | Unknown | 9,97 |
| 9 |  | probe_ref + amplified Beta-gal wt target | Unknown | 15,52 |
| 10 |  | probe_ref + amplified Beta-gal wt target | Unknown | 15,73 |
| 11 |  | no probe + amplified Beta-gal wt target | Unknown |  |

Profile for measurement

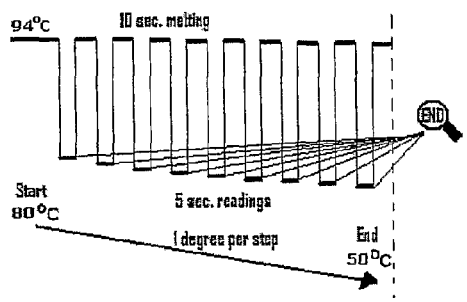

— Probe_01 — Probe_02 -- Probe_05 --- Probe_06 — Probe_07 ▬ Probe_ref

OLIGONUCLEOTIDES COMPRISING SIGNALLING PAIRS AND HYDROPHOBIC NUCLEOTIDES, STEMLESS BEACONS, FOR DETECTION OF NUCLEIC ACIDS, METHYLATION STATUS AND MUTANTS OF NUCLEIC ACIDS

The text file Sequence_listing.txt, created Jun. 19, 2009, and of size 11 KB, filed herewith, is hereby incorporated by reference.

FIELD OF THE INVENTION

The present invention relates to the field of detecting the status of nucleic acid sequences, such as presence, expression, methylation and/or mutation, in particular single point mutations and other sequences where the variation between the correct target and other targets may vary in as little as one nucleotide. The invention relates to oligonucleotides and oligonucleotide analogues comprising a signalling pair (for example a fluorophore and a quencher) as well as at least one hydrophobic nucleotide. The invention also relates to new ways of detecting sequence differences and optimizing conditions by using oligonucleotide analogues and readily available instruments. In particular the invention relates to specifically detecting quantity of a target nucleic acids or detecting one sequence over others that may vary in as little as one nucleotide using oligonucleotides or oligonucleotide analogues comprising a signalling pair and at least one hydrophobic nucleotide, such as a nucleotide analogue comprising an intercalator.

BACKGROUND OF THE INVENTION

Nucleic acids, such as DNA and RNA as well as a number of nucleic acid analogues such as PNA, HNA, MNA, ANA, LNA, INA, CNA, CeNA, TNA, (2'-NH)-TNA, (3'-NH)-TNA, α-L-Ribo-LNA, α-L-Xylo-LNA, β-D-Xylo-LNA, α-D-Ribo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo[4.3.0]-DNA, Bicyclo[3.2.1]-DNA, Bicyclo[4.3.0] amide-DNA, β-D-Ribopyranosyl-NA, α-L-Lyxopyranosyl-NA, 2'-$R_1$-RNA, 2'-$OR_1$-RNA ($R_1$ being any substituent), α-L-RNA, α-D-RNA, β-D-RNA and others are capable of specifically hybridising to complementary nucleic acid strands. This specific recognition may be utilised to detect the presence of defined nucleic acid sequences for example for diagnostic purposes. It is possible to detect small differences between nucleic acid sequences. It is also possible to determine the amount of mRNA present of a given gene, and thereby describe the expression level of that particular gene.

Many of the available assays rely on the detection of a specific nucleic acid by a complementary detectable probe. It is often required to separate unbound probe from bound probe in order to detect the specific nucleic acid, and this usually requires several time-consuming separation steps.

DNA diagnostics is one of the fastest growing research areas, and now with a more detailed map of the human genome map available day for day aiming for the full sequence in detail, the interest in the field is expected to expand even further. A map of 1.42 million single nucleotide polymorphisms (SNPs) has been described and it has been estimated that at least 60,000 SNPs fall within the human exons.

Interestingly, the genomic DNA sequence differs in average in about one out of 1000 nucleotides between two human beings. Accordingly, specific DNA sequences may be useful for determining the identity of an individual. Furthermore, mutations may be indicative of predisposition to clinical conditions. A classic example in genetic diseases is Sickle cell anemia, a genetic defect caused by a change of a single base in a single gene—the beta-globin gene (GAG is changed to GTG at Codon 6). The search for sequences that only differ in one or two nucleobases, creates the need for tools for detecting nucleic acid sequences with high performance, that are fast and simple to conduct, and are cost effective.

Another major field in biology is methylation of the genome. Methylation of "CpG" duplets in the genome is a key component of epigenetic information and has shown to play an important function in imprinting as well as in a range of clinical situations including mental disorders, cancer biology and viral infections. The commonly used technique for detecting the methylation status of a gene in a sensitive manner is treating the genomic DNA with sodium bisulphite, converting all unmethylated Cytosines "C" into deoxyribose Uracils "dUs" while methylated Cytosines "$^{Me}C$" are unreactive, followed by an amplification reaction. The bisulphite treatment of the genomic DNA converts the DNA into an "A-T" rich, essentially three-nucleotide genome (with the exception of "$^{Me}C$" present in methylated "CpG" duplets) and the difference of a methylated or unmethylated "CpG" duplet is translated into a sequence difference (see FIG. 5). The DNA can be analysed post amplification, by sequencing, restriction enzyme digestion or by the presence or absence of bands on a gel after gel electrophoreses when using Methylation Specific PCR, MSP. Alternatively the DNA can be analysed Real-time PCR using MSP and unspecific dye.

The "A-T" rich nature of the bisulphite treated DNA provides a special challenge to primers and probes in an amplification assay due to the relatively low affinity of "A-T" rich DNAs and the difficult nature of distinguishing between a single "C" and a "T" nucleotide.

Different techniques to detect mutations in nucleic acid sequences for example includes single-stranded conformational analysis, denaturing gradient gel electrophoresis, heteroduplex analysis, chemical mismatch cleavage and direct sequencing. A review of these techniques has been given by Grompe (M. Grompe (1993) Nature Genetics, 5:111-117). Among the variety of techniques also fluorescence based methods are available.

The invention of Real-Time Polymerase Chain Reaction (RT-PCR) has revolutionized the way of determining the status of genes like expression (Real-Time Reverse Transcriptase Polymerase Chain Reaction) in a fast and precise manner, but the technique is also used for differentiating between similar targets. Despite many advances in the technology there is still an unmet need for improvements of these techniques.

Some of the most widely used probes today are Molecular beacons, TaqMan® probes (TaqMan is a registered trademark of Roche Molecular Systems, Inc), Scorpion primers and dual hybridization FRET probes (recently reviewed by Arya et al. (2005) Rev. Mol. Diagn. 5:209-219). Each of these technologies has advantages and disadvantages in relation to each other in different applications. Common to all of these technologies are the difficulty of design, often requiring assistance from computer software or specialists and prolonged optimisation to work (examples of software are programs like Primer Express®. available from Applied Biosytems, United States, Beacon Designer available from Premier Biosoft. and Primer3 Copyright (c) 1996, 1997, 1998, 1999, 2000, 2001, 2004 Whitehead Institute for Biomedical Research. All rights reserved.

The TaqMan® assay uses a DNA based probe comprising a signalling pair consisting of a fluorophore and a quencher. The method preferably requires the fluorophore and the quencher to be positioned in opposite ends of the probe to achieve the best available signal-to-noise ratios. During amplification in the PCR reaction, the probe specifically hybridises to its target sequence that is being amplified. When reaching the TaqMan® probe, the Taq polymerase degrades the probe by using its exonuclease activity, whereby the fluorophore is free to move further away from the quencher eliminating the quenching of the signal. The fluorescence generated by the exonuclease activity is correlated to the amount of target sequence present. By knowing the efficiency of the PCR reaction the fluorescent signal can be used to calculate the starting amount of target sequence.

There have been reported some changes to the TaqMan® probes in order to optimise the specificity and sensitivity of the TaqMan® assay. These changes includes the introduction of Minor Groove Binders and nucleotide analogues such as Locked Nucleic Acid (see further description and references herein below) that was used to increase the affinity to the target sequence and to be able to use shorter probes. However in all of the reported TaqMan® assays, quenching of the fluorophore of the intact probe relies on random coil helix formation The Molecular Beacon ("hairpin" or "stem-loop" probes) comprises two stem sequences, one in each end of a probe, which are able to form a duplex if there is no target sequence available for hybridisation complementary to the sequence separating (the loop sequence) said two stem sequences. The probe usually comprises a signalling pair consisting of a fluorophore and a quencher linked to opposite ends of the probe. When the stem is formed, the fluorophore and quencher are thus in close proximity and the signal is quenched. However if the loop sequence is hybridised to a target sequence, the two stem sequences and thus the fluorophore and quencher are separated, allowing a signal to be generated and read. Since there is no or very little background signal of the probe, it has been claimed that Molecular Beacons can be used for the detection of target sequences in homogenous assays and living cells.

The stem sequences of the Molecular Beacons are unrelated to the target sequence. Proper stem formation and stability is dependent upon the length and G:C content of the stem as well as the conditions of the buffer which it is dissolved in. As target sequences may also vary in G:C content, length and in how similar non-target sequences that might be present, the length and G:C content of the loop sequence will vary from probe to probe. It is therefore necessary to use optimized stem sequences that depends on the loop sequences. Furthermore the Molecular Beacons shall not only compete against reannealing of an amplicon, but also the intra-molecular annealing of the probe.

There have also been published some prior art regarding Stemless Beacons (Linear Beacons) including DNA and PNA based Stemless Beacons. The DNA Stemless beacons (Myanard, US 2005/0227247) are rendered impervious to digestion by 5' to 3' exonuclease activity and 3' extension activity by a polymerase. The quenching of the fluorophore, placed in one end of the probe by the quencher placed in the other end of said probe, when the probe is unbound is controlled by random helix coil formation. Maynard teaches that the reporter molecule and quencher molecule are preferably separated by 18 or 20 bases to achieve optimal signal-to-noise ratio. The document and its prior art claims that said ratio is strongly dependent on length of the probe. Resistance to nuclease digestion is an inherent part of these stemless beacons, and the probes can't therefore be used in nuclease dependent assays like TaqMan® assays.

Gildea et al. (WO 1999/21881) describes PNA based Linear Beacons comprising a signalling pair with the two parts of said pair in each end of the probe. The difference between this invention and the invention of DNA based Linear Beacons are that the backbone monomer unit in Gildea's case is the backbone monomer unit of PNA and not DNA. They teach us that the reduced background of the probe is due to PNAs way of behaving and that there is a clear non-equivalency of structure and function between nucleic acid and PNA probes of similar length and labelling configurations. It is stated that probes described in the document should be unaffected of two of the following things: Probe length, $Mg^{2+}$ concentration, ion strength of the buffer and spectral overlap between fluorophore and quencher, the first three things normally being observed in PNA and a few other DNA analogue based probes only. The document does not describe oligonucleotide analogues comprising hydrophobic molecules inserted into probes. Resistance to nuclease digestion is also part of the probes described by the document (inherent in PNA), and the probes can't therefore be used in nuclease dependent assays like TaqMan® assays.

In the prior art nucleotides and nucleotide analogues comprising signalling pairs have been described:

Kutyavin and co-workers conjugated a MGB molecule to the 3'-end of the probe and used it in a 5'-nuclease PCR assay (Kutyavin et al. (2000) *Nucleic Acids Res.* 28: 655-661), and the same laboratory also described a system, called Eclipse, where the MGB is attached to the 5'-end of the probe and does not require nuclease activity of the polymerase Afonina, I. et al. (1997) *Nucleic Acids Res.* 25: 2657-2660). In both of these systems the polymorphic base (point of potential mismatch) should be placed approximately 5 nucleotides from the attachment site of the MGB, to yield the optimum discrimination between the matched and the mismatched target, this is in contrast to normal DNA based probes that have previously been shown to give the highest difference in melting temperature and hence the highest specificity, if the polymorphic base is placed in the middle of the probe. The quenching of the fluorescence when the probe is unbound is limited to random coiling. The restricted design options can be a disadvantage as it is often necessary to have a high degree of flexibility in the probe design in order to avoid formation of unwanted secondary structures.

Letertre et al. 2003, showed that Locked Nucleic Acid, LNA, could be used in a 5'-nuclease PCR assay, with results comparable to the ones obtained with MGB TaqMan® probes (Letertre, C. et al., (2003)*Mol. Cell. Probes* 17: 307-311). It is however difficult to design optimal LNA containing probes based on two reasons: Firstly the LNA nucleotides are nuclease resistant, and the probe needs to be degraded during the 5'-nuclease assay and secondly LNA nucleotides have an extremely high self-affinity and hence if not carefully designed tend to form secondary structures. It has previously been shown that a DNA-LNA hybrid with only a few LNA nucleotides can form secondary structures that are so stable that the probe is unable to hybridise with complementary, single stranded DNA targets (Filichev, et al. (2004) *Chembiochem.* 5:1673-1679).

Seitz, O. (2000) *Angew. Chem. Int Ed.* 39: 3249-3252) described Stemless Peptide Nucleic Acid (PNA) beacons. The PNA beacons tend to fold up into compact random coiled helixes when unbound to target nucleic acids, which is frequently undesirable. Even though that PNA based technologies offer some advantages over DNA based technologies in some aspects, they are more expensive than DNA based technologies and confers more challenge in synthesizing and finding optimal conditions than for DNA based assays. As PNAs are composed of a combination of a protein and an oligonucleotide, the behaviour of PNAs is not always readily predictable.

WO 2004/033726, describes the measurement of fluorescence in a sample being amplified in the presence of a fluorescent system consisting of a probe with a fluorophore attached and free floating quencher molecules that are double stranded intercalators.

WO 1999/21881, US 2002/0064772 and EP 1484337, describe the linear beacons comprising PNA and related molecules that are insensitive to ionic strength, magnesium concentration, spectral overlap between fluorophore and quencher and length of probe. Probes comprising hydrophobic molecules are not included or discussed in these patents.

US 2005/0233360, describes a probe with a fluorophore and a quencher in close proximity in the same end of the probe. Upon hybridisation to a complementary nucleic acid will either the fluorophore or the quencher interact with the formed duplex (by intercalation or minor groove binding) and the fluorophore will be able to fluoresce without being quenched.

WO 01/73118, describes a probe comprising a fluorophore and optionally a quencher. The fluorophore will behave differently depending on if a mismatch is present in the target nucleic acid or not and is in this way able to distinguish one from the other. The probe can also be used for melting point analysis. The probe usually has to be blocked in the 3'-end to avoid extension.

US 2005/0227247, describes the use of a probe with a fluorophore in one end and a quencher in the other end, where the probe is protected from 5' to 3' exonuclease degradation by one or more inserts of phosphorothioates in the 3' end of the probe. Quenching of the fluorophore takes place due to random coiling.

US 2005/0227257, describes the use of a probe duplex, where one strand contains a fluorophore and the other strand contains a quencher. One of the strands is longer than the other and the quencher and fluorophore will be placed in close proximity if the two strands of the probe pair bind to each other. However in presence of a fully complementary target, the longer probe will preferentially bind to that, and the fluorophore will thus be separated from the quencher and hence allowed to fluoresce. Quenching of the probes is controlled by double helix formation of the two parts of the probe system.

US 2005/0064463, describes probes that optionally may be labelled with a fluorophore and a quencher as well as comprising a minor groove binder (MGB) at the end of the probe. The MGB increases the affinity for complementary DNA and shorter and more specific probes can therefore be used.

US 1999/5925517 and US 2000/6103476, describe the hairpin probes called "molecular beacons". The probes comprise a fluorophore and a quencher one in each ends of an oligonucleotide or oligonucleotide analogue. Said oligonucleotide or oligonucleotide analogue is divided into the sequences, sequence 1 and 3 make up the stem in the hairpin structure, when the probe is not bound to any target nucleic acids and sequence 2 is complementary to the target nucleic acid. The background fluorescence is dependent on the double helix formation of sequence 1 and 3.

WO 03/052132, describes hairpin probes comprising Intercalating pseudonucleotides to increase affinity for target nucleic acids, increase nuclease stability, as fluorescent tags and/or decrease the self-affinity. The invention and description does not discuss the concept of "Stemless Beacons" according to the present invention. The document also describes the use of complementary probes for the detection of target nucleic acids, but contrary to the findings in the present invention it does not describe Stemless quenching of an unbound probe.

US 2000/6037130, describes triple labelled hairpin probes with a shorter wavelength harvester and a longer wavelength emitter and a quencher. The presence of the extra fluorophore compared to standard molecular beacons increases the fluorescent yield and hence the signal-to-noise ratio.

US 2002/6355421, describes methods, kits and composition of hairpin shaped PNA molecular beacons. The document does not describe the concept of Stemless beacons.

US 2005/0158720, describes Tripartite molecular beacons (TMBs), that comprise three oligonucleotide components one forming a hairpin structure and the two others complementary to the respective sides of the formed stem.

All patent and non-patent references cited in the application, are also hereby incorporated by reference in their entirety.

SUMMARY OF THE INVENTION

It has long been an interest of the scientist to be able to detect, quantify and identify target sequences of nucleic acids. Several techniques have been developed for that purpose, like "Molecular Beacons" ("hairpin probes") and "TaqMan", however all the currently available tools and techniques have some limitations and draw backs. The Molecular Beacons are hairpin shaped probes that, at the annealing temperature in a real-time PCR, not only has to compete against reannealing of the amplicon but also the intra-molecular annealing of the probe. Optimisation, stringent conditions and design of probes are therefore a necessity. In contrast to the formation of an intra-molecular stem formation, the TaqMan probes are however dependent on random coiled helix structure to quench fluorescence of unbound probes as well as dependent on the nuclease activity of a polymerase to "activate" the fluorophore. Surprisingly, the present invention discloses that hydrophobic molecules covalently inserted into an oligonucleotide or oligonucleotide analogue facilitates a folding of the unbound oligonucleotide and at the same time said hydrophobic molecules do not prevent hybridisation with a target sequence if present. The probes presented in the present invention for the first time combines the tendency of hydrophobic molecules to shield or lower the exposure of the hydrophobic surface to an aqueous solution by interacting with other hydrophobic molecules and the increased interaction between a two part signalling pair with one part in each half of an oligonucleotide analogue (see FIG. 1).

Hence interaction of the signalling pair of the unbound probes presented by the present invention is not solely due to random helix coiling, but does on the other hand not require an intra molecular stem structure designed to effect quenching of the unbound probes. Similar to the previous disclosed "Molecular Beacons" the probes according to the present invention have a good signal-to-noise ratio. Therefore the probes according to the present invention are also designated "Stemless Beacons" herein. The Stemless Beacons according to the present invention are generally shorter than their corresponding molecular beacons, because they generally do not comprise complementary regions (i.e. no "stem"). They are easier to design and optimize and the presence of the hydrophobic groups can furthermore ease purification of said probes. As outlined above it is not necessary to design intramolecular self-annealing stretches that have to have an annealing temperature above reading temperature and below the temperature where it otherwise would compete with the binding to the target nucleic acid. The Stemless Beacons described in the present invention have a better signal-to-noise ratio than their corresponding linear probes without insertions of hydrophobic molecules and can be used in nuclease dependent as well as nuclease independent assays.

One of the major challenges for the molecular probes is to be able to distinguish between very similar targets varying in as little as one nucleotide. Generally speaking the shorter the probe is, the larger influence on affinity one mismatch will have and hence the easier it would be to distinguish between a fully complementary target and a mismatched one.

The present invention describes a new type of molecular probes that are easy to design and have low background fluorescence. The probes are comprised of nucleotides and or nucleotide analogues, a signalling pair (for example a fluorophore and a quencher) and at least one extra hydrophobic moiety, that will facilitate better signal-to-noise ratio, than if said nucleotide or nucleotide analogue did not comprise said hydrophobic molecule(s). The probes described herein are useful for a number of different application including diagnosis of expression, presence of a target nucleic acids, such as specific alleles, single nucleotide polymorphisms (SNPs), mutations and methylation status (epigenetic information).

Hence, it is a first objective of the present invention to provide oligonucleotide analogues comprising a signalling pair and at least one hydrophobic molecule, preferably a hydrophobic nucleotide as described herein below, wherein the signal-to-noise ratio of said oligonucleotide analogue is significantly higher or lower (different from the value 1) than the signal-to-noise ratio of a corresponding oligonucleotide or oligonucleotide analogue not comprising said hydrophobic molecule(s).

It is thus an objective of the present invention to provide an oligonucleotide analogue comprising a signalling pair and at least one hydrophobic nucleotide of the general structure

wherein

X is a nucleotide or nucleotide analogue or a backbone monomer unit capable of being incorporated into the backbone of a nucleic acid or nucleic acid analogue, Q is a hydrophobic molecule according to the present invention and is not taken part in specific hydrogen bonding nor part of the signalling pair; and Y is a linker moiety linking said nucleotide or nucleotide analogue or backbone monomer unit and said hydrophobic molecule wherein the signal-to-noise ratio of said oligonucleotide analogue, when said oligonucleotide analogue is going from being unhybridised to a target nucleic acid to being hybridised to a target nucleic acid or vice versa, is significantly improved over the signal-to-noise ratio of a hybrid between a corresponding oligonucleotide or oligonucleotide analogue, not comprising said hydrophobic molecule(s), consisting of the same nucleotide sequence as said oligonucleotide analogue and said target nucleic acid (corresponding hybrid).

More specifically, it is an objective of the present invention to provide an oligonucleotide analogue comprising a consecutive sequence of n nucleotides and/or nucleotide analogues and at least one hydrophobic nucleotide, wherein said oligonucleotide analogue is covalently linked to a signalling pair, wherein the hydrophobic nucleotide has the general structure

wherein

X is a nucleotide or nucleotide analogue or a backbone monomer unit capable of being incorporated into the backbone of a nucleic acid or nucleic acid analogue, Q is a hydrophobic molecule which is not taking part in Watson-Crick hydrogen bonding; and Y is a linker moiety linking said nucleotide or nucleotide analogue or backbone monomer unit and said hydrophobic molecule; and wherein n is an integer of at least 4; and wherein the at least one hydrophobic nucleotide is positioned at the most 9 nucleotides and/or nucleotide analogues from one end; and wherein the signalling pair consists of a two part system, wherein one part is positioned within 6 nucleotides and/or nucleotide analogues from the 5' end and the other part is positioned within 6 nucleotides or nucleotide analogues from the 3' end;

wherein the parts of the signalling pair are not identical to the hydrophobic nucleotide, with the proviso that when one part of the signalling pair is positioned as a dangling end at the 5' end, then the first nucleotide or nucleotide analogue at the 5' end is not a hydrophobic nucleotide and when one part of the signalling pair is positioned as a dangling end at the 3' end, then the first nucleotide or nucleotide analogue at the 3' end is not a hydrophobic nucleotide.

It should be noted that even though some hydrophobic molecules may generate a detectable signal alone or as part of a pair, the hydrophobic molecule mentioned above is not considered to be part of said signalling pair. Thus, the oligonucleotide analogue comprises a hydrophobic nucleotide and two parts of a signalling pair.

The inventor also found that oligonucleotide analogues that have increased nuclease stability could be useful for end-point determinations, after for example an amplification reaction including polymerases comprising exonuclease activity. Hence it is a second objective of the present invention to provide methods for using oligonucleotide analogues with increased exo- and/or endo-nuclease stability, (for example any of the oligonucleotide analogues according to the present invention) and standard conditions that can be used for the detection and/or identification of a large range of different target sequences. These methods can also be used as a fast method for optimizing conditions for specific assays.

Thus, it is an objective of the present invention to provide methods of detecting hybridisation between an oligonucleotide analogue according to the invention and a target sequence in a mixture of nucleic acids comprising the steps of 1) providing a mixture of nucleic acids that might comprise a target sequence; and
2) providing an oligonucleotide analogue according to the invention; and
3) incubating said nucleic acids and said oligonucleotide analogue under conditions allowing for hybridisation; and
4) detecting hybridisation.

It is also an objective of the invention to provide methods of detecting, identifying and/or quantifying hybridisation between an oligonucleotide analogue according to the invention and a target sequence in a template during amplification.

a) providing a mixture of nucleic acids, which is desirable to use for detecting, identifying and/or quantifying a target sequence and/or a mutant sequence; and
b) providing an amplification buffer comprising an amplification enzyme, a set of primers, and an oligonucleotide analogue according to the present invention, wherein said primers and said oligonucleotide analogue are capable of hybridizing with said target sequence and/or the mutant sequence, said amplification enzyme is capable of extending a primer in a template directed manner and said amplification buffer includes what is necessary for the amplification enzyme to perform such an extension (except for the primers and template); and c) incubating the primers and oligonucleotide analogue with the mixture of nucleic acids under conditions allowing for hybridization of said primers; and d) using the hybridized sequence(s) for templating extension of the 3' end of said primers by said amplification enzyme with nucleotides, nucleotide analogues, oligonucleotides or oligonucleotide analogues; and e) incubating the nucleic acids, extension products and the oligonucleotide analogue under conditions allowing for hybridisation; and f) detecting hybridisation; and optionally repeating step c) to f).

It is furthermore an objective of the present invention to provide universal methods for the detection or identification of target and/or mutant sequences and fast determination of the optimal reading temperature range in homogenous assays, wherein the method comprises the methods of detecting hybdridisation described herein above, wherein the following steps are added after the last step 5) denaturing the mixture and cool at a fast rate to a set temperature (starting above the affinity temperature); and 6) measure the signal from the signalling pair; and 7) determining the affinity of said nucleic acid analogue comprising a signalling pair by repeating step 1) to 3) and gradually lowering the temperature in step 1) until the temperature is lowered below the affinity temperature It is also an objective of the present invention to provide methods for determining hybridisation comprising the steps of a) providing an oligonucleotide analogue comprising a consecutive sequence of n nucleotides and/or nucleotide analogues and at least one hydrophobic nucleotide, wherein said oligonucleotide analogue is covalently linked to a signalling pair consisting of a two part system, wherein the hydrophobic nucleotide has the general structure

X—Y-Q wherein

X is a nucleotide or nucleotide analogue or a backbone monomer unit capable of being incorporated into the backbone of a nucleic acid or nucleic acid analogue, Q is a hydrophobic molecule which is not taking part in specific Watson-Crick hydrogen bonding; and Y is a linker moiety linking said nucleotide or nucleotide analogue or backbone monomer unit and said hydrophobic molecule; and wherein n is an integer of at least 6; and wherein the two parts of the signalling pair are in closer proximity, when said oligonucleotide analogue is not hybridised to a target sequence than when said oligonucleotide analogue is hybridised to a target sequence; and b) providing a mixture of nucleic acids potentially comprising a target sequence for said oligonucleotide analogue; and c) incubating said nucleic acids and said oligonucleotide analogue under conditions allowing for hybridisation; and d) detecting hybridisation by determining whether the parts of the signalling pair are in close proximity;

e) thereby determining hybridisation.

It is furthermore an objective of the present invention to provide universal methods for the detection, identification or quantification and fast determination of the optimal reading temperature range in an amplification reaction, which comprises the steps of:

1) providing a mixture of nucleic acids, which is desirable to use for detecting, identifying and/or quantifying a target sequence and/or a mutant sequence; and 2) providing a set of primers, an amplification buffer comprising an amplification enzyme, and an oligonucleotide or oligonucleotide analogue, wherein said oligonucleotide or oligonucleotide analogue are nuclease resistant and/or said amplification enzyme does not comprise any nuclease activity; and 3) incubating the primers and oligonucleotide or oligonucleotide analogue with the mixture of nucleic acids under conditions allowing for hybridization; and 4) detecting hybridisation; and 5) gradually increase the temperature while measuring the signal strength at certain intervals until the desired extension temperature is reached, and 6) finish the elongation reaction and denature the formed amplicon, and repeat step c) to f) until a desired amplification has taken place It is also an objective of the present invention to provide methods for amplification of a target sequence, said method comprising the steps of:

1) providing a mixture of nucleic acids optionally comprising said target sequence; and 2) providing a set of primers, an amplification buffer comprising an amplification enzyme, and an oligonucleotide or oligonucleotide analogue, wherein said primers and said oligonucleotide or oligonucleotide analogue is capable of hybridizing to said target sequence or a sequence complementary thereto, with the proviso that when the amplification enzyme comprises nuclease activity then the oligonucleotide or oligonucleotide analogue is nuclease resistant; and 3) incubating the primers and oligonucleotide or oligonucleotide analogue with the mixture of nucleic acids under conditions allowing for hybridization; and 4) detecting hybridisation; and 5) gradually increase the temperature while detecting hybridisation at certain intervals until the desired extension temperature is reached, and 6) finish the elongation reaction and denature the formed amplicon, and repeat step 3) to 6) until a desired amplification has taken place.

Furthermore it is disclosed how the use of at least two Stemless Beacons according to the present invention can be used for the characterisation of single nucleotide polymorphisms and distinguishing between other very similar nucleic acids. Hence it is a third objective of the present invention to provide at least two Stemless Beacons to a mixture of nucleic acids, where said Stemless Beacons are labelled with different signalling pairs respectively homologous complementary to each of the expected possible genotypes.

It is a fourth objective of the present invention to provide kits comprising Stemless Beacons.

LEGENDS TO FIGURES

FIG. 1A) When no complementary target is present, the hydrophobic molecules of the Stemless Beacon like to interact with each other, bringing the fluorophore (dotted ball) and quencher (black square) in close proximity. Hence the fluorophore is quenched. B) If a complementary target is added or formed for example during an amplification reaction, the Stemless Beacon will unfold and bind to that. C) When the Stemless beacon is binding to its complementary target, the fluorophore and quencher are no longer in close proximity, hence the fluorophore will fluoresce.

FIG. 2 Dissociation curve of a Stemless DNA (TaqMan® like) sequence (filled markers, FAM-AAAAAMTCCCGC-GAACTCC-BHQ1) [SEQ ID NO: 1] and a comparable Stemless Beacon (hollow markers, FAM-A2AAA2ATCCCG2CGA2ACT-BHQ1) [SEQ ID NO:2] with 4 insertions of pseudonucleotides comprising hydrophobic molecules (denoted 2, insertions of the phosphordiester of 3-(3,4-dihydroxybutyl)-7,9-dimethylpyrido[3',2':4,5]thieno[3,2-d]pyrimidin-4(3H)-one), comprising the hydrophobic group XXVI from below) hybridized to their matched

[SEQ ID NO: 39]
(diamonds, GCGGGAGTT2G2GGGATTTTTTAG)

and mismatched

[SEQ ID NO: 40]
(squares, GTGGGAGTT2G2GGGATTTTTTAG)

DNA targets respectively. It is clear that the background fluorescence of the Stemless Beacon, SB, is much lower than that from the DNA probe. The target oligonucleotides are underlined with one or two lines if only the DNA or both the SB and DNA probe hybridize to the region respectively. Mismatches in the hybridisation region are highlighted in grey. The label "2" means the inserted pseudonucleotide (Phosphoramidite of 3-(1-O-(4,4'-dimethoxytriphenylmethyl)-2-O-(2-cyanoethyl diisopropylamidophosphite)-1,2-butandiol)-4-N-(7,9-Dimethyl-3H-pyrido[3',2':4,5]thieno[3,2-d]pyrimidin-4-one)) comprising the intercalating hydrophobic group with the number XXVI from the description below.

FIG. 3 The negative derivative to the dissociation curve of a Stemless Beacon (SB, hollow markers, FAM-T2AGG2GCGT2TTTT2T-BHQ1) [SEQ ID NO:3] compared to a Stemless DNA, TaqMan® like probe (solid markers, FAM-ATTTTAGGGCGTTTTTTTG-BHQ1) [SEQ ID NO:4] annealed to their matched target

[SEQ ID NO: 5]
(diamonds, CCGCAAAAAAAC2CCCTAAAATCCC)

and mismatched target

[SEQ ID NO: 6]
(squares, CCGCAAAAAAAC2CCCTAAAATCCC).

Even though that there are 6 more complementary nucleobases in the DNA, the SB binds just as strongly to their complementary target but the binding is more specific. The SB hybridises at 63.7° C. and 49.9° C. to its matched and mismatched targets respectively giving a 13.8° C. difference, while the DNA hybridises at 64.9° C. and 57.1° C. to its matched and mismatched target respectively giving only 7.8° C. difference. The target oligonucleotides are underlined with one or two lines if only the DNA or both the SB and DNA probe hybridize to the region respectively. The mismatch in the hybridisation region is highlighted in grey. The higher signal for the SBs are due to their lower background fluorescence. The label "2" means the inserted pseudonucleotide (Phosphoramidite of 3-(1-O-(4,4'-dimethoxytriphenylmethyl)-2-O-(2-cyanoethyl diisopropylamidophosphite)-1,2-butandiol)-4-N-(7,9-Dimethyl-3H-pyrido[3',2':4,5]thieno[3,2-d]pyrimidin-4-one)) comprising the intercalating hydrophobic group with the number XXVI from the description below.

FIG. 4 A) The partly complementary Stemless Beacons, SBs, when there are no or fewer complementary DNA targets present. The two probes binds to each other and/or folds back on them selves thereby quenching the fluorescence. The point of methylation detection (the polymorphic site) and mismatch between the probes is highlighted with a faint grey bar. B) If a complementary DNA target is added or formed during an amplification step, the SB will preferentially bind to that over binding to the other SB. C) The result will be that the SB complementary to the target is now able to fluoresce and hence can be detected, while the other SB folds back on it self and quenches its own fluorescence.

FIG. 5 The figure illustrates the bisulphite treatment of genomic DNA that converts all unmethylated deoxycytosines (dCs) to deoxyuracils (dUs), while leaving the methylated dCs unchanged as dCs. A) The chemical reaction of sodium bisulphite with dC, B) Genomic DNA, C) bisulphite treated unmethylated DNA and D) bisulphite treated DNA with a single methylated CpG duplet. The thick bar in the middle highlights the CpG duplet, while all the other bars highlight the positions of dCs in the genomic DNA and the change to dUs.

FIG. 6 The amplification profile with gradual increase of temperature while measuring the fluorescence at each stage. First the DNA polymerase is activated according to the manufactures advice. Then the 45 cycles of amplification is done. The cycles comprise the annealing and first measurement (for example 50° C.), after which the temperature is gradually increased in for example 2 degree steps measuring the fluorescence at each stage. This is repeated until the normal extension temperature for example 72° C. is reached. The duration of each measurement stage should be as short as possible. The magnifying glass with "END" written in it and a "1" at the border, illustrates that the fluorescence is measured one (1) time at the end of the stage.

FIG. 7 Amplification profile using endpoint affinity readings. Firstly the DNA polymerase is activated according to the manufacture's instructions. The DNA region is then amplified using the optimal annealing temperature (for example 50° C.) and optionally additional reading points (for example 55° C. and 60° C.). This is repeated until satisfactory amplification has taken place. After amplification an endpoint affinity measurement is carried out where the two strands are alternatively denatured (at up to 95° C.) and then cooled down (for example to 72° C. in the first step) gradually lowering the temperature at each time that it is cooled down (for example with 1° C. per step). The signal is measured every time that the mixtures has been cooled down to the selected temperature in the given step and has been hold there for a short period allowing the probe to anneal to its target. This is repeated until the wanted temperature is reached at least at the level where both probes would bind to their complementary targets (for example 45° C.). The magnifying glass with "END" written in it and a "1" at the border, illustrates that the fluorescence is measured one (1) time at the end of the stage.

FIG. 8 The figure illustrates how it is possible to differentiate fluorescence from the fully complementary (methylated DNA) and the mismatched target (unmethylated DNA) using a protocol as shown in FIG. 6. At 45° C. up to 59° C. the methylated probe (FAM-A2AAA2ATCC2G22GA2ACT- BHQ1) [SEQ ID NO:7] also binds to a small extent to the mismatched target, but at 61° C. and up to 71° C. the binding of the probe is specific for the fully complementary target. In future measurements a reading point of 61° C. could be used for this probe. The polymorphic sites are highlighted in grey. The label "2" means the inserted pseudonucleotide (Phosphoramidite of 3-(1-O-(4,4'-dimethoxytriphenylmethyl)-2-O-(2-cyanoethyl diisopropylamidophosphite)-1,2-butandiol)-4-N-(7,9-Dimethyl-3H-pyrido[3',2':4,5]thieno[3,2-d]pyrimidin-4-one)) comprising the intercalating hydrophobic group with the number XXVI from the description below.

FIG. 9 An example showing how it is possible to distinguish the fluorescent signal from the fully complementary (in this example methylated DNA) and the mismatched non-target (in this example unmethylated DNA) using a protocol as shown in FIG. 7 and either FAM-labeled (FAM-TT1GAAT G1GTTT1T-BHQ1) [SEQ ID NO:8] or HEX-labeled probes (HEX-TT1AAAAAC1C ATTC1AAT1A-BHQ1) [SEQ ID NO:9]. Both probes anneal specifically between 45° C. and 50° C. In future measurements it would be desirable to have a reading point at 46° C. for both probes. It is clear from the different profiles that it is simple to distinguish two related targets, in this example methylated from unmethylated DNA, using the described protocol. The polymorphic site in each probe is highlighted in grey. The label "1" means the inserted pseudonucleotide (Phosphoramidite of (S)-1-(4,4'-dimethoxytriphenylmethyloxy)-3-pyrenemethyloxy-2-propanol) comprising the hydrophobic, intercalating molecule pyrene.

FIG. 10 shows in the upper panel the PCR cycle profile used during the experiment described in example 8. The middle panel and lower panel show the fluorescence raw data and the lower panel shows the quantification data obtained as described in example 8.

FIG. 11 shows in the upper panel results obtained as described in example 9. The lower panel show the measurement profile.

DETAILED DESCRIPTION OF THE INVENTION

Nucleic Acids

Figure 2:
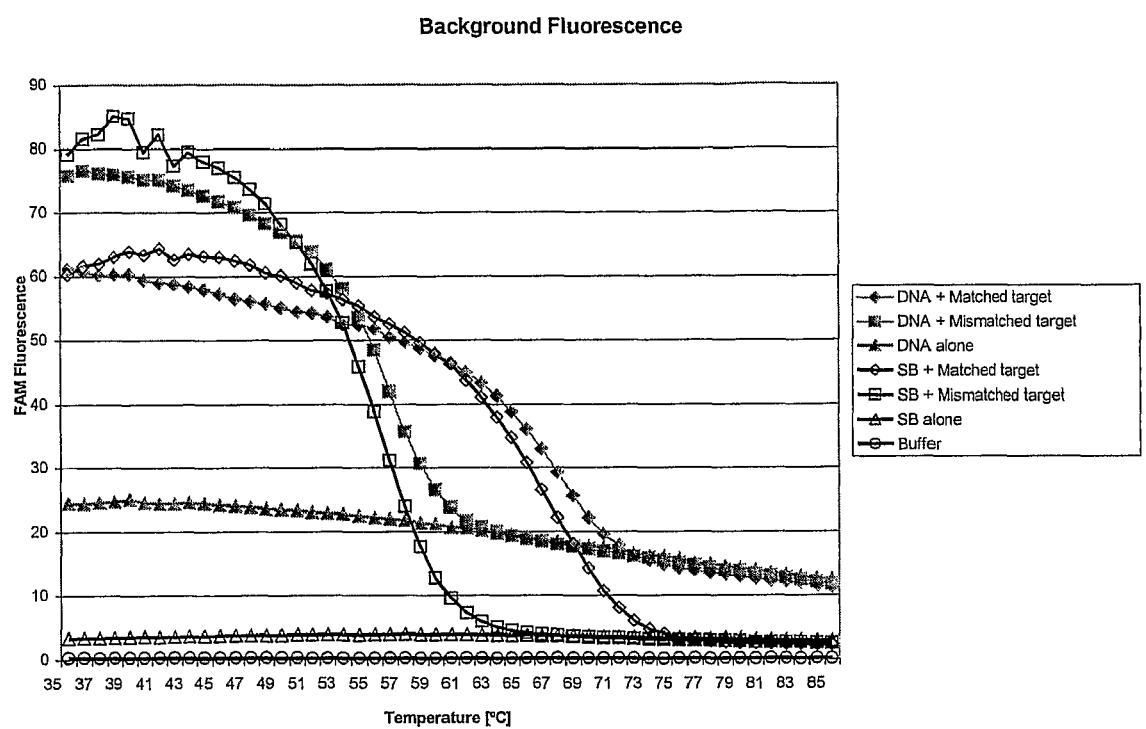

The term "nucleic acid" covers the naturally occurring nucleic acids, DNA and RNA, including naturally occurring derivatives of DNA and RNA such as but not limited to methylated DNA, DNA containing adducts and RNA covalently bound to proteins. The term "nucleic acid analogues" covers synthetic derivatives and analogues of the naturally occurring nucleic acids, DNA and RNA. Synthetic analogues comprise one or more nucleotide analogues.

The term "nucleotide" in general refers to naturally occurring nucleotides, for example naturally occurring ribonucleotides or deoxyribonucleotides or naturally occurring derivatives of ribonucleotides or deoxyribonucleotides. The term "nucleotide analogue" comprises all nucleotide analogues capable of being incorporated into a nucleic acid backbone and capable of specific base-pairing (see herein below), essentially like naturally occurring nucleotides. The term "hydrophobic nucleotide" refers to the hydrophobic nucleotides described in detail herein below. Hydrophobic nucleotides are in general not naturally occurring.

The term "oligonucleotide" refers to oligomers of nucleotides. The term "oligonucleotide analogue" refers to oligonucleotides comprising at least one hydrophobic nucleotide and/or nucleotide analogue and/or pseudonucleotide and optionally naturally occurring nucleotides.

Hence the terms "nucleic acids" or "nucleic acid analogues" designates any molecule, which essentially consists of a plurality of nucleotides and/or nucleotide analogues and/or hydrophobic nucleotides. Hydrophobic nucleotides are described in detail herein below. Nucleic acids or nucleic acid analogues according to the present invention may comprise more different nucleotides and nucleotide analogues with different backbone monomer units (see herein below).

Preferably, single strands of nucleic acids or nucleic acid analogues according to the present invention are capable of hybridising with a substantially complementary single stranded nucleic acid and/or nucleic acid analogue to form a double stranded nucleic acid or nucleic acid analogue. More preferably such a double stranded analogue is capable of forming a double helix. Preferably, the double helix is formed due to hydrogen bonding, more preferably, the double helix is a double helix selected from the group consisting of double helices of A form, B form, Z form and intermediates thereof.

Hence, nucleic acids and nucleic acid analogues according to the present invention includes, but is not limited to the kind of nucleic acids and/or nucleic acid analogues selected PNA, HNA, MNA, ANA, LNA, INA, CNA, CeNA, TNA, (2'-NH)-TNA, (3'-NH)-TNA, α-L-Ribo-LNA, α-L-Xylo-LNA, β-D-Xylo-LNA, α-D-Ribo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo[4.3.0]-DNA, Bicyclo[3.2.1]-DNA, Bicyclo[4.3.0]amide-DNA, β-D-Ribopyranosyl-NA, α-L-Lyxopyranosyl-NA, 2'-R$_1$-RNA, 2'-OR$_1$-RNA (R$_1$ being a substituent), α-L-RNA, α-D-RNA, β-D-RNA and mixtures thereof and hybrids thereof, as well as phosphorous atom modifications thereof, such as but not limited to phosphorothioates, methyl phospholates, phosphoramidiates, phosphorodithiates, phosphoroselenoates, phosphotriesters and phosphoboranoates. In addition non-phosphorous containing compounds may be used for linking to nucleotides such as but not limited to methyliminomethyl, formacetate, thioformacetate and linking groups comprising amides. In particular nucleic acids and nucleic acid analogues may comprise one or more hydrophobic nucleotides according to the present invention.

Within this context "mixture" is meant to cover a nucleic acid or nucleic acid analogue strand comprising different kinds of nucleotides or nucleotide analogues. Furthermore, within this context, "hybrid" is meant to cover nucleic acids or nucleic acid analogues comprising one strand which comprises nucleotides or nucleotide analogues with one or more kinds of backbone and another strand which comprises nucleotides or nucleotide analogues with different kinds of backbone. By the term "duplex" is meant the hybridisation product of two strands of nucleic acids and/or nucleic acid analogues, wherein the strands preferably are of the same kind of nucleic acids and/or nucleic acid analogues.

By HNA is meant nucleic acids as for example described by Van Aetschot et al., 1995. By MNA is meant nucleic acids as described by Hossain et al, 1998. ANA refers to nucleic acids described by Allert et al, 1999. LNA may be any LNA molecule as described in WO 99/14226 (Exiqon), preferably, LNA is selected from the molecules depicted in the abstract of WO 99/14226. More preferably LNA is a nucleic acid as described in Singh et al, 1998, Koshkin et al, 1998 or Obika et al., 1997. PNA refers to peptide nucleic acids as for example described by Nielsen et al., 1991. INA refers to nucleic acids comprising Intercalator pseudonucleotides as described in patent WO 03/051901.

The term "nucleotide" designates the building blocks of nucleic acids or nucleic acid analogues and the term nucleotide covers naturally occurring nucleotides and derivatives thereof as well as nucleotides capable of performing essentially the same functions as naturally occurring nucleotides and derivatives thereof. In general however, and more preferably, the term "nucleotide" as used herein only refers to naturally occurring nucleotides and naturally occurring derivatives thereof. Naturally occurring nucleotides comprise deoxyribonucleotides comprising one of the four nucleobases adenine (A), thymine (T), guanine (G) or cytosine (C), and ribonucleotides comprising on of the four nucleobases adenine (A), uracil (U), guanine (G) or cytosine (C).

Nucleotide analogues may be any nucleotide like molecule that is capable of being incorporated into a nucleic acid backbone and capable of specific base-pairing.

Non-naturally occurring nucleotides (nucleotide analogues) according to the present invention includes, but is not limited to the nucleotides selected from PNA, HNA, MNA, ANA, LNA, INA, CNA, CeNA, TNA, (2'-NH)-TNA, (3'-NH)-TNA, α-L-Ribo-LNA, α-L-Xylo-LNA, β-D-Xylo-LNA, α-D-Ribo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo[4.3.0]-DNA, Bicyclo[3.2.1]-DNA, Bicyclo[4.3.0]amide-DNA, β-D-Ribopyranosyl-NA, α-L-Lyxopyranosyl-NA, 2'-R$_1$-RNA, 2'-OR$_1$-RNA (R$_1$ being a substituent), α-L-RNA, α-D-RNA, β-D-RNA.

The function of nucleotides and nucleotide analogues according to the present invention is to be able to interact specifically with complementary nucleotides via hydrogen bonding of the nucleobases of said complementary nucleotides as well as to be able to be incorporated into a nucleic acid or nucleic acid analogue. Naturally occurring nucleotides, as well as some nucleotide analogues are capable of being enzymatically incorporated into a nucleic acid or nucleic acid analogue, for example by RNA or DNA polymerases, however nucleotides or nucleotide analogues may also be chemically incorporated into a nucleic acid or nucleic acid analogue.

Furthermore nucleic acids or nucleic acid analogues may be prepared by coupling two smaller nucleic acids or nucleic acid analogues to another, for example this may be done enzymatically by ligases or it may be done chemically.

Nucleotides or nucleotide analogues comprise a backbone monomer unit and a nucleobase. The nucleobase may be a naturally occurring nucleobase or a derivative thereof or an analogue thereof capable of performing essentially the same function. The function of a nucleobase is to be capable of associating specifically with one or more other nucleobases via hydrogen bonds. Thus it is an important feature of a nucleobase that it can only form stable hydrogen bonds with one or a few other nucleobases, but that it can not form stable hydrogen bonds with most other nucleobases usually including itself. The specific interaction of one nucleobase with another nucleobase is generally termed "base-pairing".

Base pairing results in a specific hybridisation between complementary nucleotides. Complementary nucleotides according to the present invention are nucleotides that comprise nucleobases that are capable of base-pairing.

Base pairing between nucleobases of naturally occurring nucleotides is herein also referred to as Watson-Crick hydrogen bonding. Watson-Crick hydrogen bonding involves that adenine (A) forms a base pair with thymine (T), as does guanine (G) with cytosine (C) in DNA. In RNA, thymine is replaced by uracil (U).

Thus, of the naturally occurring nucleobases adenine (A) pairs with thymine (T) or uracil (U); and guanine (G) pairs with cytosine (C). Accordingly, e.g. a nucleotide comprising A is complementary to a nucleotide comprising either T or U, and a nucleotide comprising G is complementary to a nucleotide comprising C.

Nucleotides according to the present invention may further be derivatised to comprise an appended molecular entity. The nucleotides can be derivatised on the nucleobases or on the backbone monomer unit. Preferred sites of derivatisation on the bases include the 8-position of adenine, the 5-position of uracil, the 5- or 6-position of cytosine, and the 7-position of guanine. The heterocyclic modifications can be grouped into three structural classes: Enhanced base stacking, additional hydrogen bonding and the combination of these. Modifications that enhance base stacking by expanding the π-electron cloud of planar systems are represented by conjugated, lipophilic modifications in the 5-position of pyrimidines and the 7-position of 7-deaza-purines. Substitutions in the 5-position of pyrimidines modifications include propynes, hexynes, thiazoles and simply a methyl group; and substituents in the 7-position of 7-deaza purines include iodo, propynyl, and cyano groups. It is also possible to modify the 5-position of cytosine from propynes to five-membered heterocycles and to tricyclic fused systems, which emanate from the 4- and 5-position (cytosine clamps). A second type of heterocycle modification is represented by the 2-amino-adenine where the additional amino group provides another hydrogen bond in the A-T base pair, analogous to the three hydrogen bonds in a G-C base pair. Heterocycle modifications providing a combination of effects are represented by 2-amino-7-deaza-7-modified adenine and the tricyclic cytosine analogue having an ethoxyamino functional group of heteroduplexes. Furthermore, N2-modified 2-amino adenine modified oligonucleotides are among commonly modifications. Preferred sites of derivatisation on ribose or deoxyribose moieties are modifications of nonconnecting carbon positions C-2' and C-4', modifications of connecting carbons C-1', C-3' and C-5', replacement of sugar oxygen, O-4', Anhydro sugar modifications (conformational restricted), cyclosugar modifications (conformational restricted), ribofuranosyl ring size change, connection sites—sugar to sugar, (C-3' to C-5'/C-2' to C-5'), hetero-atom ring—modified sugars and combinations of above modifications. However, other sites may be derivatised, as long as the overall base pairing specificity of a nucleic acid or nucleic acid analogue is not disrupted. Finally, when the backbone monomer unit comprises a phosphate group, the phosphates of some backbone monomer units may be derivatised.

Pseudo-nucleotides are nucleotide analogous capable of being inserted into a nucleic acid or nucleic acid analogue, but does not comprise a nucleobase. A pseudonucleotide may be a hydrophobic molecule attached to its own backbone monomer unit, for example a hydrophobic nucleotide according to the present invention. Pseudonucleotides are usually only inserted chemically and very rarely recognised by natural enzymes.

Oligonucleotide or oligonucleotide analogue as used herein are molecules essentially consisting of a sequence of nucleotides and/or nucleotide analogues and/or pseudo-nucleotides. Preferably oligonucleotide or oligonucleotide analogue comprises 3-200, 5-100, 6-30 individual nucleotides and/or nucleotide analogues and/or pseudo-nucleotides and/or hydrophobic nucleotides, as defined above.

Target Nucleic Acids

A target nucleic acid or target nucleic acid analogue refers to a nucleotide or nucleotide analogue sequence which comprise one or more sites/sequences for hybridisation of one or more oligonucleotide(s) and/or oligonucleotide analogue(s), for example primers or probes. Target sequences may be found in any nucleic acid or nucleic acid analogue including, but not limited to, RNA, genomic DNA, plasmid DNA, cDNA, mitochondrial DNA, bisulphite treated DNA and can for example comprise a wild-type or mutant gene sequence, such as a coding sequence or a regulatory sequence thereof or an amplified nucleic acid sequence, for example as when amplified by PCR, or modified DNA, for example treating with a chemical that can change the chemical composition of the DNA like bisulphite treatment of DNA. A target sequence may be of any length. The site addressed may or may not be one contiguous sequence. For example said site may be composed of two or more contiguous subsequences separated by any number of nucleotides and/or nucleotide analogues. However, preferably the target sequence is contiguous. Preferentially the total length of the site addressed, composed by all subsequences on that particular target nucleic acid or target nucleic acid analogue, by said oligonucleotide and/or oligonucleotide analogue is typically less than 100 nucleotides and/or nucleotide analogues.

The nucleotide analogues comprising at least one signalling pair and at least one hydrophobic molecule according to the present invention are not considered as target nucleic acids.

Mutant Sequences

The term "mutant sequence" according to the present invention covers a sequence which differs from a specific target sequence by at least one, such as 1, for example 2, such as 3, for example 4, such as 5, for example 6, such as 7, for example 8, such as 9, for example 10, such as from 10 to 20, for example from 20 to 50, such as more than 50 nucleobases. For example a mutant sequence according to the present invention may comprise one or more mutations.

The term "mutation" covers the change of one or more nucleotides for another one or more other nucleotides compared to a specific target sequence. Furthermore, the term "mutation" covers deletion and addition of nucleotides within a nucleic acid, for example deletion or addition of nucleotides compared to a target sequence. Additionally it covers the change in the methylation pattern.

The target sequence may comprise a polymorphic site (see details herein below) and thus the target sequence may comprise one polymorphism, whereas the "mutant sequence" may comprise another polymorphism.

In one embodiment the target sequence is a wild type sequence, i.e. the most frequently naturally occurring sequence, whereas the mutant sequence comprises one or more mutations compared to said wild type sequence. Accordingly, a mutation according to the present invention may in one embodiment be a polymorphism, such as a single nucleotide polymorphism (SNP). For example the polymorphism may be indicative of a specific DNA profile. Knowledge of a specific DNA profile may for example be employed to identify an individual. For example a specific DNA profile may be employed to identify a criminal or a potentially criminal or to identify a dead body or part of a dead body.

In another embodiment mutation relates to the methylation or de-methylation of a nucleotide. Accordingly a mutation according to the present invention may in one embodiment be the methylation status of a nucleotide such as the methylation of CpG duplets. For example the methylation may be indicative of a specific DNA profile and knowledge about that profile may be indicative of a disease state. The detection of the methylation status is often carried out after conversion of non-methylated CpG to dUpG duplets by treatment with a chemical for example Sodium Bisulphite.

Furthermore, a specific DNA profile may be employed to determine relationship between individuals, for example parents-child relation ship or more distant relationships. Relationship may also be relationship between different species or different population of a given species.

In one embodiment the mutation may be indicative of a clinical condition or the mutation may be indicative of increased risk of a clinical condition.

Said clinical condition may for example be selected from the group consisting of neoplastic diseases, neurodegenerative diseases, cardiovascular diseases and metabolic disorders including diabetes.

Furthermore, the mutation may be indicative of a specific response to a predetermined drug treatment. For example, the mutation may be indicative of whether an individual will respond positively to said drug treatment or whether an individual can not tolerate a specific drug treatment.

Polymorphic Site

In the present invention the term "polymorphic site" covers a specific position of interest in a nucleic acid. A polymorphic site could for example be a specific position of a known polymorphism, such as a single nucleotide polymorphism (SNP) where the nature of the nucleotide is important for the researcher. It could also be a specific position in a nucleic acid that is important to a researcher for other reasons. Hence the polymorphic site is the position that the user is obtaining information about by using a Stemless Beacon according to the present invention when trying to distinguish between two or more possible targets. Polymorphic sites can be any site of interest in a nucleotide, nucleotide analogue, nucleic acid or nucleic acid analogue.

Accordingly, according to the present invention a polymorphic site is a site which may comprise one of several different nucleotides at one or more positions within the site and where it is of interest to determine which nucleotide(s) are comprised within said site.

The polymorphic site may comprise more than one or more nucleotide/nucleotide analogues, such as at least 2, for example in the range of 2 to 10, such as in the range of 2 to 5. Preferably, the polymorphic site comprises one nucleotide.

Thus, by way of example, if it is of interest to determine whether a specific position within a given target sequence is an A or a G, then that specific site is termed a "polymorphic site" according to the present invention.

The skilled person will readily be able to identify polymorphic sites.

Sample Material Description

The present invention provides methods for detecting nucleic acids or nucleic acid analogues comprising a specific target sequence as well as methods to differentiate between nucleic acids or nucleic acid analogues comprising a specific target sequence and nucleic acids comprising a mutant sequence. Said target sequence may be detected in any useful mixtures comprising nucleic acids and/or nucleic acid analogues.

The mixture may be comprised within a cell, for example within an intact cell. The cell may for example be a prokaryotic cell or a eukaryotic cell, such as a plant cell or a mammalian cell. In such an embodiment the method may be employed for in situ hybridization.

The mixture may for example be a test nucleic acid or nucleic acid analogue sample. Said sample may for example be a synthetically prepared sample, which may or may not have been further processed in vitro. The test nucleic acid or nucleic acid analogue sample may comprise any nucleic acid or nucleic acid analogue, for example DNA, RNA, PNA, HNA, MNA, ANA, LNA, CNA, CeNA, TNA, (2'-NH)-TNA, (3'-NH)-TNA, α-L-Ribo-LNA, α-L-Xylo-LNA, β-D-Xylo-LNA, α-D-Ribo-LNA, [3.2.1]-LNA, Bicyclo-DNA, 6-Amino-Bicyclo-DNA, 5-epi-Bicyclo-DNA, α-Bicyclo-DNA, Tri-cyclo-DNA, Bicyclo[4.3.0]-DNA, Bicyclo[3.2.1]-DNA, Bicyclo[4.3.0]amide-DNA, β-D-Ribopyranosyl-NA, α-L-Lyxopyranosyl-NA, 2'-R-RNA, 2'-OR-RNA, α-L-RNA, α-D-RNA, β-D-RNA and mixtures thereof and hybrids thereof.

Frequently, it is desirable to test the DNA or RNA of an individual, such as a mammal, for example a human being. In that case the test nucleic acid or nucleic acid analogue sample is a sample derived from said individual. The sample may be derived from a body fluid sample for example a blood sample, a biopsy, a sample of hair, nails or the like or any other suitable sample.

The sample may be processed in vitro prior to detection of the presence of corresponding target nucleic acids and/or nucleic acid analogues and/or the mutants hereof. For example the sample may be subjected to one or more purification steps that may purify nucleic acids from the sample completely or partially. Furthermore, the sample may have been subjected to amplification steps, wherein the amount of nucleic acids has been amplified, for example by polymerase chain reaction (PCR), reverse transcription polymerase chain reaction, ligase chain reaction or any other suitable amplification process. Such methods are well known to the skilled person and are for example described in Sambrook J et al. 2000. Molecular Cloning: A Laboratory Manual (Third Edition), Cold Spring Harbor Laboratory Press.

In one preferred embodiment of the present invention the test nucleic acid sample is selected from the group consisting of genomic DNA or an amplification product of genomic DNA, such as a PCR amplification product of genomic DNA.

The method may involve a separation step prior to detection, wherein hybridized oligonucleotide or oligonucleotide analogue is separated from unhybridized oligonucleotide or oligonucleotide analogue, which may facilitate specific detection of only hybridized oligonucleotide or oligonucleotide analogue. For example, the mixture of nucleic acids may be immobilized on a solid support prior to hybridization with the oligonucleotide or oligonucleotide analogue. After hybridization, unhybridised oligonucleotide or oligonucleotide analogue may be washed away and hybridized oligonucleotide or oligonucleotide analogue may be detected.

It is however also comprised within the present invention that detection is performed without a separation step. Accordingly, detection may be performed in a closed tube after addition of nucleic acid mixture, the oligonucleotide analogue according to the invention and other required reagents. Such methods are also referred to as homogeneous methods herein.

The target DNA may for example be a particular gene, a gene segment, a micro satellite or any other DNA sequence. Of particular interest is the detection of particular DNAs, which may be of eukaryotic, prokaryotic, Archae or viral origin. Importantly, the invention may assist in the diagnosis and/or genotyping of various infectious diseases by assaying for particular sequences known to be associated with a particular micro organism. The target DNA may be provided in a complex biological mixture of nucleic acid (RNA and DNA) and non-nucleic acids, for example an intact cell or a crude cell extract.

If the target DNA is double stranded or otherwise have significant secondary and tertiary structure, it may need to be heated prior to hybridization. In this case, heating may occur prior to or after the introduction of the nucleic acids into the hybridization medium containing the oligonucleotide analogue. It may also be desirable in some cases to extract the nucleic acids from the complex biological samples prior to the hybridization assay to reduce background interference by any methods known in the art.

The hybridization and extraction methods of the present invention may be applied to a complex biological mixture of nucleic acid (DNA and/or RNA) and non-nucleic acids. Such a complex biological mixture includes a wide range of eukaryotic and prokaryotic cells, including protoplasts; or other biological materials that may harbour target deoxyribonucleic acids. The methods are thus applicable to tissue culture animal cells, animal cells (e.g., blood, serum, plasma, reticulocytes, lymphocytes, urine, bone marrow tissue, cerebrospinal fluid or any product prepared from blood or lymph) or any type of tissue biopsy (e.g. a muscle biopsy, a liver biopsy, a kidney biopsy, a bladder biopsy, a bone biopsy, a cartilage biopsy, a skin biopsy, a pancreas biopsy, a biopsy of the intestinal tract, a thymus biopsy, a mammal biopsy, an uterus biopsy, a testicular biopsy, an eye biopsy or a brain biopsy, homogenized in lysis buffer), plant cells or other cells sensitive to osmotic shock and cells of bacteria, yeasts, viruses, mycoplasmas, protozoa, rickettsia, fungi and other small microbial cells and the like. The assay and isolation procedures of the present invention are useful, for instance, for detecting non-pathogenic or pathogenic micro organisms of interest. By detecting specific hybridization between oligonucleotides or oligonucleotide analogues comprising hydrophobic nucleotide(s) and nucleic acids resident in the biological sample, the presence of the micro organisms may be established.

In one embodiment of the present invention it is desirable to detect the amount of a given target nucleic acid at a given time using the oligonucleotide analogues described herein. This might be done by quantifying the signal from said oligonucleotide analogues or by looking at how much amplification of a given target nucleic acid is needed to create a detectable signal in for example a real-time PCR. However other means of quantification could also be used.

Homologous Nucleic Acids

Nucleic acids, nucleic acid analogues, oligonucleotides or oligonucleotide analogues are said to be homologous complementary, when they are capable of hybridising. Preferably homologous complementary nucleic acids, nucleic acid analogues, oligonucleotides or oligonucleotide analogues are capable of hybridising under low stringency conditions, more preferably homologous complementary nucleic acids, nucleic acid analogues, oligonucleotides or oligonucleotide analogues are capable of hybridising under medium stringency conditions, more preferably homologous complementary nucleic acids, nucleic acid analogues, oligonucleotides or oligonucleotide analogues are capable of hybridising under high stringency conditions.

Those skilled in the art of nucleic acid hybridization are aware of factors commonly used to impose or control stringency of hybridization including the concentration of denaturating agents like for example formamide, salt concentration (i.e. ionic strength), hybridization temperature, concentration of detergent, pH and the presence or absence of chaotropes. Optimal stringency for hybridisation of a probing nucleobase sequence to its target sequence is often found by varying those or some of those factors one by one.

High stringency conditions as used herein shall denote stringency as in comparison to, or at least as stringent as, what is normally applied in connection with Southern blotting and hybridisation as described e.g. by Southern E. M., 1975, J. Mol. Biol. 98:503-517. For such purposes it is routine practise to include steps of prehybridization and hybridization. Such steps are normally performed using solutions containing 6×SSPE, 5% Denhardt's, 0.5% SDS, 50% formamide, 100 µg/ml denatured salmon testis DNA (incubation for 18 hrs at 42° C.), followed by washings with 2×SSC and 0.5% SDS (at room temperature and at 37° C.), and washing with 0.1×SSC and 0.5% SDS (incubation at 68° C. for 30 min), as described by Sambrook et al., 1989, in "Molecular Cloning/A Laboratory Manual", Cold Spring Harbor), which is incorporated herein by reference.

Medium stringency conditions as used herein shall denote hybridisation in a buffer containing 1 mM EDTA, 10 mM $Na_2HPO_4.H_2O$, 140 mM NaCl, at pH 7.0, or a buffer similar to this having approximately the same impact on hybridization stringency. Preferably, around 1.5 µM of each nucleic acid or nucleic acid analogue strand is provided. Alternatively medium stringency may denote hybridisation in a buffer containing 50 mM KCl, 10 mM TRIS-HCl (pH 9.0), 0.1% Triton X-100, 2 mM MgCl2.

Low stringency conditions according to the present invention denote hybridisation in a buffer constituting 1 M NaCl, 10 mM $Na_3PO_4$ at pH 7,0, or a buffer similar to this having approximately the same impact on hybridization stringency.

Alternatively, homologous complementary nucleic acids, nucleic acid analogues, oligonucleotides or oligonucleotide analogues are nucleic acids, nucleic acid analogues, oligonucleotides or oligonucleotide analogues substantially complementary to each other over a given sequence, such as more than 70% complementary, for example more than 75% complementary, such as more than 80% complementary, for example more than 85% complementary, such as more than 90% complementary, for example more than 92% complementary, such as more than 94% complementary, for example more than 95% complementary, such as more than 96% complementary, for example more than 97% complementary.

Preferably said given sequence is at least 4 nucleotides long, for example at least 7 nucleotides, such as at least 10 nucleotides, for example at least 15 nucleotides, such as at least 20 nucleotides, for example at least 25 nucleotides, such as between 10 and 500 nucleotides, for example between 4 and 100 nucleotides long, such as between 6 and 30 nucleotides long. More preferably homologous complementary oligonucleotides or oligonucleotide analogues are substantially homologous complementary over their entire length.

A sequence of nucleotides or nucleotide analogues is said to be complementary to another sequence of nucleotides or nucleotide analogues, when all nucleobases of the first sequence of nucleotides or nucleotide analogues are capable of forming Watson-Crick hydrogen bonds with all nucleobases of the second sequence.

Specificity of Hybridization

The specificity of hybridisation of nucleic acids and/or nucleic acid analogues and/or oligonucleotides and/or oligonucleotide analogues refers to the ability of which said hybridisation event distinguishes between homologous complementary hybridisation partners according to their sequence differences under given stringency conditions. Often it is the intention to target only one particular sequence (the target sequence) in a mixture of nucleic acids and/or nucleic acid analogues and/or oligonucleotides and/or oligonucleotide analogues and to avoid hybridization to other sequences even though they have strong similarity to said target sequence. Sometimes only one or few nucleotides differ among target and non-target sequences in the sequence-region used for hybridization.

High specificity in hybridisation as used herein denotes hybridisation under conditions, for example high stringency conditions, at which an oligonucleotide or oligonucleotide analogue will hybridise with a homologous target sequence significantly better than to any nearly identical sequence differing only from said target sequence by one or few base-substitutions.

Cross-Hybridisation

The term cross-hybridisation covers unattended hybridisation between at least two nucleic acids and/or nucleic acid analogues, i.e. cross-hybridisation may also be denoted intermolecular hybridisation. Hence the term cross-hybridization may be used to describe the hybridisation of for example a nucleic acid probe or nucleic acid analogue probe sequence to other nucleic acid sequences and/or nucleic acid analogue sequences than its intended target sequence.

Often cross-hybridization occurs between a probe and one or more homologous complementary non-target sequences, even though these have a lower degree of complementarity than the probe and its complementary target sequence. This unwanted effect could be due to a large excess of probe over target and/or fast annealing kinetics. Cross-hybridization also occurs by hydrogen bonding between few nucleobase pairs, e.g. between primers in a PCR reaction, resulting in primer dimer formation and/or formation of unspecific PCR products.

Especially nucleic acids comprising one or more nucleotide analogues with high affinity for nucleotide analogues of the same type tend to form dimer or higher order complexes based on base pairing. Especially probes comprising nucleotide analogues such as, but not limited to, DNA, RNA, 2'-O-methyl RNA, PNA, HNA, MNA, ANA, LNA, α-L-Ribo-LNA, α-L-Xylo-LNA, β-D-Xylo-LNA, α-D-Ribo-LNA, [3.2.1]-LNA, 2'-R-RNA, 2'-OR-RNA, and mixtures thereof generally have a high affinity for hybridising to other oligonucleotide analogues comprising backbone monomer units of the same type. Hence even though individual probe molecules only have a low degree of complementarity, they tend to hybridise.

Self-Hybridisation

The term self-hybridisation covers the process wherein a nucleic acid or nucleic acid analogue molecule anneals to itself by folding back on itself, generating a secondary structure like for example a hairpin structure, i.e. self-hybridisation may also be defined as intramolecular hybridisation. In most applications it is of importance to avoid self-hybridization. The generation of said secondary structures may inhibit hybridisation with desired nucleic acid target sequences. This is undesired in most assays for example when the nucleic acid or nucleic acid analogue is used as primer in PCR reactions or as fluorophore/quencher labelled probe for exonuclease assays. In both assays self-hybridisation may inhibit hybridization to the target nucleic acid and hence the degree of signal generation in the exonuclease assay is lowered.

Especially nucleic acids comprising one or more nucleotide analogues with high affinity for nucleotide analogues of the same type tend to self-hybridise. Especially probes comprising nucleotide analogues such as, but not limited to 2'-O-methyl RNA, PNA, HNA, MNA, ANA, LNA, α-L-Ribo-LNA, α-L-Xylo-LNA, β-D-Xylo-LNA, α-D-Ribo-LNA, [3.2.1]-LNA, 2'-R-RNA, 2'-OR-RNA generally have a high affinity for self-hybridising. Hence even though individual probe molecules only have a low degree of self-complementarity they tend to self-hybridise.

In some inventions the use of hair-pin structures and other secondary structures are of benefit. This is for example the case for the Molecular Beacons where a fluorophore and a quencher is positioned in each end of an oligonucleotide and where a short stretch of the sequence in one end is complementary to a short sequence in the other end of said oligonucleotide. The two sequences in each end of the oligonucleotide will hybridise to each other, creating a stem structure, when there is no target nucleic acid present (complementary to the sequence separating the two parts making up the stem), bringing the fluorophore and the quencher in close proximity to each other.

Similar to the Molecular beacons "self-hybridisation" facilitated or enhanced by the presence of hydrophobic molecule(s) is also often a desired effect, for example leading to a better interaction of the signalling pair in the stemless beacons described herein, when the probe is unbound. Thus it is comprised within the present invention that the oligonucleotide analogues comprises one or more hydrophobic nucleotides, which may facilitate the formation of a desired three dimensional structure of said oligonucleotide analogue. In the present invention the hydrophobic molecule(s) may have a similar role to that of the stem in the molecular beacons, which is to ensure a good interaction between the signalling pair in an unbound probe. Therefore in the description of the present invention there is distinguished between the desired hydrophobic self-hybridisation (which is not a true self-hybridisation, but rather a self-interaction) and unwanted self-hybridisation caused by hydrogen bonding. Hairpin structures are usually consisting of minimum of 3 complementary base pairs forming the stem structure in the hair-pin, while hydrophobic self-hybridisation in the Stemless Beacons according to the present invention is not depending on base pairing of complementary base pairs to increase interaction of the signalling pair of an unbound probe.

It is still considered hydrophobic self-hybridisation even if one or a few nucleobases should match in a self-complementary way.

Thus, in one embodiment the oligonucleotide analogues according to the present invention do not comprise a consecutive sequence of 3 nucleotides or nucleotide analogues which is complementary to another consecutive sequence of 3 nucleotides and/or nucleotide analogues within said oligonucleotide analogue. Preferably the oligonucleotide analogues according to the invention do not comprise a consecutive sequence of 4 nucleotides or nucleotide analogues which is complementary to another consecutive sequence of 4 nucleotides and/or nucleotide analogues within said oligonucleotide analogue. For example, the oligonucleotide analogues according to the invention do not comprise a consecutive sequence of 6 nucleotides or nucleotide analogues which is complementary to another consecutive sequence of 6 nucleotides and/or nucleotide analogues within said oligonucleotide analogue, For example, the oligonucleotide analogues according to the invention do not comprise a consecutive sequence of 8 nucleotides or nucleotide analogues which is complementary to another consecutive sequence of 8 nucleotides and/or nucleotide analogues within said oligonucleotide analogue. For example, the oligonucleotide analogues according to the invention do not comprise a consecutive sequence of 10 nucleotides or nucleotide analogues which is complementary to another consecutive sequence of 10 nucleotides and/or nucleotide analogues within said oligonucleotide analogue.

Hence it is a preferred embodiment of the present invention to provide oligonucleotide analogues comprising a signalling pair and at least one hydrophobic molecule, where the signal-to-noise ratio of said oligonucleotide analogue is significantly higher or lower (more different from the value 1) than the signal-to-noise ratio of a corresponding oligonucleotide or oligonucleotide analogue not comprising said hydrophobic molecule(s) and where said oligonucleotide analogue is homologous complementary to their target nucleic acid (not comprising a stem structure that is not homologous complementary to the target sequence).

This means that oligonucleotide analogues according to the present invention are easier to design and can be made shorter than their corresponding molecular beacons, as no stem is needed to optimise signal-to-noise ratios.

Melting Temperature

Melting of nucleic acids and nucleic acid analogues refer to thermal separation of the two strands of a double-stranded nucleic acid molecule. The melting temperature ($T_m$) denotes the temperature in degrees centigrade at which 50% helical (hybridised) versus coil (unhybridised) forms are present.

A high melting temperature is indicative of a stable complex and accordingly of a high affinity between the individual strands. Vice versa a low melting temperature is indicative of a relatively low affinity between the individual strands. Accordingly, usually strong hydrogen bonding between the two strands results in a high melting temperature. In addition the melting temperature is dependent on the physical/chemical state of the surroundings. For example the melting temperature is normally dependent on salt concentration and pH.

The melting temperature may be determined by a number of assays, for example it may be determined by using the UV spectrum to determine the formation and breakdown (melting) of hybridisation or by fluorescence.

It is a preferred embodiment of the present invention to determine the melting temperature of oligonucleotide analogues comprising a signalling pair and at least one hydrophobic molecule according to the present invention in the presence of a mixture of nucleic acids.

It a more preferred embodiment of the present invention to determine the melting temperature of oligonucleotide analogues comprising a signalling pair and at least one hydrophobic molecule according to the present invention after performing an amplification reaction of a nucleic acid sequence from a mixture of nucleic acids.

It is an even more preferred embodiment of the present invention to provide a method for determining the melting temperature of oligonucleotide analogues comprising a signalling pair and at least one hydrophobic molecule according to the present invention, wherein the method comprises the steps of a) providing a mixture of nucleic acids or nucleic acid analogues, which is desirable to test for the presence of a target sequence or a mutant sequence; and b) providing a set of primers and an oligonucleotide analogue comprising at least one hydrophobic molecule and a signalling pair as described herein, wherein said primers and said oligonucleotide analogue are capable of hybridizing with said target sequence and/or the mutant sequence; and c) incubating said primers and oligonucleotide analogue with said mixture of nucleic acids and/or nucleic acid analogues under conditions allowing for hybridization of said primers to said nucleic acids and/or nucleic acid analogues; and d) using said hybridized target sequence for templating extension of the 3' end of said primer with nucleotides or nucleotide analogues or oligonucleotides or oligonucleotide analogues; and e) repeating step c) to d) until a satisfactory amplification is reached; and f) denaturing the mixture and cool fast to a temperature that allows hybridisation of said probe to its target sequence and/or the mutant sequence; and g) increase the temperature while measuring the signal from the signalling pair until the melting temperature of the oligonucleotide analogue from its target sequence is determined.

Furthermore, as disclosed by the present invention, intercalation of an intercalator between nucleobases of a double stranded nucleic acid or hydrophobic interactions by groove binding of the hydrophobic molecules may also stabilise double stranded nucleic acids and accordingly result in a higher melting temperature. Thus, frequently, a hybrid between an oligonucleotide analogue according to the present invention and DNA will in general have a higher melting temperature, than a corresponding DNA/DNA hybrid.

Hence it is a preferred embodiment of the present invention to provide oligonucleotides or oligonucleotide analogues comprising a signalling pair and at least one hydrophobic molecule, where the melting temperature of said oligonucleotide analogue is significantly higher than the melting temperature of a corresponding oligonucleotide or oligonucleotide analogue not comprising said hydrophobic molecule(s).

Affinity

Affinity of nucleic acids refers to thermal formation of a double-stranded nucleic acid molecule from two single strands.

The affinity is like the melting temperature ($T_m$) denoted as the temperature in degrees centigrade at which 50% helical (hybridised) versus coil (unhybridised) forms are present. In the perfect system the melting temperature and affinity temperature should be equal or close to equal, however sometimes that equilibration is not reached during a measurement and other conditions or molecules present in the mixture can influence the formation or denaturing of a duplex.

A high affinity is indicative of a stable complex and accordingly of a high affinity between the individual strands. Vice versa a low affinity temperature is indicative of a relatively low affinity between the individual strands. Accordingly, usually strong hydrogen bonding between the two strands results in a high affinity.

Furthermore, as disclosed by the present invention, intercalation of an intercalator between nucleobases of a double stranded nucleic acid or hydrophobic interactions by groove binding of the hydrophobic molecules may also stabilise double stranded nucleic acids and accordingly result in a high affinity or steric effects from hydrophobic molecules may result in a lower affinity.

In addition the affinity is dependent on the physical/chemical state of the surroundings. For example the affinity is normally dependent on salt concentration and pH. The affinity may be determined by a number of ways, for example it may be determined by using the UV spectrum to determine the formation and breakdown (melting) of hybridisation or by fluorescence changes upon annealing or denaturing of two strands.

It is a preferred embodiment of the present invention to determine the affinity of oligonucleotide analogues comprising a signalling pair and at least one hydrophobic molecule according to the present invention to a mixture comprising nucleic acids.

It is an even more preferred embodiment of the present invention to determine the affinity of oligonucleotide analogues comprising a signalling pair and at least one hydrophobic molecule according to the present invention to a mixture comprising nucleic acids after performing an amplification reaction.

It is a most preferred embodiment of the present invention to provide a method for determining the affinity of oligonucleotide analogues comprising a signalling pair and at least one hydrophobic molecule according to the present invention, wherein the method comprises the steps of a) providing a mixture of nucleic acids or nucleic acid analogues, which is desirable to test for the presence of a target sequence or a mutant sequence; and b) providing a set of primers and an oligonucleotide analogue comprising at least one hydrophobic molecule and a signalling pair as described herein, wherein said primers and said oligonucleotide analogue are capable of hybridizing with said target sequence and/or the mutant sequence; and c) incubating said primers and oligonucleotide analogue with said mixture of nucleic acids and/or nucleic acid analogues under conditions allowing for hybridization of said primers to said nucleic acids and/or nucleic acid analogues; and d) using said hybridized target sequence for templating extension of the 3' end of said primer with nucleotides or nucleotide analogues or oligonucleotides or oligonucleotide analogues; and e) repeating step c) to d) until a satisfactory amplification is reached; and f) denaturing the mixture and cool fast to a set temperature starting above the affinity temperature; and g) measure the signal from the signalling pair as soon as said oligonucleotide analogue is hybridised and before the amplicon re-anneal; and h) determine the affinity of said nucleic acid analogue comprising at least one hydrophobic molecule and a signalling pair by repeating step f) to g) while gradually lowering the temperature in step f) until the temperature is lowered to a temperature below the affinity temperature.

The above method has the advantage to overcome problems associated with reannealing of amplicon and displacement of said nucleic acid analogue comprising the signalling pair.

Nuclease Resistance

By the term Nuclease resistance is meant the resistance of oligonucleotides, oligonucleotide analogues, nucleic acids or nucleic acid analogues towards degradation by nucleases. Nucleases is the general term for enzymes that catalyze the hydrolysis of nucleic acids by cleaving chains of nucleotides into smaller units and covers both endonucleases (nucleases that cleave nucleic acids at interior bonds thereby producing fragments of various sizes) and exonucleases (nucleases that release one nucleotide at a time (serially) beginning at one end of a nucleic acid).

Nuclease resistance is routinely measured by incubating oligonucleotides with cellular extracts or isolated nuclease solutions and measuring the extent of intact oligonucleotide remaining over time, usually by gel electrophoresis or spectrophotometrically. An example of measuring the nuclease resistance could comprise the following steps:

a) The oligonucleotide analogues are gel purified and 5'-end-labeled with high performance liquid chromatography-purified $^{32}$P-ATP.

b) The oligonucleotides are then incubated with snake venom phosphodiesterase c) Samples are taken at different time points and reaction quenched immediately d) The oligonucleotide metabolites are then resolved on a 20% denaturing polyacrylamide gel followed by quantification by Phosphor Imager analysis.

A high nuclease resistance means that the nucleotide or nucleotide analogue are stable or only slowly degraded by nucleases compared to the speed of degradation of a comparable DNA sequence at similar conditions, while a low nuclease resistance means that the nucleotide or nucleotide analogue are degraded by nucleases at a speed comparable to the degradation of a corresponding DNA at similar conditions.

In some embodiments of the present invention it is preferred that the nucleotide analogues according to the present invention (Stemless Beacons) have a high nuclease resistance, so that the probes can be used for end-point readings (for example after being present during an amplification reaction), re-used after a measurement or used for further validation and/or quality control.

It is a preferred embodiment of the present invention to provide oligonucleotide analogues comprising a signalling pair and at least one hydrophobic molecule according to the present invention, where the nuclease resistance is significantly higher than the nuclease resistance of the corresponding oligonucleotide or oligonucleotide analogue not comprising said at least one hydrophobic group.

It is an even more preferred embodiment of the present invention to provide oligonucleotide analogues comprising a signalling pair and at least one hydrophobic nucleotide according to the present invention, where the oligonucleotide analogues have a high nuclease resistance towards the potential nuclease activity of a polymerase. For example against the nuclease activity possessed by some of the Taq DNA polymerases.

Hence a preferred embodiment of the present invention is to provide oligonucleotide analogues comprising a signalling pair and at least one hydrophobic molecule according to the present invention, where the oligonucleotide analogues are relatively stable under conditions used for amplification of a nucleic acid.

Preferably said oligonucleotide analogues have a high nuclease resistance so that they during an amplification reaction they are only degraded to a low extent for example only degraded 0%, such as at the most 1%, for example at the most 3%, such as at the most 5%, for example at the most 7%, such as at the most 10%, for example at the most 15%, such as at the most 25%, for example at the most 50%, for example between 0% and 25%, such as between 0% and 15%, for example between 0% and 10%, such as between 0% and 5%. Preferably, aforementioned degradation is obtained after incubation with a given nuclease, preferably an exonuclease, for example a Taq polymerase under conditions allowing for nuclease activity.

Frequently, the oligonucleotide analogues according to the present invention are resistant to nuclease activity in the immediate vicinity of the hydrophobic nucleotide analogues inserted therein. Thus, if the nuclease comprises 5'-3' exonuclease activity, it is preferred that the oligonucleotide analogue according to the present invention comprises at least one hydrophobic nucleotide close to the 5' end, for example a hydrophobic nucleotide positioned within 9, preferably within 6, more preferably within 4, for example within 2 nucleotides or nucleotide analogues from the 5' end. Similarly, if the nuclease comprises 3'-5' exonuclease activity, it is preferred that the oligonucleotide analogue according to the present invention comprises at least one hydrophobic nucleotide close to the 3' end, for example a hydrophobic nucleotide positioned within 9, preferably within 6, more prefer-ably within 4, for example within 2, such as within 1 nucleotides or nucleotide analogues from the 3' end. If the nuclease comprises endonuclease activity, then the oligonucleotide analogue preferably comprises at least one hydrophobic nucleotide in close vicinity to the restriction site of said endonuclease.

On most available real-time PCR instruments it takes a certain amount of time to do readings of signal strengths while lowering the temperature (making a standard affinity measurement). The time passed is often long enough to allow amplicons, which usually have higher affinity temperatures than probes have to their target sequence, to re-anneal interfering with the affinity measurement. However during a real-time PCR measurement, the measuring conditions are normally so that re-annealing of amplicons has not occurred to a large extent.

It is therefore also a preferred embodiment of the present invention to provide a method for the fast determination of the optimal reading temperature range in for example a real-time amplification reaction, using a nuclease resistant probe, which comprises the steps of:

a) Providing a mixture of nucleic acids or nucleic acid analogues, which comprise a target sequence and/or a mutant sequence; and
b) providing a nuclease resistant oligonucleotide or oligonucleotide analogue comprising a signalling pair, wherein said oligonucleotide or oligonucleotide analogue is capable of hybridizing with said target sequence and/or the mutant sequence; and
c) denaturing the mixture and cool at a fast rate to a set temperature (starting above the affinity temperature), and
d) measure the signal from the signalling pair, and
e) determining the affinity of said nucleic acid analogue comprising a signalling pair by repeating step c) to e) and gradually lowering the temperature in step c) until the temperature is lowered below the affinity temperature
f) derive a temperature for future measurements, for example during an amplification reaction of said target nucleic acid, which is below the found annealing temperature for the target nucleic acid and/or above the found temperature for the mutant sequence.

Preferably said oligonucleotide or oligonucleotide analogue is resistant to the nuclease activity of a DNA polymerase, for example to Taq polymerase. Preferably, said oligonucleotide or oligonucleotide analogue capable of hybridising with a target sequence and/or mutant sequence is homologous complementary to said target sequence and/or said mutant sequence.

It is even more preferred if said nuclease resistant oligonucleotide or oligonucleotide analogue comprising a signalling pair also comprises at least one hydrophobic molecule according to the present invention, such as at least one hydrophobic nucleotide. The at least one hydrophobic nucleotide is preferably positioned within the nuclease resistant oligonucleotide analogue as described herein above.

Another preferred method is where the measurement is started below the affinity temperature and the temperature is gradually raised during the repetition of step c) to e).

Also preferred is the method where said nuclease resistant oligonucleotide or oligonucleotide analogue, comprising a signalling pair, is present during an amplification reaction. It is an even more preferred embodiment when the same container, comprising said nuclease resistant oligonucleotide or oligonucleotide analogue, is present during an amplification reaction and used for the above method without having to open the container between amplification and annealing temperature determination (closed tube reaction).

It is also preferred that the time passed between reaching the set temperature until reading the signal is long enough for the relatively small nuclease resistant oligonucleotide or oligonucleotide analogue, comprising a signalling pair, to anneal to its target, but not long enough to allow re-annealing of the full length amplicon, which can interfere significantly with the measurement. This means that when the selected temperature in step c) is reached the time passed before measuring in step d) is 1 second, such as 2 seconds, for example 3 seconds, such as 4 seconds, for example 5 seconds, such as 6 seconds, for example 7 seconds, such as 8 seconds, for example 9 seconds, such as 10 seconds, for example 11 seconds, such as 12 seconds, for example 13 seconds, such as 14 seconds, for example 15 seconds, for example at the most 1 second, such as at the most 2 seconds, for example at the most 3 seconds, such as at the most 4 seconds, for example at the most 5 seconds, such as at the most 6 seconds, for example at the most 7 seconds, such as at the most 8 seconds, for example at the most 9 seconds, such as at the most 10 seconds, for example at the most 11 seconds, such as at the most 12 seconds, for example at the most 13 seconds, such as at the most 14 seconds, for example at the most 15 seconds, such as between 1 and 15 seconds, for example between 3 and 20 seconds.

The affinity temperature of the probe is easily found by a person skilled in art, by looking at the change in signal from said oligonucleotide or oligonucleotide analogue, comprising a signalling pair as a result of change in the annealing temperature. Because the parts of signalling pair in general will be in close proximity when the oligonucleotide analogue is not hybridised to a target sequence, whereas the parts of the signalling pair will not be in close proximity when the oligonucleotide analogue is hybridised to its target sequence, there will be a difference in the signal generated by the signalling pair dependent on whether the oligonucleotide analogue is hybridised with a target sequence or not.

The temperature used as measuring point for said nuclease resistant oligonucleotide or oligonucleotide analogue comprising a signalling pair in future measurements, for example in real-time PCR reactions, may for example be 1° C., such as 2° C., for example 3° C., such as 4° C., for example 5° C., such as 6° C., for example 7° C., such as 8° C., for example 9° C., such as 10° C., for example more than 10° C., such as between 1° C. and 10° C., for example at least 3° C. lower than the annealing temperature of said nuclease resistant oligonucleotide or oligonucleotide analogue to the target sequence found using the above method.

The temperature used as measuring point for said nuclease resistant oligonucleotide or oligonucleotide analogue comprising a signalling pair in future real-time PCR reactions may for example be 1° C., such as 2° C., for example 3° C., such as 4° C., for example 5° C., such as 6° C., for example 7° C., such as 8° C., for example 9° C., such as 10° C., for example more than 10° C., such as between 1° C. and 10° C., for example at least 3° C. higher than the annealing temperature to the mutant sequence found using above method.

The temperature used as measuring point, using said nuclease resistant oligonucleotide or oligonucleotide analogue comprising a signalling pair in future genotype specific real-time PCR reactions, may for example be below the annealing temperature found for the fully complementary target and above the annealing temperature found for the mutant sequence by using the method described above.

The above method has the advantage in getting around the problem of competition between annealing of the probe to the target sequence before formation of the slower formed, but more stable duplex amplicon. However the above mentioned method might not always be preferred. Therefore dependent on the flexibility, robustness and ramping speed of the available instruments, it might be preferred to use the melting temperature for determining optimal measuring temperature in future measurements.

The melting temperature and the affinity temperature are important features of a probe used for detection of a target sequence, for determining the measuring temperature in an experiment. It is therefore also a preferred embodiment of the present invention to provide a method for the fast determination of the optimal reading temperature range in an amplification reaction, using a nuclease resistant probe, which comprises the steps of:

a) Providing a mixture of nucleic acids or nucleic acid analogues, which comprise a target sequence and/or a mutant sequence; and b) providing a set of primers and a nuclease resistant oligonucleotide analogue comprising a signalling pair (probe), wherein said primers and said probe are capable of hybridizing with said target sequence and/or the mutant sequence; and c) incubating said primers and probe with said mixture of nucleic acids and/or nucleic acid analogues under conditions allowing for hybridization of said primers to said nucleic acids and/or nucleic acid analogues; and d) using said hybridized target sequence for templating extension of the 3' end of said primer with nucleotides or nucleotide analogues or oligonucleotides or oligonucleotide analogues; and e) hybridizing said probe to its target sequence and measure the signal strength (for example at the same temperature as the primers are hybridised at), and f) gradually increase the temperature while measuring the signal strength at certain intervals until the desired extension temperature is reached, and g) finish the elongation reaction and denature the formed amplicon, and repeat step c) to g) until a desired amplification has taken place h) determining the melting temperature of probe Preferably said oligonucleotide or oligonucleotide analogue is resistant to the nuclease activity of a DNA polymerase, for example to Taq polymerase. Preferably, said oligonucleotide or oligonucleotide analogue capable of hybridising with a target sequence and/or mutant sequence is homologous complementary to said target sequence and/or said mutant sequence.

It is even more preferred if said nuclease resistant oligonucleotide or oligonucleotide analogue comprising a signalling pair also comprises at least one hydrophobic molecule according to the present invention, such as at least one hydrophobic nucleotide. The at least one hydrophobic nucleotide is preferably positioned within the nuclease resistant oligonucleotide analogue as described herein above.

It is preferred that the time passed between reaching the temperature for hybridising the probe and the first reading of the signal is long enough for the relatively small said nuclease resistant oligonucleotide or oligonucleotide analogue, comprising a signalling pair, to anneal to its target, but not long enough to let re-annealing of the amplicon interfere significantly with the measurement. The following increases in temperature and measurements should be performed as swiftly as possible to minimize the re-annealing of the amplicon.

It is preferred that when the selected temperature in step e) is reached the time passed before measuring is 1 seconds, such as 2 seconds, for example 3 seconds, such as 4 seconds, for example 5 seconds, such as 6 seconds, for example 7 seconds, such as 8 seconds, for example 9 seconds, such as 10 seconds, for example 11 seconds, such as 12 seconds, for example 13 seconds, such as 14 seconds, for example 15 seconds, for example at the most 1 second, such as at the most 2 seconds, for example at the most 3 seconds, such as at the most 4 seconds, for example at the most 5 seconds, such as at the most 6 seconds, for example at the most 7 seconds, such as at the most 8 seconds, for example at the most 9 seconds, such as at the most 10 seconds, for example at the most 11 seconds, for example at the most 12 seconds, for example at the most 13 seconds, such as at the most 14 seconds, for example at the most 15 seconds, such as between 1 and 15 seconds, for example between 3 and 20 seconds.

The preferred temperature rise in step f) is for example 1° C., such as 2° C., for example 3° C., such as 4° C., for example 5° C., such as 6° C., for example 7° C., such as 8° C., for example 9° C., such as between 1° C. and 10° C., for each measurement of signal strength.

The melting temperature of the probe is easily found by a person skilled in art, by looking at the change in signal from said probe as a result of increasing the temperature.

The temperature used as measuring point for said nuclease resistant oligonucleotide or oligonucleotide analogue comprising a signalling pair in future real-time PCR reactions may for example be 0.1° C., such as 0.2° C., for example 0.5° C., such as 1° C., for example 1.5° C. such as 2° C., for example 3° C., such as 4° C., for example 5° C., such as 6° C., for example 7° C., such as 8° C., for example 9° C., such as between 0.1° C. and 10° C., for example at least 3° C. lower than the melting temperature to the target sequence found using above method.

The temperature used as measuring point for said nuclease resistant oligonucleotide or oligonucleotide analogue comprising a signalling pair in future real-time PCR reactions may for example be 1° C., such as 2° C., for example 3° C., such as 4° C., for example 5° C., such as 6° C., for example 7° C., such as 8° C., for example 9° C., such as between 1° C. and 10° C., for example at least 3° C. higher than the annealing temperature to the mutant sequence found using above method.

The temperature used as measuring point, using said nuclease resistant oligonucleotide or oligonucleotide analogue comprising a signalling pair in future genotype specific real-time PCR reactions, is for example below the melting temperature found for the fully complementary target and above the melting temperature found for the mutant sequence by using the method described above.

It is not possible or at least not preferably to use the above method with oligonucleotides that are not nuclease resistant, if the polymerase has an exonuclease activity. In that case the probe will be degraded and there will be no or only little change in signal strength over the temperature range.

The above method has the advantage of providing data at different temperatures for each cycle under conditions used in an amplification reaction. It is therefore easy for a person skilled in art to retrieve information on both the behaviour of the probes and of the amplification reaction, and hence the optimization of the setup performed easily and fast.

Another advantage of probes that are nuclease resistant or assays where nuclease activity is rendered impervious is that the measuring temperature of the probes does not need to correlate with the annealing temperature or extension temperature of the amplification reaction. Furthermore it is possible to use two or more different measuring temperatures during amplification. Using two or more measuring temperatures is especially of benefit when more than one probe is present in the assay. In this way it is possible to read multiple probes at their individual optimized temperatures.

Hydrophobic Group

The present invention relates to oligonucleotide analogues comprising a hydrophobic nucleotide of the general structure

wherein Q is a hydrophobic molecule.

Hydrophobic molecules according to the present invention are hydrophobic and do not take part in Watson-Crick hydrogen bonding. Thus, the hydrophobic molecule according to the present invention is not a naturally occurring nucleobase.

Hydrophobic refers to the tendency of a substance to repel water or to be incapable of completely dissolving in water. Hydrophobic substances are readily soluble in many nonpolar solvents, such as octanol, but only sparingly soluble in water, a polar solvent. One way of determining the hydrophobicity of a compound is related to the compounds solubility in an anhydrous liquid compared to the solubility in water also called partitioning. Organic-water partitioning (P) describes the equilibrium distribution of an organic contaminant dissolved in water between the aqueous phase and an immiscible organic phase. For almost 100 years the two phases has been the octanol-water partition coefficient, and this measure of hydrophobicity is used extensively in describing the behaviour of organic substances in natural waters. The greater the hydrophobicity, the greater is the tendency of that substance to partition into the hydrophobic organic phase. The partition coefficient, therefore, is simply the ratio of the equilibrium concentrations between the two immiscible phases in contact, i.e.

$$P=[\text{organic}]/[\text{aqueous}]$$

This simple relationship assumes that there are no significant solvent interactions (solvent is a continuum), solute-solute interactions (activity coefficient independent of concentration), or anything else.

The ratio of a chemical's concentration in the octanol phase to its concentration in the aqueous phase of a two-phase octanol/water system is also known as a $K_{OW}$ value.

$$P=K_{ow}=[\text{Concentration in octanol phase}]/[\text{Concentration in aqueous phase}]$$

Values of $K_{ow}$ are unit less, and usually measured at room temperature, with a low solute concentration so the solute itself does not affect the distribution.

n-Octanol is an amphiphilic substance, and has both a hydrophobic and hydrophilic piece (the n-alkane and alcohol groups, respectively). This means that it can interact with hydrophilic substances via hydrogen bonding, and with hydrophobic substances via Van Der Waals forces. $K_{ow}$ values range from $10^{-3}$ to $10^7$, (log $K_{ow}$ of −3 to 7), but most measured log $K_{ow}$'s are less than 5, as above this value the compound partition is so strong that it is difficult to measure the aqueous concentration (but higher values can be measured or calculated).

The $K_{ow}$ is not the ratio of a chemical's solubility in octanol and water, since the two phases do not constitute a pure binary system. In particular, there is an appreciable solubility of water in n-octanol, creating a new, more hydrophilic phase. At equilibrium, the organic phase contains 2.3 mol/L of water, and the aqueous phase contains 4.5×10−3 mol/L of octanol. The major factor controlling the octanol-water partition coefficient for nonpolar and slightly polar compounds is apparently the hydrophobicity of that compound, rather than the n-octanol solubility, and the exact nature of the organic phase is less important.

It is in general preferred that the hydrophobic molecule according to the present invention has a $K_{ow}$ which is at least 1.

Other systems used to investigate partitioning include the [water]/[cyclohexan], [water]/[chloroform] and others.

Partition coefficient is an additive constitutive property, i.e., for a given molecule it can be considered as an additive function of its component parts. This is based on the fact that the energetics of transferring a —CH3 group from one environment is relatively constant from compound to compound. This is making it possible to make computer based predictions of partitioning.

Apolar moieties are almost totally incapable of interacting with water molecules and hence water molecules in the vicinity of apolar moieties reorient themselves to maximize hydrogen bonding amongst them. This leads to ordering of water molecules and decrease in entropy of the system, but as described below this is not always the only forces in play. When two apolar moieties or surfaces approach one another, these constrained water molecules are squeezed out and freed into the bulk aqueous phase. Thus, hydrophobic interactions can be viewed as a process of exclusion from aqueous phase and maximization of entropy. Van der Waals interactions have also been proposed to contribute to interactions between apolar surfaces. While the average dipole moment of a nonpolar molecule may be zero, at a given moment a finite dipole moment exists because of instantaneous positions of electrons and protons. This dipole can induce dipole moment in a nearby neutral molecule. The two dipoles can then attract each other.

The partitioning could be determined by the following procedure:

The chemical in question is added to a mixture of octanol and water whose volume ratio is adjusted according to the expected value of $K_{ow}$.

1. The concentration of the solute in the system should be less than 0.01 mol/L in any single phase.
2. Very pure octanol and water must be used.
3. The system, usually in a separator funnel or similar device, is shaken gently until equilibrium is achieved (0.5 hours to 3 days). The system is then centrifuged to separate the two phases and break any emulsions.
4. The two phases are then analyzed by an appropriate technique to determine solute concentrations. If possible, both phases are analyzed to achieve mass balance.

Other techniques are also used, for example can the retention time of the solute in an HPLC be correlated to hydrophobicity (for example Sahu & Pandit (2003) *Journal of Liq. Chrom & Rel. Technol.* 26:135-146). If properly designed experiment, the log of the retention time is linearly related to the log of the $K_{ow}$. Furthermore computer algorithms are used to calculate expected values of compounds (for example the ALOGPS 2.1 (see also below).

The hydrophobic effect is the property that nonpolar molecules like to self-associate in the presence of aqueous solution. In the most extreme case, oils will pool together and fail to be miscible with water; detergents forming micelles and bilayers (as in soap bubbles) are another dramatic consequence of the hydrophobic effect. The effect is also usually described in the context of protein folding, protein-protein interactions, nucleic acid structure, and protein-small molecule interactions. In the case of protein folding, it is used to explain why many proteins have a hydrophobic core which consists of hydrophobic amino acids, such as alanine, valine, leucine, isoleucine, phenylalanine, and methionine grouped together; often coiled-coil structures form around a central hydrophobic axis. The hydrophobic interactions are the main driving force for protein folding to minimize the solvent-exposed non-polar (hydrophobic) surface area. This decreases about 3-4-fold on folding.

It is reasonably clear that the hydrophobic effect is a consequence of the special properties of liquid water, most probably a combination of the strong hydrogen bonding and the small size of water. Hydrophobic effects are not just entropic effects, but have both entropic and enthalpic contributions which vary dramatically with temperature. The underlying basis of the hydrophobic interaction is the lack of strong favourable interactions between polar water molecules and non-polar molecules. This effectively leads to an increase in the interaction between the non-polar molecules. The enthalpy contribution of the hydrophobic interaction is approx. 0 around 20° C., i.e. room temperature, whereas the entropy contribution becomes 0 around 140° C. At temperatures much above room temperature there is increasingly less ordering of the water molecules around a non-polar group. As the temperature decreases, the strength of the hydrophobic interaction decreases. This is the opposite effect to that of H-bonds, which become stronger at lower temperatures.

The hydrophobic effect can be nullified to a certain extent by lowering the temperature of the solution to near zero degrees; at such temperatures, water "prefers" to be in an ordered structure and the order generated by hydrophobic patches is no longer as energetically unfavourable. This is neatly demonstrated by the increased solubility of benzene in water at temperatures lower than room temperature. Typically the hydrophobicity is measured in terms of the free energy of transfer ($G_{transfer}$) of the group of interest from aqueous solution to a non-polar solvent, often octanol. In general, a good correlation is found between $G_{transfer}$ values and other measures of hydrophobicity.

$$\Delta G_{transfer} = -RT \ln P$$

A ln P value above 0 indicates that the compound is more concentrated in the organic phase than in the water phase.

In the present invention a preferred hydrophobic molecule is a hydrophobic molecule that, without taking the backbone monomer unit or linker into account, but with a methyl group at the position of attachment to said linker or backbone monomer unit has a log P value above 0, as either determined experimentally or calculated by using the computer program ALOGPS 2.1 by Virtual Computational Chemistry Laboratory or as a stand-alone version that can be downloaded (AlogPs 2.1 is described by Tetko and Tanchuk (2002) *J. Chem. Inf. Comput. Sci.,* 42:1136-1145 and Tetko and Tanchuk (2001) *J. Chem. Inf. Comput. Sci.,* 41:1407-1421). See also examples included herein for further information on how to calculate log P values according to the present invention.

Thus, said log P value is determined for a hydrophobic molecule, which in place of a linker comprises a methyl group. Thus, for any given hydrophobic nucleotide of the structure X—Y-Q, the log P value is determined by substituting the backbone monomer unit (X) and the linker (Y) with a methyl group and then determining the log P value.

The preferred calculated log P value for a hydrophobic molecule, without taken the backbone monomer unit or linker into account, but with a methyl group at the position of attachment to the oligonucleotide or oligonucleotide analogue, in the present invention is for example above 0, such as above 0.5, for example above 0.75, such as above 1, for example above 1.25, such as above 1.5, for example above 1.75, such as above 2 for example above 2.5, such as above 3, for example above 4, such as above 5.

The hydrophobic molecule according to the present invention preferably does not take part in Watson-Crick hydrogen bonding. In one embodiment the hydrophobic molecule does not take substantially part, such as does not take part in specific hydrogen bonding to other nucleobases. Furthermore it is preferred that the hydrophobic molecule is not part of the signalling pair.

That the hydrophobic effects are present at such a broad temperature range is a great advantage for the present invention. It means that the background signal of an unbound probe at any given temperature during normal assays in aqueous solutions is improved, such as at temperatures in the range of 20° C. to 95° C.

It is therefore a preferred embodiment of the present invention to provide oligonucleotide analogues (for example Stemless beacons) that comprise at least one hydrophobic molecule, such as a hydrophobic nucleotide and a signalling pair according to the present invention that have improved background signals at any temperature between 20° C. and 95° C. over a corresponding nucleic acid not comprising said hydrophobic group(s).

The hydrophobic molecules according to the present invention are covalently linked to a nucleotide, nucleotide analogue or its own backbone monomer unit, optionally through a linker. In general the hydrophobic molecule may be covalently linked to a linker, which is covalently linked to a backbone monomer unit. Nucleotides comprising hydrophobic molecule according to the present invention can be inserted at any position in an oligonucleotide or oligonucleotide analogue. The nucleotides of the present invention should be inserted into oligonucleotides or oligonucleotide analogues comprising other nucleotides or nucleotide analogues. The nucleotide analogues comprising said hydrophobic molecules may or may not also comprise a nucleobase for hybridisation.

In one preferred embodiment of the present invention, the hydrophobic molecule is not directly covalently linked to a nucleotide of a nucleotide analogue comprising a naturally occurring nucleobase. Thus, in this embodiment the linker Y does preferably not comprise a nucleobase and the backbone monomer unit also does not comprise a nucleobase.

The hydrophobic molecules according to the present invention should introduce improved signal-to-noise ratio and optionally one or more of the following features to the oligonucleotide analogues comprising them (for example Stemless probes): Such as improved nuclease resistance and/or increased affinity, but other features such as sequence recognition, nuclease susceptibility, dependency on ionic strength of the buffer solution and/or $Mg^{2+}$ dependency could be determined by the other (non-hydrophobic) nucleotides making up the oligonucleotide analogue (for example the Stemless Beacon).

The prime objectives of the present invention is to provide linear probes (Stemless beacons) comprising hydrophobic molecules that have a better signal-to-noise ratio, than the corresponding linear probes without said hydrophobic molecules. The hydrophobic molecule(s) should facilitate a closer interaction of the two halves of a probe and thereby a closer interaction of the two parts of a signalling pair, when said probe is unbound to a target sequence. It is important that the two halves of the signalling pair interact strongly in the unbound probe (at the measuring temperature(s)), as the signal strength of all signalling pairs used in the present invention is dependent on the distance between the two parts of said pair. When the probe is bound to its target nucleic acid, it is unfolded and the two ends of the probe are separated, but when it is not bound to its target nucleic acid the probe forms a random coiled helix, where the two parts of the signalling pair can come closer to each other. The efficiency of for example FRET is dependent on the inverse sixth power of the intermolecular separation, illustrating the importance of a close proximity of the two parts of the signalling pair in an unbound probe, to obtain good signal-to-noise ratios. The presence of the hydrophobic molecule(s) enhances the interaction of the two halves of the unbound probe.

The preferred hydrophobic groups according to the present invention are hydrophobic groups that are able to induce better interaction between the two parts of the signalling pair and thereby a better signal-noise ratio of the probe. If for example the signalling pair is made up of a fluorophore and a quencher the signal-to-noise ratio is increased by lowering the background signal of the unbound probe. Without being bound by a specific theory it is believed that the main reason for that hydrophobic molecules can increase the interaction of the two parts of the signalling pair in the unbound probe, is hydrophobic interaction between hydrophobic molecule(s) of the other end of the probe according to the present invention, trying to shield each other from having too much surface exposure to the hydrophilic solvent thereby increasing the probability for that the two parts of the signalling pair come in close proximity of each other. The probe is thus not only dependent on a random coiled helix, but has an extra energetic force helping the back folding.

When a probe comprising a signalling pair, where the signal is dependent on the distance between the two parts of said signalling pair, is used to detect, identify or quantify the target sequence, it is important that the signal-to-noise ratio is as far from 1 as possible to avoid false positive and false negative interpretations. It is also important that the background signals in a multiplex reaction are not too high, as this can lead to cross-talk between the fluorophores.

Hence it is a preferred embodiment to provide an oligonucleotide analogue comprising at least one hydrophobic molecule and a signalling pair, according to the present invention, where at least one of said hydrophobic molecule(s) is positioned in one half of said oligonucleotide or oligonucleotide analogue and is able to make hydrophobic interactions with the part of said signalling pair that is positioned in the other half of said oligonucleotide or oligonucleotide analogue such that when the probe is unbound, the interaction between the two parts of said signalling pair is increased compared to the corresponding oligonucleotide or oligonucleotide analogue not comprising said hydrophobic molecule.

Another more preferred embodiment of the present invention is to provide an oligonucleotide analogue comprising a signalling pair and at least one hydrophobic molecule in each half of said oligonucleotide analogue, where said hydrophobic molecules are able to make hydrophobic interactions with each other such that when the probe is unbound, the interaction between the two parts of said signalling pair is increased compared to the corresponding oligonucleotide or oligonucleotide analogue not comprising said hydrophobic molecules.

An increased interaction of the two parts of a signalling pair could either lead to an increase or a decrease in signal strength compared to the corresponding oligonucleotide or oligonucleotide analogue not comprising said intercalator. If the signalling pair consists of a fluorophore and a quencher the increased interaction between the two parts preferably results in a decrease in fluorescence.

It is an even more preferred embodiment of the present invention to provide an oligonucleotide analogue comprising at least one hydrophobic molecule, preferably a hydrophobic nucleotide, a fluorophore and a quencher that have a lower background signal, than the corresponding linear probe without said hydrophobic molecules, such as hydrophobic nucleotide(s), when said oligonucleotide analogue/probe is unbound to a target sequence. Preferably, the aforementioned is in particular the case where said oligonucleotide analogue is used in a closed tube (homogenous) assay.

It is another embodiment of the present invention to provide an oligonucleotide analogue comprising at least one hydrophobic nucleotide and a signaling pair, wherein the parts of the signaling pair are capable of forming an excimer, an exciplex, a FRET complex or a charge transfer complex when in close proximity, wherein said oligonucleotide analogue has a higher background signal, than the corresponding linear probe without said hydrophobic nucleotide(s), when said oligonucleotide analogue/probe is unbound to a target sequence. Preferably, the aforementioned is in particular the case where said oligonucleotide analogue is used in a closed tube (homogenous) assay.

In a preferred embodiment of the present invention the oligonucleotide analogues, such as the Stemless Beacons are consisting of DNA nucleotides, a signalling pair and hydrophobic nucleotides.

The oligonucleotide analogues comprising at least one hydrophobic molecule, such as a hydrophobic nucleotide and a signalling pair according to the present invention may comprise features that are advantageous over the corresponding oligonucleotides or oligonucleotide analogues not comprising said hydrophobic molecules regardless if the probe is used in an exo-nuclease dependent assay or in an exonuclease independent assay.

It is therefore a preferred embodiment of the present invention to provide an oligonucleotide analogue comprising at least one hydrophobic molecule and a signalling pair (the probe) that have a better signal-to-noise ratio, than the corresponding linear probe without said hydrophobic molecule(s), where said probe is used in a nuclease dependent assay. It is more preferred if said assay is dependent on the exo-nuclease activity of a polymerase.

For some applications in the present invention it is necessary that the Stemless Beacon is not degraded or at least not degraded to any significant extent by nuclease activity of for example a DNA polymerase.

Hence in some embodiments of the present invention it is preferred to provide an oligonucleotide analogue comprising at least one hydrophobic molecule and a signalling pair, where the nuclease stability of said oligonucleotide analogue is higher than the nuclease stability of the corresponding oligonucleotide or oligonucleotide analogue not comprising said hydrophobic molecule(s).

One of the major challenges for the molecular probes is to be able to discriminate between very similar targets, varying in as little as one nucleotide. Generally speaking the shorter the probe is the larger influence on affinity one mismatch will have and hence the easier it would be to target a fully complementary target over a mismatched one. High affinity DNA analogues, Minor Groove Binders, MGBs and intercalators have previously been used to generate fluorescent probes that can be made shorter than the corresponding DNA based probes.

It is therefore a preferred embodiment of the present invention to provide an oligonucleotide analogue comprising at least one hydrophobic molecule, such as a hydrophobic nucleotide and a signalling pair, where the melting temperature of a hybrid of said oligonucleotide analogue and a target sequence (such as a DNA sequence) is the same or higher than the melting temperature of a hybrid of the corresponding oligonucleotide or oligonucleotide analogue not comprising said hydrophobic molecule(s) and a target sequence (such as a DNA sequence).

In principle any hydrophobic molecules, such as hydrophobic nucleotides that are able to introduce a significantly better signal-to-noise ratio (further from the value 1) of a probe, than the corresponding linear probe without said hydrophobic molecules, such as hydrophobic nucleotides, can be used in the present invention. That means that in one embodiment, the hydrophobic molecule may be intercalators, minor groove binders and other molecules that have previously been associated with probes. However hydrophobic molecules that are not able to give a significantly better signal-to-noise ratio (further from the value 1), than the corresponding linear probes without said hydrophobic molecules, are not preferred hydrophobic molecules according to the present invention.

Fatty acids, steroids, minor groove binders and intercalators are all hydrophobic molecules useful for the present invention, in particular, such fatty acids, steroids, minor groove binders and intercalators which have a log P value as described above. Preferred hydrophobic molecules of the present invention are however hydrophobic groups that are able to interact with the formed duplex when an oligonucleotide analogue according to the present invention is hybridised to its target sequence without destabilising said duplex, compared to if said hydrophobic molecule(s) have not been present in said oligonucleotide or oligonucleotide analogue. Preferred hydrophobic molecules according to the present invention comprise at least one ring system such as a 5- or 6-membered ring structure. Said ring formation can be either of aromatic or non-aromatic nature. Preferably, said ring systems are made up of C, S, N and/or O, preferably the majority of the members of the ring system are C. The ring systems may independently be substituted on each position. More preferred hydrophobic groups according to the present invention are intercalators and minor groove binders. Most preferred hydrophobic groups according to the present invention are intercalators.

Intercalator

The term intercalator according to the present invention covers any molecular moiety comprising at least one essentially flat conjugated system, which is capable of co-stacking with nucleobases of a nucleic acid. Preferably an intercalator according to the present invention essentially consists of at least one essentially flat conjugated system, which is capable of co-stacking with nucleobases of a nucleic acid or nucleic acid analogue.

An intercalator comprises at least one π (phi) electron system, which according to the present invention can interact with other molecules comprising a π electron system. These interactions can contribute in a positive or negative manner to the hydrophobic interactions of said intercalators. Hunter and Sanders (1990) *J. Am. Chem. Soc.* 112: 5525-5534, have proposed a range of different orientations and conditions where two π electron systems can interact positively with each other.

Preferably, the intercalator comprises a chemical group selected from the group consisting of polyaromates and heteropolyaromates an even more preferably the intercalator essentially consists of a polyaromate or a heteropolyaromate. Most preferably the intercalator is selected from the group consisting of polyaromates and heteropolyaromates.

Polyaromates or heteropolyaromates according to the present invention may consist of any suitable number of rings, such as 1, for example 2, such as 3, for example 4, such as 5, for example 6, such as 7, for example 8, such as more than 8. Furthermore polyaromates or heteropolyaromates may be substituted with one or more selected from the group consisting of hydroxyl, bromo, fluoro, chloro, iodo, mercapto, thio, cyano, alkylthio, heterocycle, aryl, heteroaryl, carboxyl, carboalkoyl, alkyl, alkenyl, alkynyl, nitro, amino, alkoxyl, carbonyl and amido.

When an oligonucleotide analogue according to the present invention is hybridised to a complementary target, the two parts of the signalling pair, for example a fluorophore and quencher, are separated in spatial distance allowing the fluorophore to fluoresce. Oligonucleotide analogues according to the present invention comprise at least one hydrophobic nucleotide comprising a hydrophobic molecule such as flat (hetero)aromatic intercalators, which, when they cannot intercalate between base pairs in a complementary duplex, have hydrophobic interactions with each other or with either part of the signalling pair. In this way they may facilitate an interaction between hydrophobic parts of the hydrophobic molecule and the signalling pair and minimises contact with the water in the buffer. Hence if there are no or fewer complementary targets in a mixture than oligonucleotide analogues such as Stemless Beacons, according to the present invention, the hydrophobic molecule(s), for example intercalators, of the unbound oligonucleotide analogues (probes) will facilitate the two ends of the probe coming into close proximity to each other, thereby enhancing quenching of the fluorophore of the unbound oligonucleotide analogue (such as a Stemless Beacon). This folding back mechanism is independent on sequence and it is therefore not necessary to design a self-complementary stem structure to obtain a proper quenching of the molecule unlike conventional DNA based molecular beacons.

The strength of the interaction between two aromatic systems is determined by the hydrophobic interactions described above as well as electron distribution, density, orientation, distance and the size of the conjugated system.

Accordingly, a hydrophobic molecule according to the present invention may be an intercalator preferably selected from the group consisting of phenanthroline, phenazine, phenanthridine, anthraquinone, pyrene, anthracene, napthene, phenanthrene, picene, chrysene, naphtacene, acridones, benzanthracenes, stilbenes, oxalo-pyridocarbazoles, azidobenzenes, porphyrins, psoralens and any of the aforementioned intercalators substituted with one or more selected from the group consisting of hydroxyl, bromo, fluoro, chloro, iodo, mercapto, thio, cyano, alkylthio, heterocycle, aryl, heteroaryl, carboxyl, carboalkoyl, alkyl, alkenyl, alkynyl, nitro, amino, alkoxyl and/or amido.

Preferably, the intercalator is selected from the group consisting of phenanthroline, phenazine, phenanthridine, anthraquinone, pyrene, anthracene, napthene, phenanthrene, picene, chrysene, naphtacene, acridones, benzanthracenes, stilbenes, oxalo-pyridocarbazoles, azidobenzenes, porphyrins and psoralens.

More preferably, the intercalator is selected from the group consisting of phenanthroline, phenazine, phenanthridine, anthraquinone, pyrene, anthracene, napthene, phenanthrene, picene, chrysene, naphtacene, acridones, benzanthracenes, stilbenes, oxalo-pyridocarbazoles, azidobenzenes, porphyrins and psoralens.

In a preferred embodiment the intercalator is selected from the group consisting of phenanthroline, phenazine, phenanthridine, anthraquinone, pyrene, anthracene, phenanthrene, chrysene, naphtacene, benzanthracenes, stilbenes and porphyrins In another preferred embodiment the hydrophobic group comprises pyrene or pyrido[3',2':4,5]thieno[3,2-d]pyrimidin-4(1H)-one or 7,9-dimethyl-pyrido[3',2',4,5]thieno[3,2-d]pyrimidin-4(3H)-one. The hydrophobic group may also consist of pyrene or pyrido[3',2':4,5]thieno[3,2-d]pyrimidin-4(1H)-one, or 7,9-dimethyl-pyrido[3',2',4,5]thieno[3,2-d]pyrimidin-4(3H)-one.

More preferably the intercalator may be selected from the group of intercalators comprising one of the structures as indicated herein below:

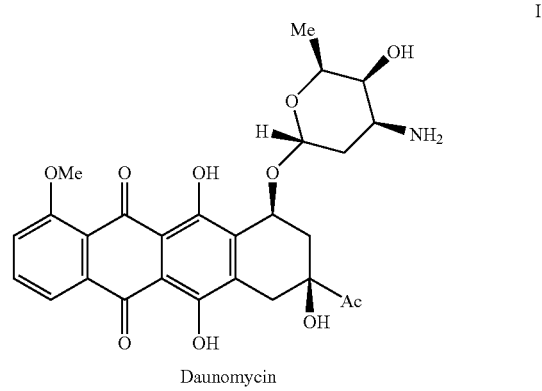

Daunomycin

I

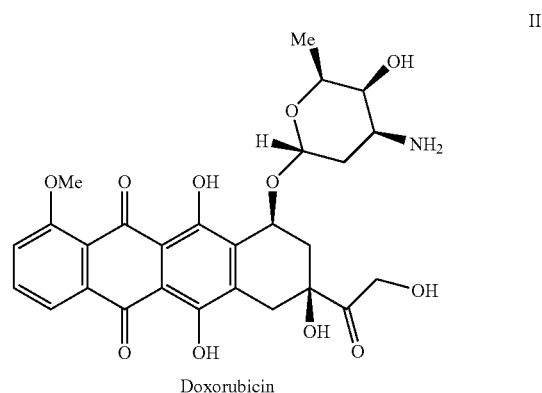

Doxorubicin

II

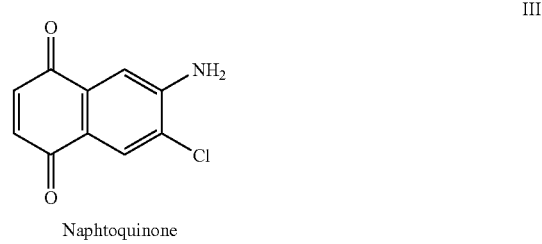

Naphtoquinone

III

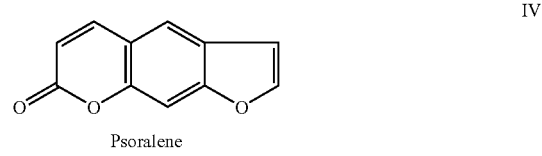

Psoralene

IV

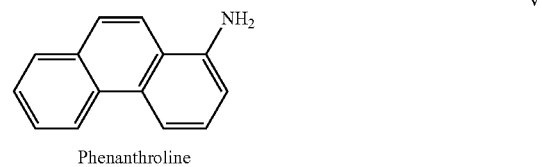

Phenanthroline

V

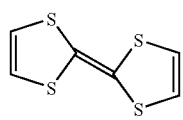
1,3-Dithiole,
2-(1,3-dithiol-2-ylidene)-
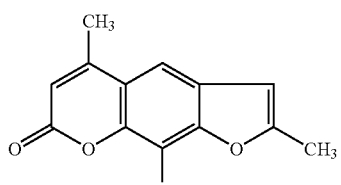
Trimethylpsoralene
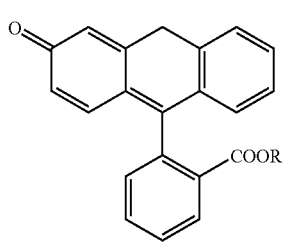
Fluorescein derivative
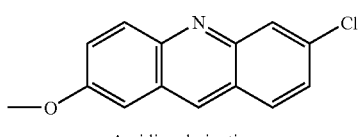
Acridine derivative
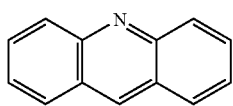
Acradine
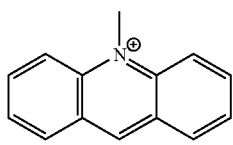
Acradinium
Pyrene
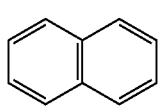
Napthalene
VI
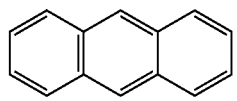
Antracene
VII
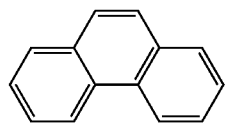
Phenanthrane
VIII
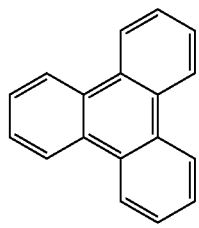
Triphenylene
IX
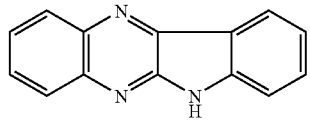
6H-Indolo[2,3-b]quinoxaline
X
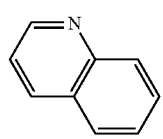
Quinoline
XI
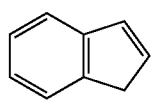
1H-Indene
XII
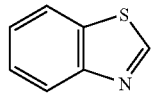
Benzothiazole
XIII
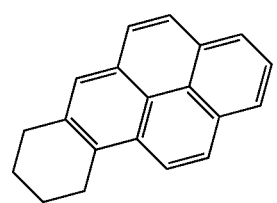
7,8,9,10-Tetrahydrobenzo[a]pyrene
XIV
XV
XVI
XVII
XIX
XX
XXI
XXII

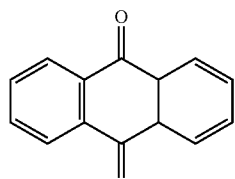

9,10-Anthracenedione

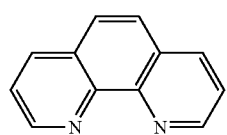

1,10-Phenanthroline

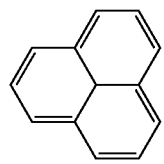

9bH-Phenalene

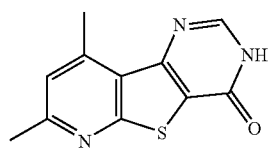

Pyrido[3′,2′:4,5]thieno[3,2-d]pyrimidin-4(1H)-one, 7,9-dimethyl-

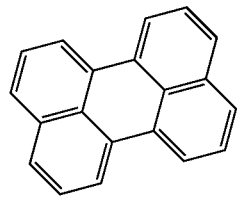

Perylene

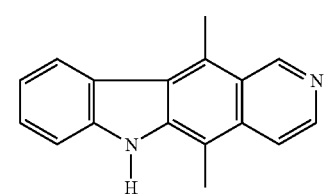

6H-Pyrido[4,3-b]carbazole, 5,11-dimethyl-

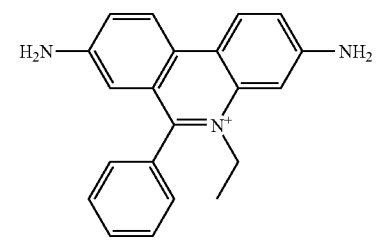

Phenanthridinium, 3,8-diamino-5-ethyl-6-phenyl-

XXIII

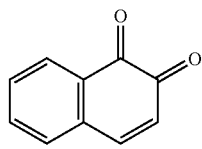

1,2-Naphthalenedione

XXIV

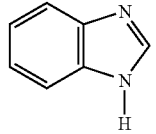

1H-Benzimidazole

XXV

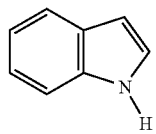

1H-Indole

XXVI

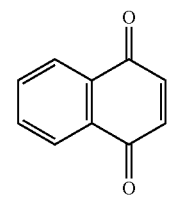

1,4-Naphthalenedione

XXVII

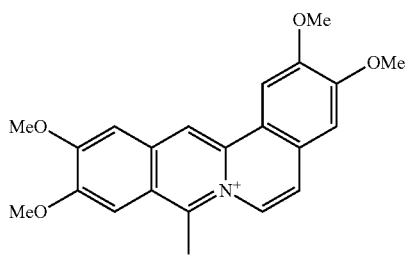

Dibenzo[a,g]quinolizinium, 2,3,10,11-tetramethoxy-8-methyl-

XXVIII

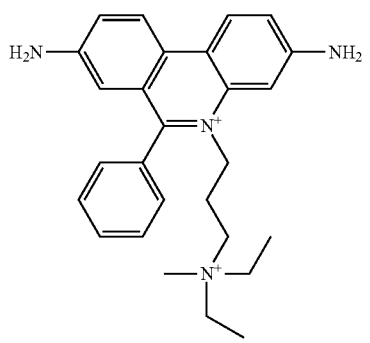

Phenanthridinium, 3,8-diamino-5-[3-(diethylmethylammonio)propyl]-6-phenyl-

XXIX

XXX

XXXI

XXXII

XXXIII

XXXIV

XXXV

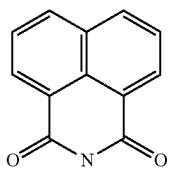

1H-Benz[de]isoquinoline-
1,3(2H)-dione

XXXVI

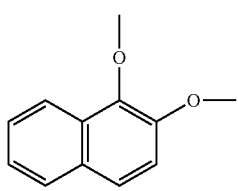

Naphthalene, 1,2-dimethoxy-

XXXVII

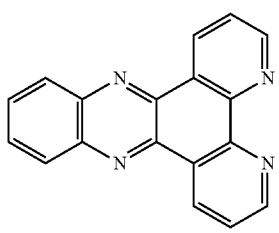

Dipyrido[3,2-a:2′,3′-c]phenazine

XXXVIII

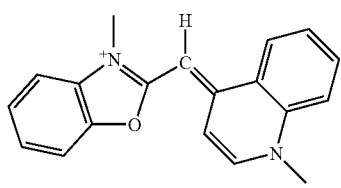

Quinolinium, 4-[(3-ethyl-2(3H)-
benzoxazolylidene)methyl]-1-methyl-

XXXIX

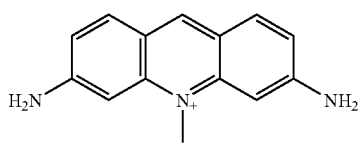

Acridine, 6-amino-3,10-
dihydro-3-imino-10-methyl-

XL

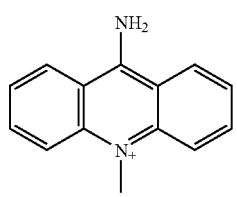

Acridinium, 9-amino-10-methyl-

XLI

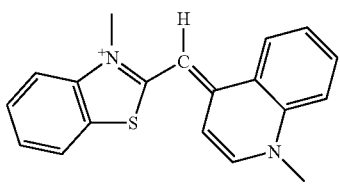

Quinolinium, 1-methyl-4-
[(3-methyl-2(3H)-benzothiazolylidene)methyl]-

XLII

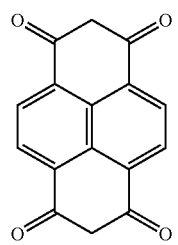

1,3,6,8(2H,7H)-
Pyrenetetrone

XLIII

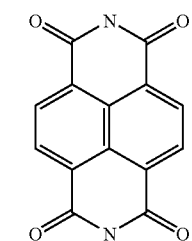

Benzo[1mn][3,8]phenanthroline-
1,3,6,8(2H,7H)-tetrone

XLIV

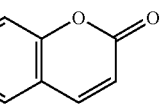

2H-1-Benzopyran-2-one

XLV

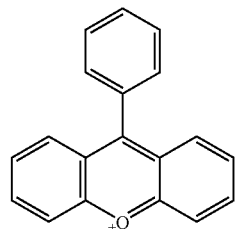

Xanthylium, 9-phenyl-

XLVI

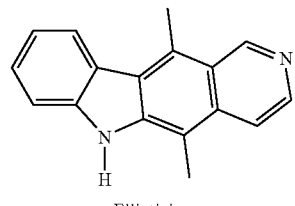

Ellipticine

XLVII

XLVIII

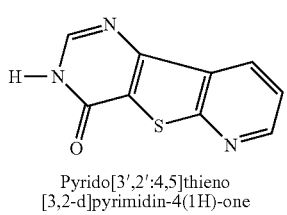

Pyrido[3',2':4,5]thieno
[3,2-d]pyrimidin-4(1H)-one

XLIX

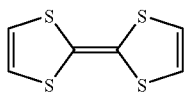

Fulvalene

L

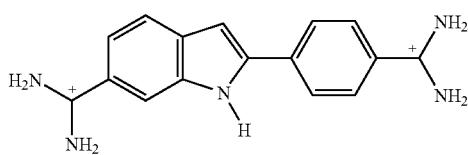

DAPI

LI

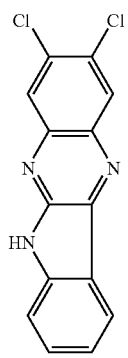

LII

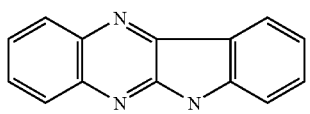

And optionally, but not so preferable derivatives thereof.

Even more preferably the intercalator may be selected from the group of intercalators consisting of the intercalator structures above numbered V, XII, XIV, XV, XVII, XXIII, XXVI, XXVIII, XLVII, LI and LII as well as derivatives thereof, preferably from the group of intercalators consisting of the intercalator structures above numbered V, XII, XIV, XV, XVII, XXIII, XXVI, XXVIII, XLVII, LI and LII.

Most preferably the intercalator is selected from the group of intercalator structures above numbered XII, XIV, XVII, XXIII, LI as well as derivatives thereof, preferably from the group of intercalator structures above numbered XII, XIV, XVII, XXIII and LI.

The above list of examples is not to be understood as limiting in any way, but only as to provide examples of possible structures of hydrophobic molecules comprising an intercalator. In addition, the substitution of one or more chemical groups on each intercalator to obtain modified structures is also included in the present invention.

In one embodiment of the invention the intercalator may be any of the intercalators described in international patent application WO03/052132 in the section "intercalator" on p. 46, l. 10-p. 54, l. 13.

Minor Groove Binders

In one specific embodiment the hydrophobic molecule may be a minor groove binder, although it is preferred in other embodiments of the invention that the hydrophobic molecule is not a minor groove binder. It is preferred that the minor groove binder is hydrophobic having a log P value at indicated herein above.

Minor groove binders are a potent class of oligonucleotide or oligonucleotide analogue modifiers that bind to duplex DNA in the minor groove. Minor groove binders are long, flat molecules that can adopt a "crescent shape" that fits tightly into the deep, narrow space formed between the two phosphate-sugar backbones in the double helix, called the minor groove, displace water molecules and form close atomic contacts in the mino groove. They are stabilized in the minor groove by hydrogen bonds and/or hydrophobic interactions.

In the prior art section above it is explained in brief how Kutyavin and co-workers conjugated a MGB molecule to the 3'-end of the probe and used it in at 5'-nuclease PCR assay and non-nuclease dependent assay where the MGB is attached to the 5'-end of the probe. Neither of these publications discusses the lowering of the background signal by hydrophobic interactions in the unbound probe. Hence even though MGBs are well known in art, it has not been known prior to the present invention that the hydrophobicity of said MGBs in the right combination and position within an oligonucleotide analogue could be used to improve the signal-to-noise ratio by increasing the interaction between the two parts of a signalling pair.

It is therefore a preferred embodiment of the present invention to provide an oligonucleotide analogue that comprise at least one minor groove binder and a signalling pair, where said minor groove binder is positioned in one half of said oligonucleotide or oligonucleotide analogue and when unbound to a target sequence have hydrophobic interactions with a moiety of the second half of said oligonucleotide analogue. In particular, it is preferred that a hydrophobic nucleotide comprising a minor groove binder is not positioned as the first nucleotide or nucleotide analogue at the 5' end or the 3' end, but rather internal in the oligonucleotide analogue.

It is an even more preferred embodiment of the present invention to provide an oligonucleotide analogue that comprise a signalling pair and at least one minor groove binder positioned in one half of said oligonucleotide analogue and another hydrophobic molecule according to the present invention in the other half of said oligonucleotide analogue, so that when said oligonucleotide analogue is unbound to a target sequence said minor groove binder and said hydrophobic molecule have hydrophobic interactions with each other resulting in a better interaction of the two parts in said signalling pair.

Backbone Monomer Unit

The backbone monomer unit of a nucleotide or a nucleotide analogue according to the present invention is the part of the nucleotide, which is involved in incorporation into the backbone of a nucleic acid or a nucleic acid analogue. The backbone monomer unit (X) is preferably covalently linked to a linker (Y), which is covalently linked to the hydrophobic molecule. Any suitable backbone monomer unit may be employed for incorporating hydrophobic nucleotides into the oligonucleotide analogues according to the present invention. Any sort of linker linking said backbone monomer unit and said hydrophobic molecule could also be employed. In addition, the backbone monomer unit may comprise one or more leaving groups, protecting groups and/or reactive groups, which may be removed or changed in any way during synthesis or subsequent to synthesis of an oligonucleotide or oligonucleotide analogue comprising said backbone monomer unit.

The backbone monomer unit may be any suitable backbone monomer unit. In one embodiment of the present invention, the backbone monomer unit may for example be selected from the group consisting of the backbone monomer units of DNA, RNA, PNA, HNA, MNA, ANA, LNA, CNA, CeNA, TNA, (2'-NH)-TNA, (3'-NH)-TNA, α-L-Ribo-LNA, α-L-Xylo-LNA, β-D-Xylo-LNA, α-D-Ribo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo[4.3.0]-DNA, Bicyclo[3.2.1]-DNA, Bicyclo[4.3.0]amide-DNA, β-D-Ribopyranosyl-NA, α-L-Lyxopyranosyl-NA, 2'-R-RNA, α-L-RNA or α-D-RNA, β-D-RNA and mixtures thereof and hybrids thereof, as well as phosphorous atom modifications thereof, such as but not limited to phosphorothioates, methyl pholates, phosphoramidiates, phosphorodithiates, phosphoroselenoates, phosphotriesters and phosphoboranoates. In addition non-phosphorous containing compounds may be used for linking to nucleotides such as but not limited to methyliminomethyl, form acetate, thioformacetate and linking groups comprising amides. In particular nucleic acids and nucleic acid analogues may comprise one or more hydrophobic nucleotides according to the present invention.

Below is depicted a range of different backbone monomer units of nucleotides and nucleotide analogues useful with the present invention, and how they are connected to the nucleobases via linkers that are attached at one or two positions of the backbone monomer unit:

DNA

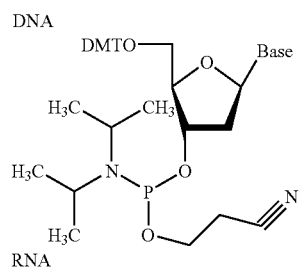

RNA

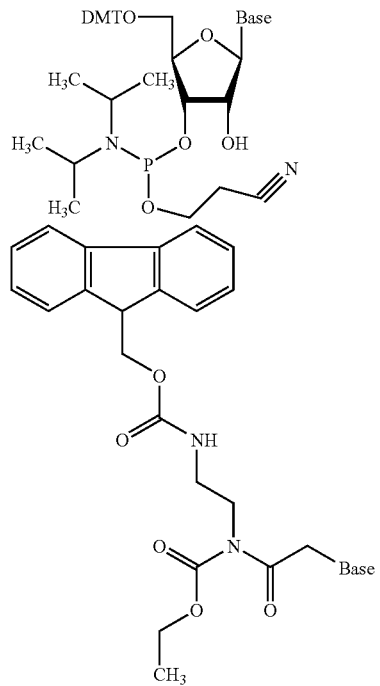

Examples of oligomers of DNA, RNA & PNA

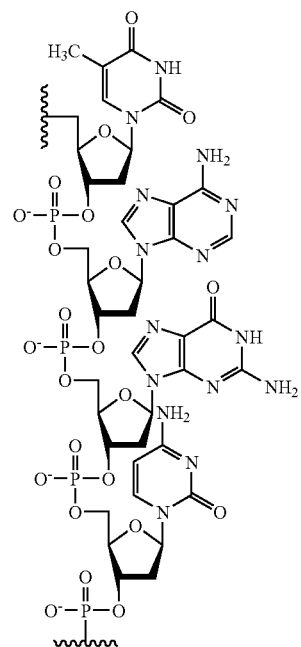

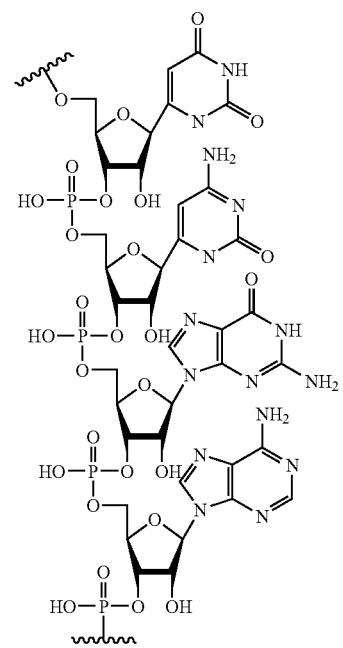

51
-continued
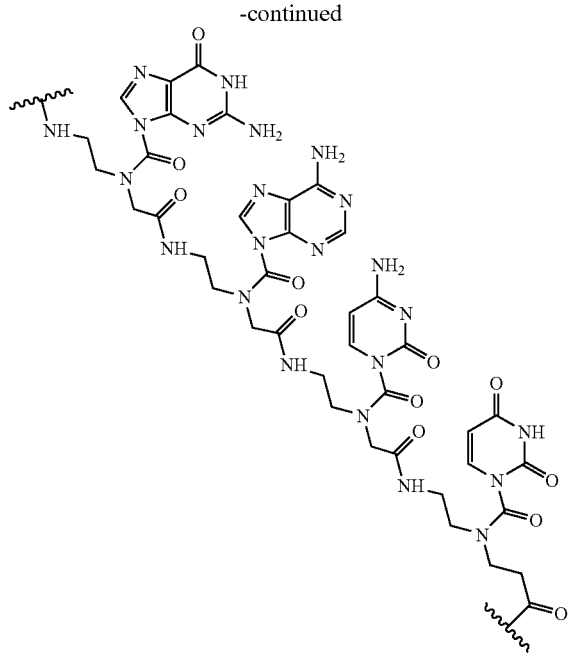
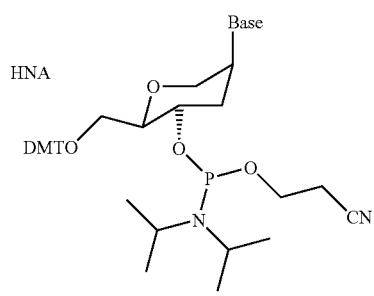
HNA
Ref. Van Aerschot, A. et al. *Angew. Chem. Int. Ed.. Engl.*, 1995, 34, 1338-1339.
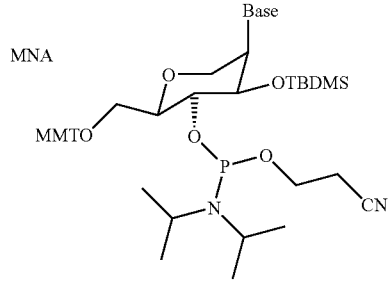
MNA
Ref. Hossain N. et al. *J. Org. Chem.*, 1998, 63, 1574-1582.
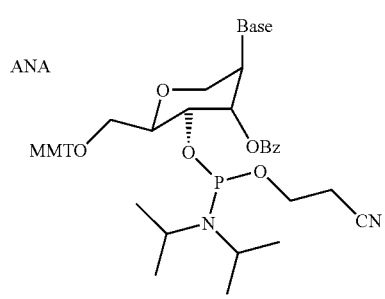
ANA
Ref. Allart, B. et al. *Chem. Eur. J.*, 1999, 5, 2424-2431.
52
-continued
LNA
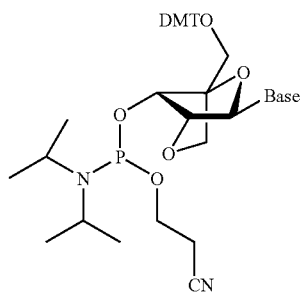
Ref. Singh, S. K. et al. *Chem. Commun.*, 1998, 455-456; Koshkin, A. A. et al. *Tetrahedron*, 1998, 54, 3607-3630; Obika, S. et al. *Tetrahedron lett.*, 1997, 38, 8735-8738.
Examples of oligomers of some analogues
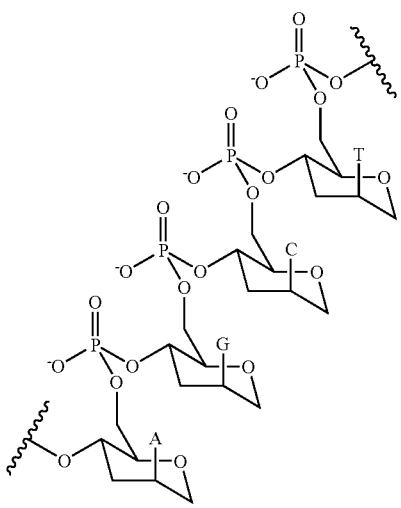
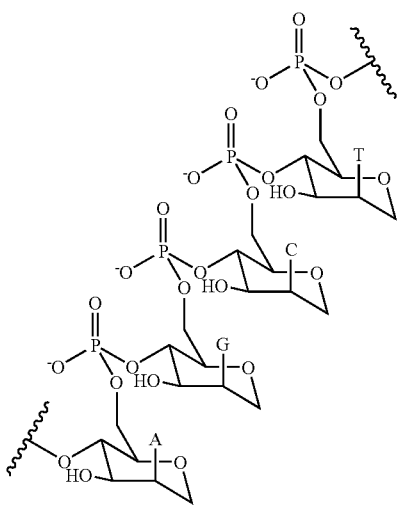

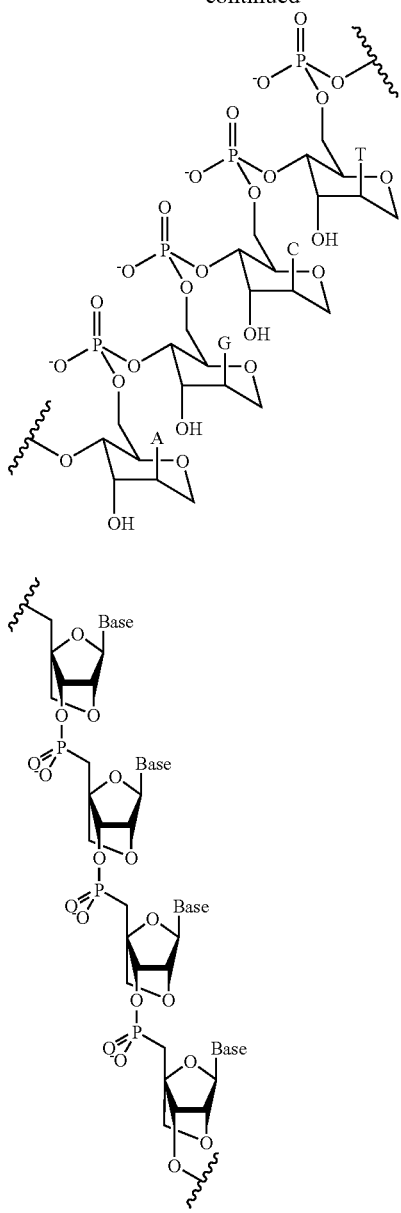
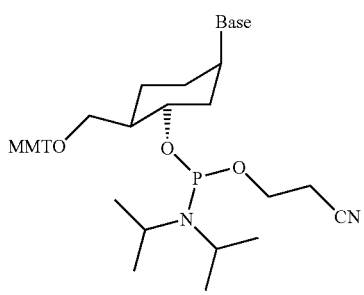
Cyclohexanyl-NA (CNA)
Ref: Maurinsh, Y.;et al. *Chem. Bur. J.*, 1999, 2139-2150.
Cyclohexanyl-NA (CeNA)
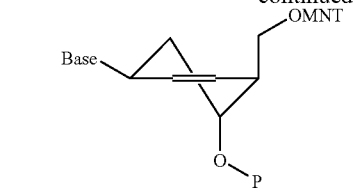
Ref: Wang, J.; et al. *J. Am. Chem. Soc*, 2000, 8595-8602.
(2'-NH)-TNA 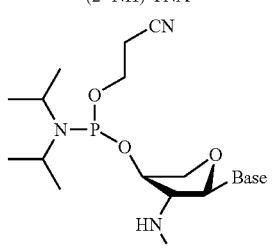  (3'-NH)-TNA 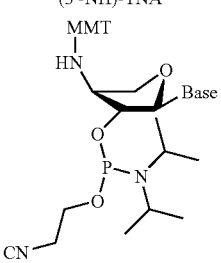
Ref.: Wu, X. et al., *Org. Lett.*, 2002, 4, 1279-1282
TNA
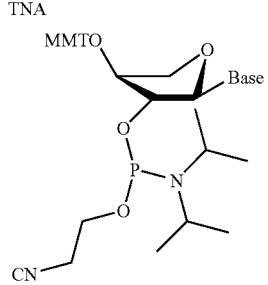
Ref.: Wu, X. et al., *Org. Lett.*, 2002, 4, 1279-1282
Examples of oligomers of some analogues
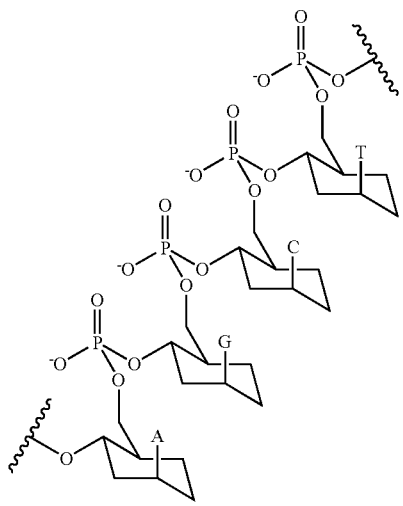

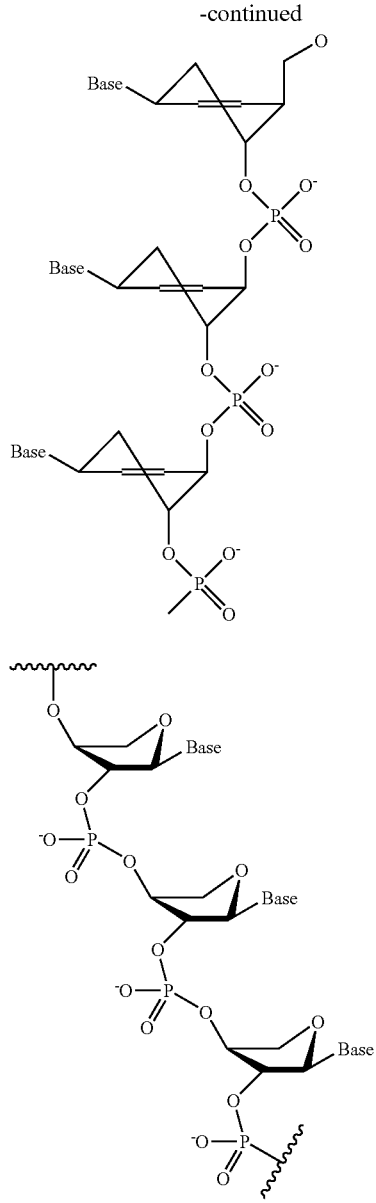
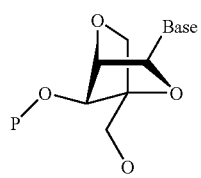
α-L-Ribo-LNA
Ref: Rajwanshi, V. K. et al. *Chem. Commun.*, 1999, 1395-1396.
α-L-Xylo-LNA
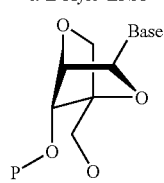
Ref: Rajwanshi, V. K. et al. *Angew. Chem. Int. Ed.*, 2000, 1656-1659.
β-D-Xylo-LNA
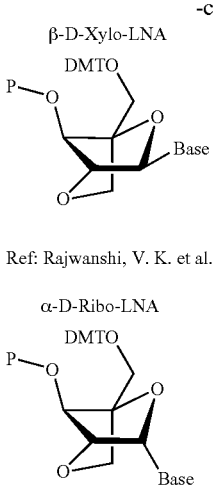
Ref: Rajwanshi, V. K. et al. *Chem. Commun.*, 1999, 1395-1396.
α-D-Ribo-LNA
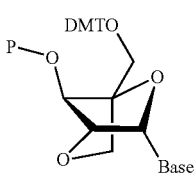
Ref: Rajwanshi, V. K et al. *Angew. Chem. Int. Ed.*, 2000, 1656-1659.
[3.2.1]-LNA
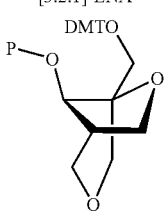
Ref: Wang, G.; et al. *Tetrahedron*, 1999, 7707-2724.
Section of a nucleic acid of the respective analogues
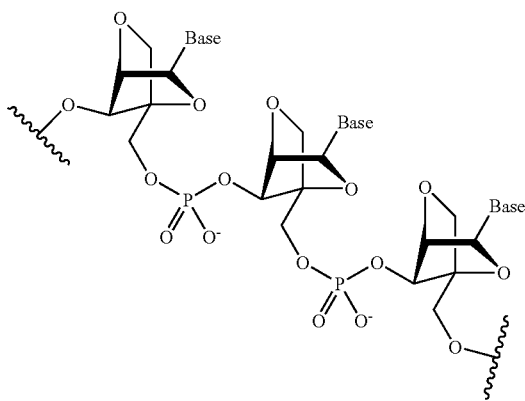
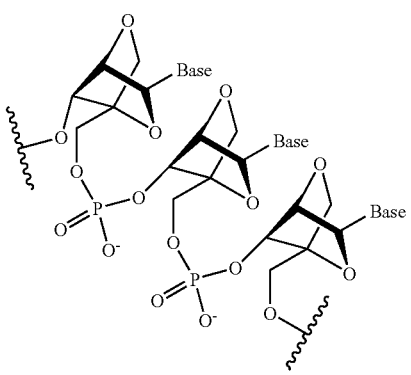

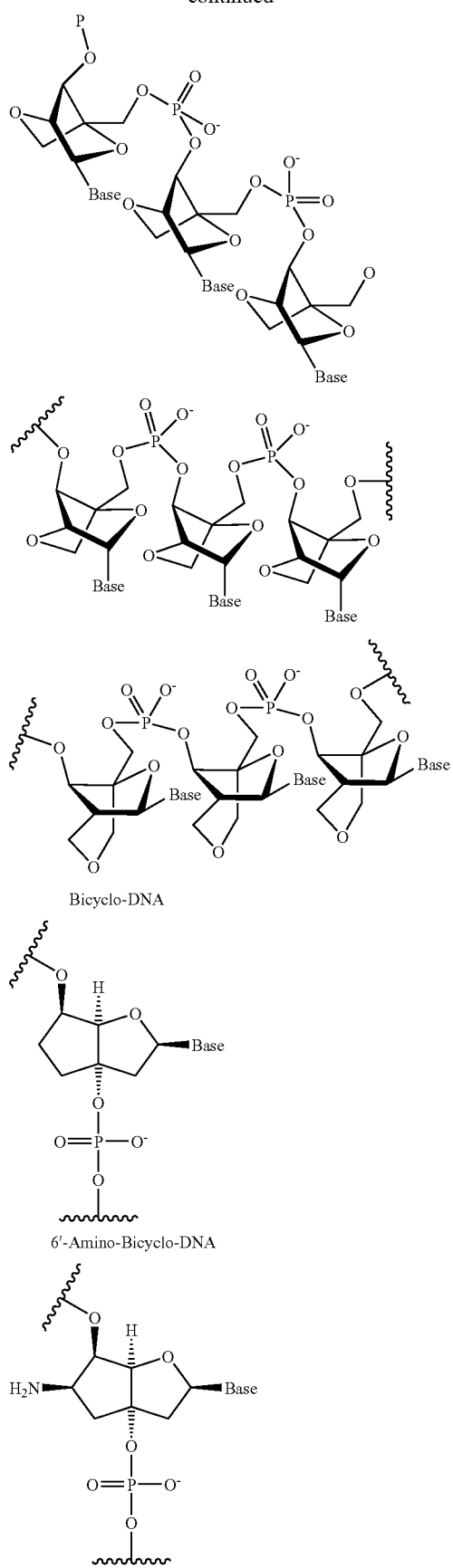
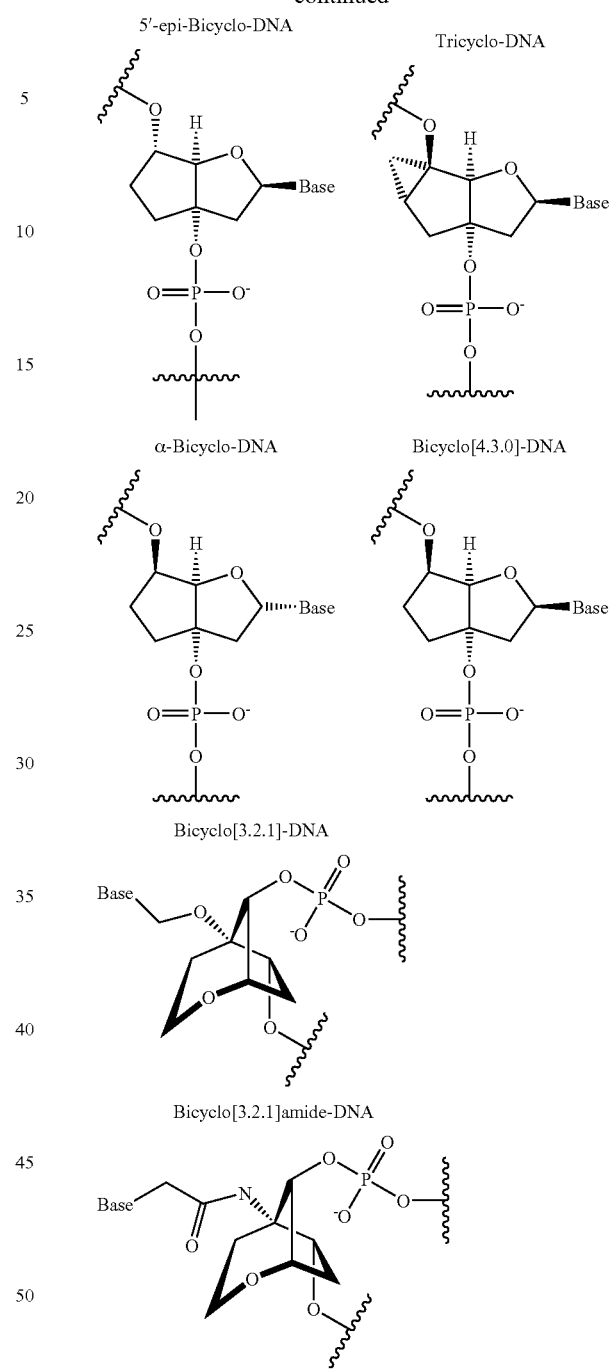
Ref: All of the Bicyclo-DNAs are reviewed in Leumann, C.J., *Bioorg. Med. Chem.*, 2002, 841-854.
β-D-Ribopyranosyl-NA
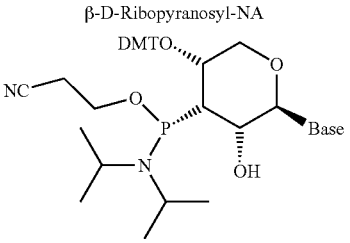
Ref: Reck, F. et al., *Org. Lett.* 1999, 1, 1531

-continued
α-L-Lyxopyranosyl-NA
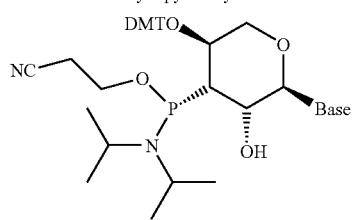
Ref: Reck, F. et al., *Org. Lett.* 1999, 1, 1531
2′-R-RNA
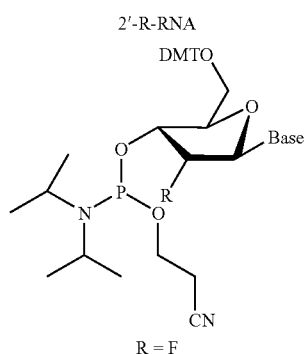
R = F
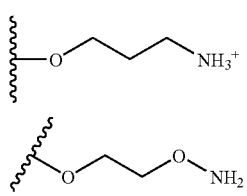
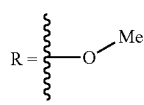
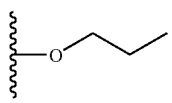
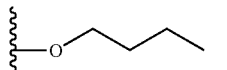
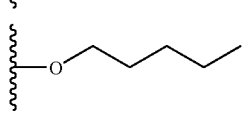
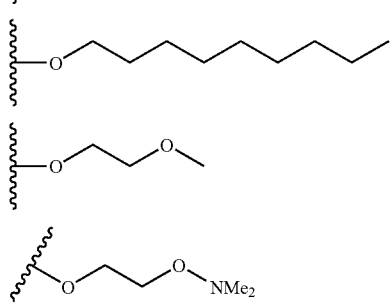
Ref: Reviewed by Manoharan, M. Biochim. *BioPhys. Acta*, 1999, 117-130.
-continued
General structure of 2′-modified oligomers
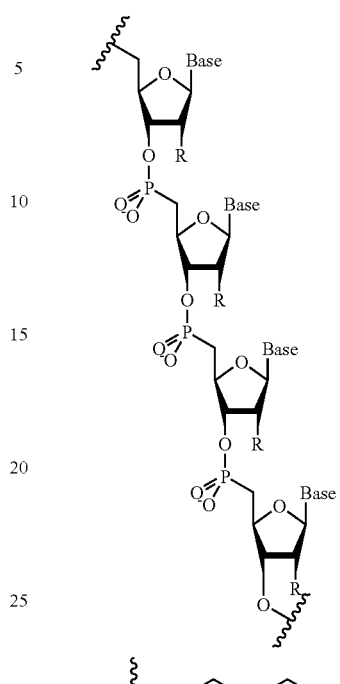
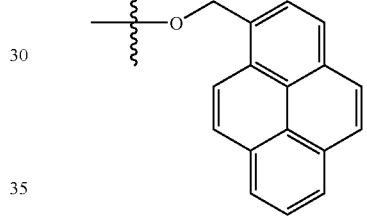
Ref: Yamana, K. et al., *Tetrahedron Lett.*, 1991, 6347-6350.
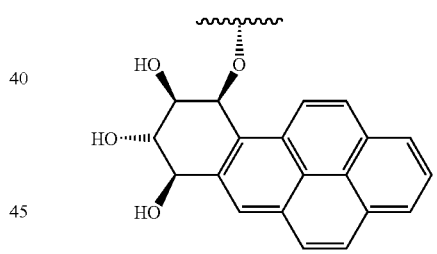
Ref: Sayer, J. et al., *J. Org. Chem.*, 1991, 56, 20-29.
Examples of modifications that, to our knowledge, are not synthesised or published yet:
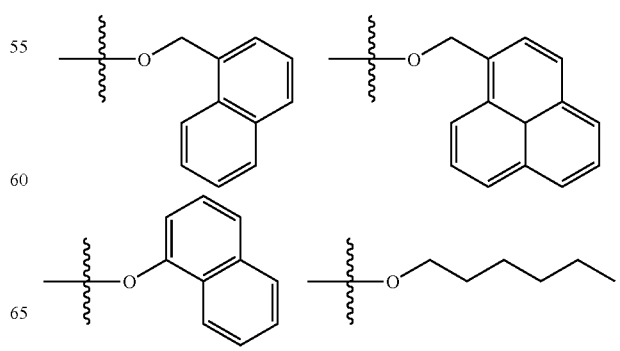

-continued

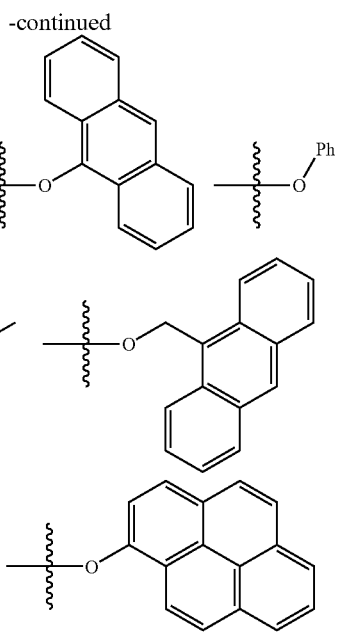

Some of the backbone monomer units shown above are already coupled to hydrophobic molecules according to the present invention, while others can have hydrophobic molecules linked to the nucleotides. The hydrophobic molecules can be connected at any available atom, such as at an atom of the nucleobase, the backbone or the linker linking said nucleobase and backbone if present. The hydrophobic molecules could also replace the nucleobases or be coupled to its own backbone monomer unit of any sort.

In a preferred embodiment the backbone monomer unit does not comprise a nucleobase, such as a naturally occurring nucleobase. It is also preferred that the linker does not comprise a nucleobase, such as a naturally occurring nucleobase.

When the backbone monomer unit comprises a ribose group it is in one embodiment preferred that the hydrophobic molecule is covalently linked to said ribose group via a linker. In this embodiment, the hydrophobic molecules is thus preferably not covalently linked to a phosphate group of the backbone via a linker (Y).

The backbone monomer unit of LNA (locked nucleic acid) is a sterically restricted DNA backbone monomer unit, which comprises an intramolecular bridge that restricts the usual conformational freedom of a DNA backbone monomer unit. LNA may be any LNA molecule as described in WO 99/14226 (Exiqon), preferably, LNA is selected from the molecules depicted in the abstract of WO 99/14226. Preferred LNA according to the present invention comprises a methyl linker connecting the 2'-O position to the 4'-C position, however other LNA's such as LNA's wherein the 2' oxy atom is replaced by either nitrogen or sulphur are also comprised within the present invention.

The preferred backbone monomer units of nucleotides comprising hydrophobic molecules according to the present invention are backbone monomer units that allows said hydrophobic molecule to interact with its target nucleic acid.

In one preferred embodiment of the present invention the backbone monomer unit is selected from the group consisting of acyclic backbone monomer units. Acyclic is meant to cover any backbone monomer unit, which does not comprise a ring structure, for example the backbone monomer unit preferably does not comprise a ribose or a deoxyribose group.

It is thus preferred that the backbone monomer unit of an hydrophobic nucleotide according to the present invention may be selected from the group consisting of backbone monomer units comprising at least one chemical group selected from the group consisting of trivalent and pentavalent phosphorous atom such as a pentavalent phosphorous atom. More preferably the phosphate atom of the backbone monomer unit according to the present invention may be selected from the group consisting of backbone monomer units comprising at least one chemical group selected from the group consisting of, phosphoester, phosphodiester, phosphoramidate and phosphoramidit groups.

In particular it is preferred that the backbone monomer unit of a hydrophobic nucleotide according to the present invention is selected from the group consisting of acyclic backbone monomer units comprising at least one chemical group selected from the group consisting of phosphate, phosphoester, phosphodiester, phosphoramidate and phosphoramidit groups.

Preferably the backbone monomer unit is capable of being incorporated into a phosphate backbone of a nucleic acid or nucleic acid analogue in a manner so that at the most 5, for example at the most 4 atoms are separating the phosphor atom of the backbone monomer unit and the nearest neighbouring phosphor atom, more preferably 5, such as at the most 4 atoms are separating the phosphor atom of the backbone monomer unit and the nearest neighbouring phosphor atom, in both cases not including the phosphor atoms themselves.

In a particularly preferred embodiment of the present invention the hydrophobic nucleotide comprises a backbone monomer unit that comprises a phosphoramidit and more preferably the backbone monomer unit comprises a trivalent phosphoramidit or a pentavalent.

Suitable trivalent phosphoramidits are trivalent or pentavalent phosphoramidits that may be incorporated into the backbone of a nucleic acid and/or a nucleic acid analogue. Usually, the amidit group per se may not be incorporated into the backbone of a nucleic acid, but rather the amidit group or part of the amidit group may serve as a leaving group and/or protecting group. However, it is preferred that the backbone monomer unit comprises a phosphoramidit group, because such a group may facilitate the incorporation of the backbone monomer unit into a nucleic acid backbone.

In one embodiment of the present invention, the backbone monomer unit may be any of the backbone monomer units described in international patent application WO03/052132 in the section "Backbone monomer unit" on p. 24, l. 27-p. 43, l. 14.

Linker

The linker of a hydrophobic nucleotide according to the present invention is a moiety connecting the hydrophobic molecule and the backbone monomer of said hydrophobic nucleotide, preferably covalently linking said hydrophobic molecule and the backbone monomer unit. The linker may comprise one or more atom(s) or bond(s) between atoms.

By the definitions of backbone and hydrophobic molecules defined herein above, the linker is the shortest path linking the backbone and the hydrophobic molecules. If the hydrophobic molecules is linked directly to the backbone, the linker is a bond.

The linker usually consists of a chain of atoms or a branched chain of atoms. Chains can be saturated as well as unsaturated. The linker may also be a ring structure with or without conjugated bonds.

For example the linker may comprise a chain of m atoms selected from the group consisting of C, O, S, N. P, Se, Si, Ge, Sn and Pb, preferably from the group consisting of C, O, S, N and P, even more preferably they are C, wherein one end of the chain is connected to the hydrophobic molecule and the other end of the chain is connected to the backbone monomer unit.

In some embodiments the total length of the linker and the hydrophobic molecules of the hydrophobic nucleotides according to the present invention preferably is between 8 and 13 Å (see herein below). Accordingly, m should be selected dependent on the size of the hydrophobic molecules of the specific hydrophobic nucleotide.

I.e. m should be relatively large, when the intercalator is small and m should be relatively small when the intercalator is large. For most purposes however m will be an integer from 1 to 7, such as from 1-6, such as from 1-5, such as from 1-4. As described above the linker may be an unsaturated chain or another system involving conjugated bonds. For example the linker may comprise cyclic conjugated structures. Preferably, m is from 1 to 4 when the linker is a saturated chain.

When the hydrophobic molecules is pyrene, m is preferably an integer from 1 to 7, such as from 1-6, such as from 1-5, such as from 1-4, more preferably from 1 to 4, even more preferably from 1 to 3, most preferably m is 2 or 3.

When the intercalator has the structure

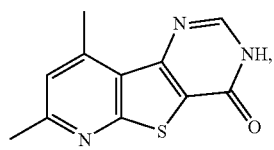

m is preferably from 2 to 6, more preferably 2.

In one embodiment the linker is an azaalkyl, oxaalkyl, thiaalkyl or alkyl chain. For example the linker may be an alkyl chain substituted with one or more selected from the group consisting C, H, O, S, N, P, Se, Si, Ge, Sn and Pb, preferably selected from the group consisting of C, H, O, S, N and P. In a preferred embodiment the linker consists of an unbranched alkyl chain, wherein one end of the chain is connected to the hydrophobic molecules and the other end of the chain is connected to the backbone monomer unit and wherein each C is substituted with 2H. More preferably, said unbranched alkyl chain is from 1 to 5 atoms long, such as from 1 to 4 atoms long, such as from 1 to 3 atoms long, such as from 2 to 3 atoms long.

In another embodiment the linker consists of from 1-6 C atoms, from 0-3 of each of the following atoms O, S, N. More preferably the linker consists of from 1-6 C atoms and from 0-1 of each of the atoms O, S, N.

In a preferred embodiment the linker consists of a chain of C, O, S and N atoms, optionally substituted. Preferably said chain should consist of at the most 3 atoms, thus comprising from 0 to 3 atoms selected individually from C, O, S, N, optionally substituted.

In a preferred embodiment the linker consists of a chain of C, N, S and O atoms, wherein one end of the chain is connected to the intercalator and the other end of the chain is connected to the backbone monomer unit.

Preferably such a chain comprise one of the linkers shown below, most preferably the linker consist of one of the molecule shown below:

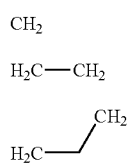

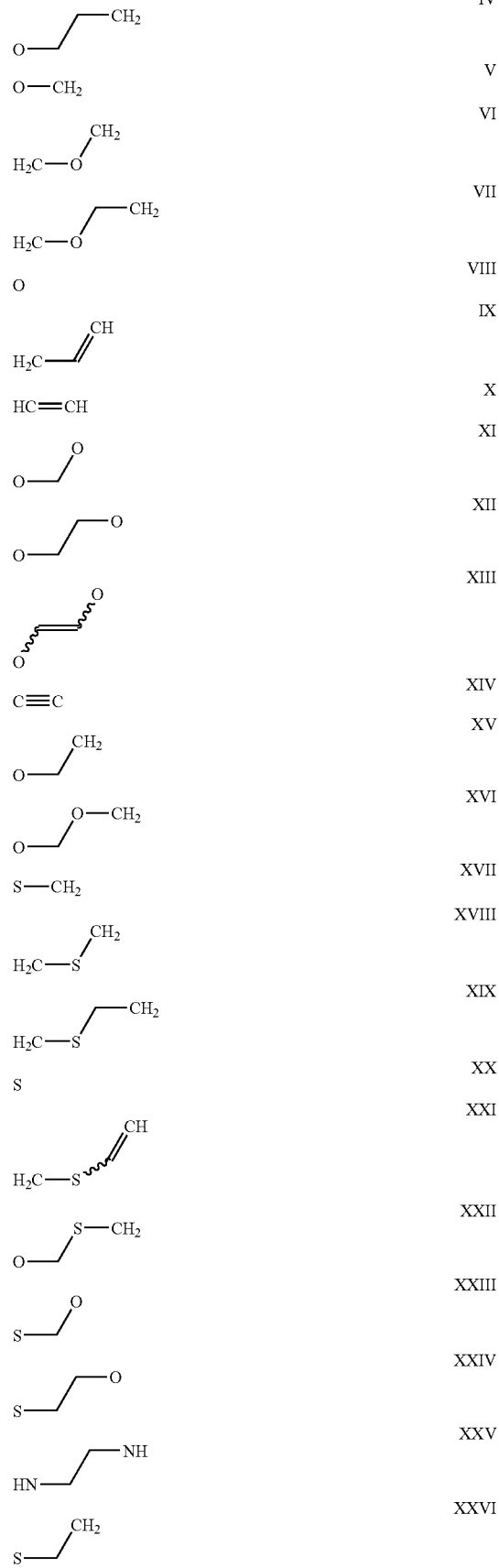

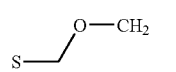
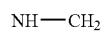
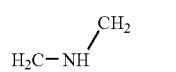
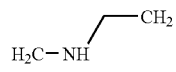
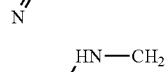
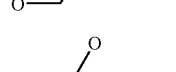
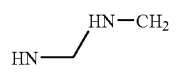
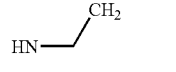
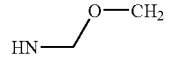
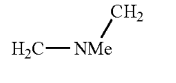
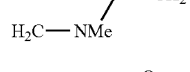
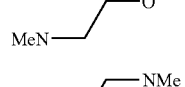
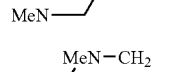
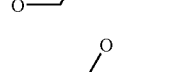
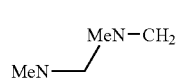
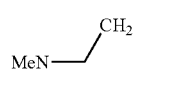
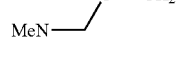

| | | |
|---|---|---|
| XXVII | | L |
| | 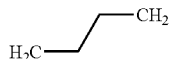 | |
| XXVIII | | LI |
| XXIX | 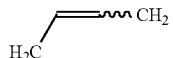 | |
| XXX | | LII |
| | 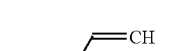 | |
| XXXI | | |

In a preferred embodiment the chain comprise one of the linkers shown below, more preferably the linker consist of one of the molecule shown below:

| | | |
|---|---|---|
| XXXIII | 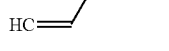 | II |
| XXXIV | | III |
| |  | |
| XXXV | | VI |
| | 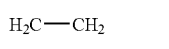 | |
| XXXVI | | VII |
| |  | |
| XXXVII | | IX |
| | 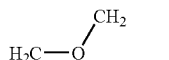 | |
| XXXVIII | | L |
| | 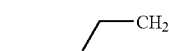 | |
| XXXIX | | LI |
| XL |  | |
| XLI | | LII |
| | 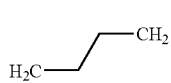 | |
| XLII | | |

In a more preferred embodiment the chain comprise one of the linkers shown below, more preferably the linker consist of one of the molecule shown below:

| | | |
|---|---|---|
| XLIII | | |
| XLIV |  | II |
| XLV | | III |
| | 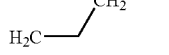 | |
| XLVI | | VI |
| | 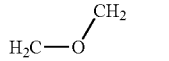 | |
| XLVII | | VII |
| | 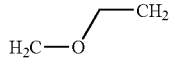 | |
| XLVIII | | IX |
| | 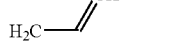 | |
| XLIX | | |

The linker constitutes Y in the formula for the hydrophobic nucleotide X—Y-Q, as defined above, and hence X and Q are not part of the linker.

In one embodiment of the invention the linker may be any of the linkers described in WO03/052132 in the section "Linker" on p. 54, I. 15 to p. 58, I. 7.

Label

In the present context, the term "label" thus means a group that is detectable either by itself or as a part of a detection series. Examples of functional parts of reporter groups are biotin, digoxigenin, fluorescent groups (groups that are able to absorb electromagnetic radiation, e.g. light or X-rays, of a certain wavelength, and which subsequently reemits the energy absorbed as radiation of longer wavelength; illustrative examples are dansyl (5-dimethylamino)-1-naphthalene-sulfonyl), DOXYL (N-oxyl-4,4-dimethyloxazolidine), PROXYL (N-oxyl-2,2,5,5-tetramethylpyrrolidine), TEMPO (N-oxyl-2,2,6,6-tetra-methylpiperidine), dinitrophenyl, acridines, coumarins, Cy3 and Cy5 (trademarks for Biological Detection Systems, Inc.), erytrosine, coumaric acid, umbelliferone, Texas Red, rhodamine, tetramethyl rhodamine, Rox, 7-nitrobenzo-2-oxa-1-diazole (NBD), pyrene, fluorescein, "quantum dots", Europium, Ruthenium, Samarium, and other rare earth metals, radioisotopic labels, chemiluminescence labels (labels that are detectable via the emission of light during a chemical reaction), spin labels (a free radical (e.g. substituted organic nitroxides) or other paramagnetic probes (e.g. $Cu^{2+}$, $Mg^{2+}$) bound to a biological molecule being detectable by the use of electron spin resonance spectroscopy), enzymes (such as peroxidases, alkaline phosphatases, β-galactosidases, and glycose oxidases), antigens, antibodies, haptens (groups which are able to combine with an antibody, but which cannot initiate an immune response by themselves, such as peptides and steroid hormones), carrier systems for cell membrane penetration such as: fatty acid residues, steroid moieties cholesteryl, vitamin A, vitamin D, vitamin E, folic acid peptides for specific receptors, groups for mediating endocytose, epidermal growth factor (EGF), bradykinin, and platelet derived growth factor (PDGF). Especially interesting examples are biotin, fluorescein, Texas Red, rhodamine, dinitrophenyl, digoxigenin, Ruthenium, Europium, Cy5, Cy3, etc.

Signalling Pair

Signalling pairs of the present invention is defined as two parts that in combination are able to make a measurable change, depending on the physical distance, orientation and/or interaction with each other. Preferably a signalling pair consists of two part system that in combination are capable of generating a detectable signal, wherein there is a change in said detectable signal depending on the physical distance between the parts of the pair.

According to the present invention the part of the signalling pair are not identical to the hydrophobic nucleotide of the oligonucleotide analogue. Thus, it is preferred that the parts of the signalling pair, when inserted into the oligonucleotide analogue of the invention also are not part of a structure identical to the hydrophobic nucleotide.

In a preferred embodiment of the present invention at least one part of the signalling pair, more preferably none of parts of the signalling pair are identical to the intercalator pseudonucleotide Y described in Example 24, p. 199 or to the intercalator pseudonucleotide Y described in Example 14 on p. 184 in international patent application WO03/052132. It is also preferred that the parts of the signalling pair are not part of a structure identical to the intercalator pseudonucleotide Y described in Example 24, p. 199 or to the intercalator pseudonucleotide Y described in Example 14 on p. 184 in international patent application WO03/052132 when inserted into the oligonucleotide analogue.

The signal generated can be of any nature, for example the signal can be a change in fluorescence or electrical resistance of the system. In a preferred embodiment the signalling pair is capable of a change in fluorescence depending on the distance between the parts of the pair. The signalling pair of the present invention will make a change in signal, dependent on whether the probe wherein said signalling pair is attached is hybridised to a target sequence or not. Thus it is preferred that the signalling pair is positioned within the oligonucleotide analogue in a manner, so that the distance between the parts of the signalling pair will increase upon hydridisation of the oligonucleotide analogue to a target sequence.

Preferably a signalling pair according to the present invention is consisting of two parts being positioned in opposite halves of an oligonucleotide analogue according to the present invention.

It is a more preferred embodiment of the present invention that at least one of the parts of the signalling pair is positioned in one end of an oligonucleotide analogue according to the present invention, while the other part is positioned in the other half of said oligonucleotide analogue.

It is an even more preferred if the two parts of a signalling pair in the present invention are positioned in or close to opposite ends of an oligonucleotide analogue according to the present invention.

Preferably, one part of the signalling pair is positioned within 6, such as within 5, for example within 4, such as within 3, for example within 2, such as at the first nucleotide or nucleotide analogue from the 5' end. In a preferred embodiment the part of the signalling pair is positioned as a dangling end at the 5' end. It is furthermore preferred that said part of the signalling pair is positioned within the 5' half of the oligonucleotide analogue. It is more preferred that said part of the signalling pair is positioned within the 5' third of the oligonucleotide analogue. It is more preferred that said part of the signalling pair is positioned within the 5' fourth of the oligonucleotide analogue. Thus, the preferred maximal distance from the 5' end may be dependent on the length of the oligonucleotide analogue.

Preferably, the other part of the signalling pair is positioned within 6, such as within 5, for example within 4, such as within 3, for example within 2, such as at the first nucleotide or nucleotide analogue from the 3' end. In a preferred embodiment said part of the signalling pair is positioned as a dangling end at the 3' end. It is furthermore preferred that said part of the signalling pair is positioned within the 3' half of the oligonucleotide analogue. It is more preferred that said part of the signalling pair is positioned within the 3' third of the oligonucleotide analogue. It is more preferred that said part of the signalling pair is positioned within the 3' fourth of the oligonucleotide analogue. Thus, the preferred maximal distance from the 3' end may be dependent on the length of the oligonucleotide analogue.

Preferably both parts of the signalling pair are positioned as indicated above.

Spectral properties, such as fluorescence, are preferred for detection of hybridization, for example when carrying out real-time detection of for example quantitative PCR processes. Thus, it is preferred that the signaling pair is capable of generating a change in spectral properties, such as in fluorescence properties depending on the distance between the parts of the pair.

The fluorescent group may be any group capable of fluorescing, for example (but not limited to) the fluorescent group may be selected from the group consisting of fluorescein, FITC, rhodamine, lissamine rhodamine, rhodamine 123, coumarin, CY-2, CY-3, CY 3.5, CY-5, CY 5.5, FAM, VIC, LIZ, NED, PET, Alexa dyes, GFP, YFP, BFP, YO-YO, HEX, JOE, Nano Orange, Nile Red, OliGreen, Oregon Green, Pico green, Radiant Red, Ribo Green, ROX, R-phycoerythrin, SYPRO Orange, SYPRO Red, SYPRO Ruby, TAMRA, Texas Red, XRITC, Propidium iodide, Acridine Orange, ethidium bromide, SYBR Gold, SYBR Green I, and SYBR Green II.

In a preferred embodiment of the present invention, the signalling pair is comprised of two moieties covalently attached to an oligonucleotide analogue comprising additionally at least one hydrophobic molecule, where said signalling pair is capable of forming an intramolecular excimer and/or an intramolecular exciplex and/or an intramolecular FRET complex and/or an intramolecular charge transfer complex.

In particular, they are capable of forming an intramolecular excimer and/or an intramolecular exciplex and/or an intramolecular FRET complex and/or an intramolecular charge transfer complex when they are in close proximity. Parts of a signaling pair are in close proximity, when they are at the most 100 Å apart, preferably at the most 75 Å, more preferably at the most 50 Å, even more preferably at the most 20 Å apart, for example at the most 10 Å apart.

Without being bound by any particular theory it is anticipated that the conformation of the oligonucleotide analogue is dynamic and above mentioned distances may therefore be considered as averages. Similar considerations relates to the other distances mentioned herein.

It is only possible for molecular moieties to form an excimer, an exciplex, a FRET complex or a charge transfer complex if the two molecules are positioned in relation to one another, so that they are able to interact with one another. Hence the signalling pair cannot form an intramolecular excimer, an intramolecular exciplex, FRET complex or a charge transfer complex if there is a molecular moiety separating the two moieties.

Furthermore, it is also contained within the present invention that the oligonucleotide analogue may comprise at least one quencher molecule. A quencher molecule according to the present invention is any molecule that is capable of quenching the fluorescence of a fluorescent group in its vicinity. The quencher may function by absorbing energy from the fluorescent group and dissipating the energy as for example heat. Hence, the signal from the fluorescent group will be reduced or absent. Accordingly, if a fluorescent group and a suitable quencher molecule are placed in close proximity to each other, the fluorescence of the fluorescent group will be quenched.

A quencher is said to be in close proximity to a fluorescent group, when they are at the most 100 Å apart, preferably at the most 75 Å, more preferably at the most 50 Å, even more preferably at the most 20 Å apart, for example at the most 10 Å apart.

In this invention the term FRET also covers a pair consisting of a fluorophore and a quencher. Hence in this invention the term FRET covers two classes of signalling pairs—the fluorophore-quencher pair, where energy is transferred from the fluorophore to the quencher and emitted as non-visible energy like heat and/or vibrational energy and the classical FRET pairs where energy from one moiety is transferred to another moiety and emitted as light with an energy that is lower than the energy transferred from one moiety to the other (longer wavelength).

Examples of quencher molecules include, but are not limited to, DABCYL, DABSYL TAMRA, Methyl red, Black Hole quencher-1, Black Hole quencher-2, ElleQuencher and QSY-7. However, the quencher molecule must generally be selected according to the fluorescent group.

The oligonucleotide analogue according to the present invention may in one embodiment comprise one or more directly or indirectly detectable labels in addition to a signalling pair. One part of the signalling pair can also be made up of more than one moiety, even though it is preferred that a part of a signaling pair only comprises one moiety. A fluorescence-quencher signalling pair can for example be made up of three moieties, were two moieties are dependent of each other so that said moieties in combination makes up one part of the signalling pair and the third moiety makes up the other. The fluorophore part could for example be made up of a shorter wavelength harvester and a longer wavelength emitter as described in US 2000/6037130, another example is labeling pairs detectable by surface enhanced Raman spectroscopy (SERS) as described in WO 2005/019812, where the quencher part is a complex of a surface seeking group and solid surface, but other combinations could also be used.

The parts of the signaling pair are generally covalently attached to the oligonucleotide analogue. The parts of the signalling pair may individually be covalently linked to a backbone monomer unit, any part of a nucleotide and/or nucleotide analogue including for example the backbone monomer unit or the nucleobase. Preferably, the parts of the signalling pair are individually covalently linked to a nucleotide or a nucleotide analogue, for example to a nucleotide. Thus, the parts of the signalling pair may individually be attached to a ribose part of a backbone monomer unit, to a phosphate of a backbone monomer unit or to a nucleobase. The parts of the signalling pair can be incorporated into said nucleotides and/or nucleotide analogues prior to the chemically or enzymatically synthesis, during the synthesis or post synthesis of the oligonucleotide analogues. They may also be coupled using any suitable linker, such as any of the linkers mentioned herein above. The parts of the signalling pair are preferably covalently inserted into an oligonucleotide analogue according to the present invention. Suitable methods will be available to the skilled person.

Fluorescence: Excimer, Exciplex, FRET and Charge Transfer

An excimer is a dimer of compounds, which are associated in an electronic excited state, and which are dissociative in its ground state. When an isolated compound is excited it may loose its excitation or it may associate with another compound of the same kind (which is not excited), whereby an excimer is formed. An excimer emits fluorescence at a wavelength different from monomer fluorescence emission. When the excimer looses its excitation the association is no longer favourable and the two species will dissociate. An exciplex is an excimer like dimer, wherein the two compounds are different.

Intramolecular excimers are formed by two moieties comprised within one molecule, for example 2 polyaromatic groups within the same molecule. Similar intramolecular exciplexes are formed by two moieties comprised within one molecule, for example by 2 different polyaromatic groups.

Fluorescence resonance energy transfer (FRET) is a distance-dependent interaction between the electronic excited states of two dye molecules in which excitation is transferred from a donor molecule to an acceptor molecule without emission of a photon. FRET is dependent on the inverse $6^{th}$ power of the intermolecular distance, making it useful over distances comparable with the dimension of biological macromolecules. Preferably the donor and the acceptor must be in close proximity (typically between 10 to 100 Å, such as between 10 to 75 Å, for example between 10 to 50 Å, such as between 10 to 20 Å) for FRET to occur. Furthermore, the absorption spectrum of the acceptor must overlap with the fluorescence emission spectrum of the donor. It is further preferred that the donor and the acceptor transition dipole orientations must be approximately parallel.

In some of the methods according to the present invention a FRET pair is used where the fluorescence emitted of the first dye is absorbed by the second dye, which emits only in the infra red area. This is called a fluorophore and quencher pair.

Non-FRET fluorophore-quencher pairs have also been described (US 2000/6150097) and covers the quenching of a fluorophore by a quencher where the quencher does not has a significantly large spectral overlap to explain the extent of quenching by the quencher. Such a non-FRET quenching mechanism and pairs are also incorporated into the present invention.

A charge transfer complex is a chemical complex in which there is weak coordination involving the transfer of charge between two intermolecular or intramolecular moieties, called an electron donor and an electron acceptor. Such two moieties can exhibit an observable charge-transfer absorption band during transition. An example is phenoquinone, in which the phenol and quinone molecules are not held together by formal chemical bonds but are associated by transfer of charge between the compounds' aromatic ring systems.

FRET

Fluorescence Resonance Energy Transfer (FRET) has become one of the most popular tools to assay nucleic acids. This is because FRET lends itself to high throughput automation and is quite sensitive, making it the method of choice for sequence and single nucleotide polymorphism (SNP) analysis. In addition, it is highly useful for probing DNA and RNA structures, dynamics and intermolecular interactions.

FRET is a distance-dependent interaction between the electronic excited states of two dye molecules in which excitation is transferred from one moiety (a donor molecule) to another moiety (an acceptor molecule) without emission of a photon. The efficiency of FRET is dependent on the inverse sixth power of the intermolecular separation, making the distance between the donor molecule and the acceptor molecule very important. Thus, FRET is an important technique for investigating a variety of biological phenomena that produce changes in molecular proximity.

The efficiency of the energy transfer is further dependent upon the donor and acceptor molecules orientation, the quantum yield of fluorescence of the donor, the extinction coefficient of the acceptor and the spectral overlap between the emission of the donor and the absorbance of the acceptor.

Preferred fluorophore-quencher signalling pairs according to the present invention include, but are not limited to:

| Fluorescent group | Quencher |
|---|---|
| FAM | TAMRA |
| TET | TAMRA |
| Rhodamine | TAMRA |
| Coumarin | DABCYL |
| EDANS | DABCYL |
| Fluorescein | DABCYL |
| Lucifer Yellow | DABCYL |
| Eosin | DABCYL |
| TAMRA | DABCYL |
| Cy3 | Blackberry quencher 650 |
| TAMRA | Blackberry quencher 650 |
| Texas Red | Blackberry quencher 650 |
| Cy5 | Blackberry quencher 650 |
| Cy5.5 | Blackberry quencher 650 |
| ROX | Blackberry quencher 650 |
| Alexa Fluor 350 | QSY 35 |
| Alexa Fluor 488 | QSY 35 |
| Alexa Fluor 546 | QSY 35 |

-continued

| Fluorescent group | Quencher |
|---|---|
| Alexa Fluor 350 | Dabcyl |
| Alexa Fluor 488 | Dabcyl |
| Alexa Fluor 546 | Dabcyl |
| Alexa Fluor 546 | QSY 7 and QSY 9 |
| Alexa Fluor 488 | QSY 7 and QSY 9 |
| Alexa Fluor 555 | QSY 7 and QSY 9 |
| Alexa Fluor 568 | QSY 7 and QSY 9 |
| Alexa Fluor 568 | QSY 21 |
| Alexa Fluor 594 | QSY 21 |
| Alexa Fluor 647 | QSY 21 |
| Alexa Fluor 350 | BHQ-0 |
| Pacific Blue | BHQ-0 |
| Marina Blue | BHQ-0 |
| Acridine | BHQ-0 |
| Edans | BHQ-1 |
| Coumarin | BHQ-1 |
| Cy2 | BHQ-1 |
| DANSYL | BHQ-1 |
| Alexa 488 | BHQ-1 |
| FAM | BHQ-1 |
| Oregon Green | BHQ-1 |
| Rhodamine Green-X | BHQ-1 |
| TET | BHQ-1 |
| Alexa 532 | BHQ-1 |
| VIC | BHQ-1 |
| HEX | BHQ-1 |
| CALflour Orange 560 | BHQ-1 |
| Alexa 546 | BHQ-2 |
| TAMRA | BHQ-2 |
| Rhodamine Red-X | BHQ-2 |
| CALflour Red 590 | BHQ-2 |
| Cy3.5 | BHQ-2 |
| ROX | BHQ-2 |
| Alexa 568 | BHQ-2 |
| CALflour Red 610 | BHQ-2 |
| Alexa 594 | BHQ-2 |
| CALflour Red 635 | BHQ-2 |
| Pulsar 650 | BHQ-2 |
| Alexa 647 | BHQ-2 |
| Quasar 670 | BHQ-2 |
| Cy5 | BHQ-3 |
| Cy5.5 | BHQ-3 |

Preferred pairs of classical FRET signalling pairs according to the present invention include, but are not limited to:

| Donor | Acceptor |
|---|---|
| Fluorescein | Tetramethylrhodamine |
| IAEDANS | Fluorescein |
| EDANS | DABCYL |
| Fluorescein | Fluorescein |
| BODIPY FL | BODIPY FL |
| Fluorescein | QSY 7 dye |
| Fluorescein | QSY 9 dye |
| Alexa Fluor 350 | Alexa Fluor 488 |
| Alexa Fluor 488 | Alexa Fluor 546 |
| Alexa Fluor 488 | Alexa Fluor 555 |
| Alexa Fluor 488 | Alexa Fluor 568 |
| Alexa Fluor 488 | Alexa Fluor 594 |
| Alexa Fluor 488 | Alexa Fluor 647 |
| Alexa Fluor 546 | Alexa Fluor 568 |
| Alexa Fluor 546 | Alexa Fluor 594 |
| Alexa Fluor 546 | Alexa Fluor 647 |
| Alexa Fluor 555 | Alexa Fluor 594 |
| Alexa Fluor 555 | Alexa Fluor 647 |
| Alexa Fluor 568 | Alexa Fluor 647 |
| Alexa Fluor 594 | Alexa Fluor 647 |

"Black Hole Quencher", "BHQ", "Pulsar", "Quasar", "CALflour Orange" and "CALflour Red" are trademarks of Biosearch Technologies, Inc., Oregon Green is a trademark of Molecular Probes, Inc., "BlackBerry" is a Trademark of Berry & Associates, Inc., "Cy2", "Cy3.5", "Cy5", and "Cy5.5" are trademarks of Amersham Biosciences Limited. "Texas Red" is a registered trademark of Molecular Probes. "ROX" and "TAMRA" are trademarks of Applied Biosystems, Inc.

In particular, the oligonucleotide and/or oligonucleotide analogue according to the present invention may comprise a FRET pair. The donor group may be placed as dangling end in the 5' end, in the 3' end or both ends. It is also preferred that at least one acceptor molecule is attached as a dangling end. The acceptor molecule may be placed as a dangling end in the 5' end or in the 3' end or both ends. Preferably, one donor group or one acceptor group is placed as a dangling end, in the 5' end of the oligonucleotide analogue. Further, if one donor group is placed as a dangling end in the 5' end, preferably an acceptor group is positioned internally or in the 3' end. Vice versa, if one acceptor molecule is placed as a dangling end in the 5' end of the oligonucleotide analogue one donor molecule is positioned internally or in the 3' end.

Accordingly, the donor group and the acceptor molecule are positioned in relation to each other (interacting with each other) so that the acceptor molecule is capable of accepting the excitation or part of the excitation of the donor group when the sequence separating the two moieties is unhybridized, but is not capable of accepting the excitation of the donor group when the sequence separating the two moieties is hybridized to a target nucleic acid.

It is a preferred embodiment of the present invention to provide a probe comprising a signalling pair and at least one hydrophobic molecule that will facilitate an improved signal-to-noise ratio of said probe compared to the corresponding probe not comprising said hydrophobic molecule.

Accordingly it is a preferred embodiment of the present invention to provide an oligonucleotide analogue (a Stemless Beacon) comprising a signalling pair and at least one hydrophobic molecule, such as a hydrophobic nucleotide, where said Stemless Beacon will self-hybridize (at least partly due to hydrophobic interactions) unless subjected to a fully complementary target under hybridization conditions.

It is even a more preferred embodiment of the present invention to provide an oligonucleotide analogue comprising a fluorophore, a corresponding quencher and at least one hydrophobic molecule, such as a hydrophobic nucleotide (a Stemless Beacon) that will facilitate better quenching of said fluorescent group by said quencher molecule (lower background) when the probe is unbound, than the background signal of a corresponding probe that does not comprise said hydrophobic molecule(s).

It is even most preferred embodiment of the present invention to a provide an oligonucleotide analogue comprising a fluorophore, a corresponding quencher and at least two hydrophobic molecules, such as hydrophobic nucleotides that will facilitate better quenching of said fluorescent group by said quencher molecule (lower background) when the probe is unbound, than the background signal of a corresponding probe that does not comprise said hydrophobic groups.

Above mentioned properties may for example be achieved by selecting a suitable position for said hydrophobic nucleotide (see more details herein below).

Hence it is a preferred, embodiment of the present invention to provide an oligonucleotide analogue comprising at least two hydrophobic molecules, such as hydrophobic nucleotides and a signalling pair where the spectral properties of said signaling pair are changed upon hybridization to a target nucleic acid or as a consequence of amplification of a target nucleic acid. In a preferred embodiment the spectral signal is low when there is no or small amounts of a target nucleic acids, and high when there is larger amounts of target nucleic acid present. When used during an amplification reaction of target sequence, e.g. by PCR, it is preferred that the spectral signal increases in correspondence to the increase of said target nucleic acid sequence.

Accordingly it is preferred to provide an oligonucleotide analogue that comprise a first sequence and a second sequence that are separated by a third sequence, where first and third sequence each comprises at least one hydrophobic molecule, such as a hydrophobic nucleotide according to the present invention, where the spectral signal is low when said first sequence is self-hybridized to second sequence and high when they are not hybridized.

It is also comprised within the present invention that the first sequence may comprise a donor for e.g. FRET, excimer or exciplex and the second sequence may comprise an acceptor for e.g. FRET, excimer or exciplex or vice versa. Preferably said donor and said acceptor are positioned so that FRET may occur when the first sequence is self-hybridized to the second sequence and accordingly FRET fluorescence may only be detected when the first sequence is hybridized to the second sequence.

Furthermore, hybridization or the formation of nucleotide or nucleotide analogue extension products constituting double stranded nucleic acids and/or nucleic acid analogues, e.g. DNA, may also be detected using a label not associated directly with the oligonucleotide and/or oligonucleotide analogues and optionally oligonucleotides used for priming the extension.

In one embodiment such a label may be selected from the group consisting of, but not limited to, Propidium iodide, Acridine Orange, ethidium bromide, LC Green, SYBR Gold, SYBR Green I, and SYBR Green II. The fluorescence properties of a fluorescent group may be modulated according to buffer conditions and physical factors. For instance temperature, ionic strength and pH are parameters that can affect the strength of the fluorescent signal obtained from a specific fluorophore. An example of a different chemical group of substances that are also known to affect fluorescence of pyrene excimers is the lipophilic surfactant molecules, as disclosed in U.S. Pat. No. 5,466,578. The authors teach that the cationic subgroup of surfactants comprising a quaternary ammonium salt with carbon chains attached, like e.g. hexadecyltrimethyl ammonium bromide, can be used to significantly increase the signal from oligonucleotides end-labeled with pyrene excimers.

Since the positive effect of surfactants on the fluorescence strength of especially dimer (or higher order) complexes of pyrene may be due to surfactant molecule displacement of water molecules from the dimer, acting to quench fluorescence, other lipophilic molecules may have similar effects on fluorescence strength. Lipophilic groups and other molecules that could displace water from intercalator dimers are often used in standard assay buffers. Examples of such molecules that have been shown to affect fluorescence strength are Triton X-100, Sodium Dodecyl Sulphate, Glycerol and DMSO.

Signal-to-Noise

The signal-to-noise ratio according to the present invention is defined as the signal strength when all or essentially all oligonucleotide analogues according to the present invention are hybridised to a homologous complementary target nucleic acid (positive signal) divided by the signal strength when the same amount of said oligonucleotide analogues are unhybridised (to the fully complementary target nucleic acid, background signal).

$$\text{Signal-to-noise} = \frac{\text{Signal when bound to homologous complementary target sequence}}{\text{Signal when unbound (to homologous complementary target sequence)}}$$

Signal-to-noise = Positive signal/background signal

Accordingly a background signal is for example when there is no target nucleic acid present, when a nucleotide analogue comprising at least one hydrophobic molecule and a signalling pair according to the present invention is self-hybridizing or when two nucleotide analogues according to the present invention are hybridised to each other, but not to their target nucleic acid.

Some signalling pairs have a low signal when they are interacting strongly (in an unbound probe) and a high signal when they are not interacting that strongly (in a hybridised probe), while others have a high signal when the two parts of the signalling pair are interacting strongly and a low signal when not interacting strongly. It is therefore clear that depending on the signalling pair used in a probe, a positive signal can either be significantly higher or lower than the background signal. As a signal-to-noise ratio of 1 indicates that the signal is the same regardless of if the probe is hybridized or unhybridized, it is preferred that the signal-to-noise ratio is as far away from 1 as possible. By saying: "the signal-to-noise ratio is either significantly higher or significantly lower than the signal-to-noise ratio of the corresponding oligonucleotide or oligonucleotide analogue not comprising the at least one hydrophobic group" is meant that, if the signal-to-noise ratio of the corresponding oligonucleotide or oligonucleotide analogue not comprising said at least one hydrophobic group is higher than 1, the oligonucleotide analogues comprising a signalling pair and at least one hydrophobic molecule according to the present invention has an even higher signal-to-noise ratio and if the signal-to-noise ratio of said corresponding oligonucleotide or oligonucleotide analogue not comprising the at least one hydrophobic group is lower than 1, the oligonucleotide analogues comprising a signalling pair and at least one hydrophobic molecule according to the present invention has an even lower signal-to-noise ratio. A higher or lower signal-to-noise ratio is also described as "being further away from a signal-to-noise ratio of the value 1" or "more different from the value 1" or "being improved".

If the two parts of a signalling pair quench each other when the oligonucleotide analogue (for example a Stemless beacon) is unbound to a target sequence (for example if the signalling pair is consisting of a fluorophore and a quencher), the signal-to-noise ratio should be higher for said Stemless Beacon according to the present invention, compared to a corresponding oligonucleotide or oligonucleotide analogue not comprising at least one hydrophobic molecule according to the present invention.

If the signal of the two parts of a signalling pair is increased when the Stemless beacon is unbound to a target sequence (for example if the signalling pair is consisting of a classical FRET pair of two fluorophores), the signal-to-noise ratio should be lower for said Stemless Beacon according to the present invention, compared to a corresponding oligonucleotide or oligonucleotide analogue not comprising at least one hydrophobic molecule.

Accordingly it is a preferred embodiment of the present invention to provide an oligonucleotide analogue comprising a signalling pair and at least one hydrophobic molecule according to the present invention, where the signal-to-noise ratio is significantly further from the value 1 than the signal-to-noise ratio of the corresponding oligonucleotide or oligonucleotide analogue not comprising said at least one hydrophobic group.

It is an even more preferred embodiment of the present invention to provide an oligonucleotide analogue comprising a signalling pair and at least two hydrophobic molecules according to the present invention, where the signal-to-noise ratio is significantly further from the value 1 than the signal-to-noise ratio of the corresponding oligonucleotide or oligonucleotide analogue not comprising said at least two hydrophobic molecules.

In one embodiment the signal to noise ratio is determined by determining the signal after incubation of an oligonucleotide analogue according to the invention with a target nucleic acid at a low temperature and a high temperature and dividing the signal obtained at the low temperature with the signal obtained at the high temperature. The low temperature should be a temperature lower than the melting temperature of a hybrid between the oligonucleotide analogue and its target sequence, for example a temperature in the range of 15° C. to 80° C., such as in the range of 15° C. to 50° C., for example in the range of 50° C. to 80° C., for example in the range of 25° C. to 70° C., preferably in the range of 15 to 40° C., such as in the range of 25 to 35° C. The high temperature should be a temperature higher than the melting temperature of a hybrid between the oligonucleotide analogue and its target sequence, for example a temperature in the range of 50° C. to 95° C., such as in the range of 60° C. to 95° C., for example in the range of 65° C. to 90° C.

When the signal to noise ratio is determined in this manner and the signal is higher than the background signal, then the signal to noise ratio is preferably at least 4.5, such as at least 5.0, for example at least 5.5, such as at least 5.8.

In a preferred embodiment the signal to noise ratio is determined as described in example 2 or in example 10 herein below.

In embodiments wherein the signal is lower than the background signal, the signal to noise ratio for example be lower than 0.75, such as lower than 0.5, for example lower than 0.25.

Solid Supports

It is a preferred embodiment to couple the Stemless Beacons according to the present invention to a solid support, or alternatively to use said Stemless Beacons to detect nucleic acids or nucleic acid analogues that are coupled to a solid support. The separation of said Stemless Beacons hybridized with nucleic acids or nucleic acid analogues from the mixture might then be performed by separating said solid support from the mixture or by washing unbound material away.

Many different kinds of solid supports are suitable for the method, depending of the desired outcome.

In one embodiment the solid support is an activated surface. An activated surface facilitates coupling of oligonucleotides or oligonucleotide analogues to the solid support.

The solid support may for example be selected from the group consisting of magnetic beads, aluminium beads, agarose beads, sepharose beads, glass, plastic surfaces, heavy metals and chip surfaces.

Magnetic beads include beads comprising a magnetic material that allow the beads to be separated from a suspension using a magnet. Aluminium beads include barcoded beads that allow the beads to be recognised. But other coded and non-coded beads can also be used in the present invention.

Agarose beads and sepharose beads may for example be separated from a suspension by centrifugation or filtration.

Plastic surfaces include for example microtiter plates or other plastic devices that may be suitable for example for diagnosis.

Chip surfaces may be made of any suitable materials, for instance, glass, resin, metal, glass covered with polymer coat, glass covered with metal coat and resin covered with metal coat. Also employable is a SPR (surface plasmon resonance) sensor plate, which is described in Japanese Patent Provisional Publication No. 11-332595. CCD is also employable as described in *Nucleic Acids Research*, 1994, Vol. 22, No. 11, 2124-2125.

Chip surfaces include cellulose and small polyacrylamide gels on a glass plate whereto oligonucleotides or oligonucleotide analogues may be fixed by making a covalent, or non-covalent bond between the polyacrylamide and the oligonucleotide (Yershov, G., et al. (1996) *Proc. Natl. Acad. Sci. USA*, 94:4913).

Chip surfaces may also be silica chips as described by Sosnowski, R. G., et al. (1997) *Proc. Natl. Acad. Sci. USA*, 94:1119-1123. Such chips are prepared by a process comprising the steps of placing an array of microelectrodes on a silica chip, forming on the microelectrode a streptavidin-comprising agarose layer, and attaching biotin-modified DNA fragments to the agarose layer by positively charging the agarose layer.

Furthermore, chip surfaces may be prepared as described by Schena, M., et al. (1996) *Proc. Natl. Acad. Sci. USA*, 93:10614-10619 wherein a process comprising the steps of preparing a suspension of an amino group-modified PCR product in SSC (i.e., standard sodium chloride-citric acid buffer solution), spotting the suspension onto a slide glass, incubating the spotted glass slide, treating the incubated slide glass with sodium boronhydride, and heating thus treated slide glass.

Furthermore columns containing the solid material can be used.

Nucleotides Comprising Hydrophobic Molecules or Hydrophobic Nucleotides

Hydrophobic molecules according to the present invention can be covalently linked to any part of a nucleotide and/or nucleotide analogue and/or coupled to its own backbone monomer unit. The hydrophobic molecules can be incorporated into said nucleotides and/or nucleotide analogues and/or backbone monomer units prior to the chemically or enzymatically synthesis, during the synthesis or post synthesis of the probes. The hydrophobic molecules can be coupled directly to the nucleotides and/or nucleotide analogues and/or backbone monomer units or by using any suitable linker.

As described above it is however preferred that the hydrophobic molecules are linked to a backbone monomer unit optionally trough a linker, wherein neither the backbone monomer unit nor the linker comprises a nucleobase.

It is an aspect of the present invention to provide an oligonucleotide analogue comprising at least one hydrophobic nucleotide analogue of the general structure

X—Y-Q wherein

X is a nucleotide or nucleotide analogue or a backbone monomer unit capable of being incorporated into the backbone of a nucleic acid or nucleic acid analogue, Q is a hydrophobic molecule according to the present invention; and Y is a linker moiety linking said nucleotide or nucleotide analogue or backbone monomer unit and said hydrophobic molecule.

By the term "incorporated into the backbone of a nucleic acid or nucleic acid analogue" is meant that the hydrophobic nucleotide may be inserted into a sequence of nucleic acids and/or nucleic acid analogues.

It is a more preferred aspect of the present invention if said oligonucleotide analogues comprising at least one hydrophobic nucleotide analogue are able to be synthesized chemically. It is even more preferred if said oligonucleotide analogues comprising at least one hydrophobic nucleotide analogue are able to be synthesized on an automated DNA synthesizing machine, using chemistries known to a person skilled in the art.

In many of the embodiments of the present invention it is preferred to provide an oligonucleotide analogue comprising at least two hydrophobic nucleotide analogues of the general structure

X—Y-Q wherein

X is a nucleotide or nucleotide analogue or a backbone monomer unit capable of being incorporated into the backbone of a nucleic acid or nucleic acid analogue, Q is a hydrophobic molecule according to the present invention; and Y is a linker moiety linking said nucleotide or nucleotide analogue or backbone monomer unit and said hydrophobic molecule.

It is a preferred embodiment of the present invention that the inserted hydrophobic nucleotide in an oligonucleotide analogue (such as a Stemless Beacon) according to the present invention do not significantly decrease binding to the target nucleic acid. Many such modifications are known to a person skilled in the art. It is even more preferred that the hydrophobic nucleotide analogues of the present invention consists of nucleotides build of one of the following: Modifications at the 2' position of a ribose ring of a nucleotide, illustrated herein above, has previously been shown to increase affinity for target nucleic acids (Yamana et al. (1991) *Tetrahedron lett.* 6347-6350) and/or intercalators linked to their own backbone monomer unit (Christensen et al. (2004) *Nucleosides, nucleotides & nucleic acids* 23: 207-225).

It is a preferred embodiment that the backbone monomer unit X is able to form a phosphordiester or phosphordiester analogue binding in the oligonucleotide or oligonucleotide analogue.

In one embodiment of the invention the hydrophobic nucleotide may for example be any of the intercalator pseudonucletides of the structures 1 to 347 described on p. 64 to 115 in international patent application WO03/052132.

Depending on the nature of the hydrophobic nucleotide, different methods for manufacture are available to the skilled person. Hydrophobic nucleotides may for example be prepared in a manner similar to preparation of intercalator pseudonucleotides as described in the international patent application WO03/052132 in the section "Preparation of intercalator pseudonucleotides" on p. 115, l. 14, to p. 121, l. 30. The skilled person will be able to make the appropriate amendments to the protocol in cases, where the hydrophobic molecule is not an intercalator.

Oligonucleotide Analogous Comprising Hydrophobic Groups

It is an object of the present invention to provide an oligonucleotide analogue comprising at least one hydrophobic molecule and a signalling pair wherein the change in signal of said oligonucleotide analogue, when said oligonucleotide analogue is going from being unhybridised to a target nucleic acid to being hybridised to a target nucleic acid or vice versa, is significantly higher than the change in signal of a hybrid between a corresponding oligonucleotide or oligonucleotide analogue, not comprising said hydrophobic molecule(s), consisting of the same nucleotide sequence as said oligonucleotide analogue and said target nucleic acid (corresponding hybrid).

In a preferred embodiment the oligonucleotide analogues of the present invention comprise n nucleotides and/or nucleotide analogues, wherein n is an integer of at least 4. It is preferred that n is at least 5, more preferred at least 6, even more preferred at least 7. For example n may be an integer in the range of 4 to 100, such as in the range of 5 to 90, for example in the range of 7 to 100, such as in the range of 7 to 80, for example in the range of 7 to 60, such as in the range of 7 to 40, for example in the range of 7 to 30, such as in the range of 7 to 20, for example in the range of 15 to 50. In one embodiment the oligonucleotide analogues may comprise between 1 and 100 nucleobases or nucleobase analogues, such as between 5 and 40 nucleobases or nucleobase analogues, for example between 5 and 30 nucleobases or nucleobase analogues, such as between 5 and 25 nucleobases or nucleobase analogues, for example between 5 and 20 nucleobases or nucleobase analogues. It is more preferred that oligonucleotide analogues of the present invention comprise for example between 6 and 25 nucleobases or nucleobase analogues as well as at least one hydrophobic molecule and a signalling pair.

It is an even more preferred embodiment that the oligonucleotide analogues of the present invention comprise for example between 6 and 25 nucleobases or nucleobase analogues as well as between 2 and 6 hydrophobic molecules and a signalling pair.

The hydrophobic molecules may be placed in any desirable position within a given oligonucleotide or oligonucleotide analogue. For example, a hydrophobic molecule may be placed at the end of the oligonucleotide analogue or a hydrophobic molecule may be placed in an internal position within the oligonucleotide analogue.

It is preferred that the hydrophobic nucleotide is positioned at the most 9, such as at the most 8, for example at the most 7, such as at the most 6 nucleotides and/or nucleotide analogues from one end.

It is preferred that either part of the signalling pair is positioned closer to the 5' end and the 3' end, respectively, than the hydrophobic nucleotide. Thus, the hydrophobic nucleotide preferably has a more internal position than either of the parts of the signalling pair.

It is preferred the any part of a signalling pair is positioned in relation to any hydrophobic nucleotides in a manner so that at least 1, for example 2, such as 3, for example 4, such as 5, for example more than 5, such as in the range of 1 to 10, preferably in the range of 1 to 8, such as in the range of 1 to 6, for example in the range of 2 to 6 nucleotide/nucleotide analogues are separating any part of a signalling pair and any hydrophobic nucleotide.

In a preferred embodiment the oligonucleotide analogue comprises between 1 and 5, such as between 5 and 10, such as between 10 and 15, for example between 15 and 20 hydrophobic nucleotides. It is very preferred that the oligonucleotide analogue comprises at least 2, for example between 2 and 5, hydrophobic nucleotides Hydrophobic molecules in an oligonucleotide analogue may be placed in any position in relation to each other. For example they may be placed next to each other, or they may be positioned so that 1, such as 2, for example 3, such as 4, for example 5, such as more than 5 nucleotides are separating the hydrophobic molecules. It is however preferred that all hydrophobic nucleotides are separated by at least 1 nucleotide or nucleotide analogue, which is not a hydrophobic nucleotide.

In embodiments wherein the oligonucleotide analogues comprises at least 2 hydrophobic nucleotides it is preferred that they are positioned in opposite halves of said oligonucleotide analogue. It is thus preferred that one hydrophobic nucleotide is positioned within the 5' half of the oligonucleotide analogue and the other hydrophobic nucleotide is positioned within the 3' end of the oligonucleotide analogue.

It is preferred that at least two, preferably all hydrophobic nucleotides are positioned at the most 9, such as at the most 8, for example at the most 7, such as at the most 6 nucleotides and/or nucleotide analogues from one end.

More preferably, at least two hydrophobic nucleotides are positioned in opposite halves and at the most 9, such as at the most 8, for example at the most 7, such as at the most 6 nucleotides and/or nucleotide analogues from their respective closest end. Thus, the preferred maximal distance from the ends may be dependent on the length of the oligonucleotide analogue.

It is furthermore preferred that either part of the signalling pair is positioned closer to the 5' end and the 3' end than at least 1, more preferably at least 2, for example all hydrophobic nucleotides. Thus, at least 1, preferably at least 2, for example all hydrophobic nucleotides preferably has a more internal position than either of the parts of the signalling pair.

In a very preferred embodiment of the invention the oligonucleotide analogue comprises at least two hydrophobic nucleotides and said at least two hydrophobic nucleotides are positioned symmetrically within said oligonucleotide analogues. Thus, it is preferred that said at least two hydrophobic nucleotides are positioned in approximately the same distance, more preferably at the same distance from the respective parts of the signalling pair.

In another embodiment it is preferred that said at least two hydrophobic nucleotides are positioned in approximately the same distance, more preferably at the same distance from the center of the oligonucleotide analogue.

"Approximately the same distance" in the present context means the same number of nucleotides and/or nucleotide analogues away +/−1 nucleotide or nucleotide analogue.

In embodiments wherein the oligonucleotide analogues comprises an even number of hydrophobic nucleotides more than two, it is preferred that each pair of hydrophobic nucleotides are positioned either in approximately the same distance, more preferably at the same distance from the respective parts of the signalling pair or in approximately the same distance, more preferably at the same distance from the center of the oligonucleotide analogue.

When the oligonucleotide analogue comprise more than one hydrophobic molecule, it is a preferred aspect of the present invention that at least one of said hydrophobic molecules is positioned so that it will ensure that the change in signal of said oligonucleotide analogue, when said oligonucleotide analogue is going from being unhybridised to a target nucleic acid to being hybridised to a target nucleic acid or vice versa, is significantly higher than the change in signal of a corresponding hybrid, not comprising said hydrophobic molecule.

It is more preferred if there is at least one of said hydrophobic nucleotide analogues positioned in each half of said oligonucleotide analogue. In one preferred embodiment a first hydrophobic molecule, within an oligonucleotide analogue having a two part signalling pair positioned with a part in the 3' and 5' end respectively, is placed close to the 3'-end and second hydrophobic molecule is placed close to the 5'-end, i.e. they can be placed at any position in their respective ends of the oligonucleotide analogue and optionally comprise a third, fourth, fifth or more hydrophobic molecules placed at any position. Said hydrophobic nucleotide analogues could independently be positioned next to a part of the signalling pair, for example with one nucleotide, such as two nucleotides, for example 3 nucleotides, such as 4 nucleotides, for example 5 nucleotides, such as 6 nucleotides, for example 7 nucleotides, such as 8 nucleotides, for example 9 nucleotides, such as 10 nucleotides, for example between 0 and 10 nucleotides separating said hydrophobic nucleotide analogue and the closest part of the signalling pair.

It is more preferred that all hydrophobic molecules are positioned so that the change in signal of the oligonucleotide analogue comprising said hydrophobic molecules, when said oligonucleotide analogue is going from being unhybridised to a target nucleic acid to being hybridised to a target nucleic acid or vice versa, is significantly higher than the change in signal of a corresponding hybrid, not comprising said hydrophobic molecules.

It is therefore an aspect of the present invention to position hydrophobic molecules in relation to other hydrophobic molecules and the part of a signalling pair comprised in the same oligonucleotide analogue. Hence it is a preferred embodiment of the present invention to provide an oligonucleotide analogue comprising a two part signalling pair where each part is positioned in each end of said oligonucleotide analogue and two hydrophobic molecules according to the present invention, one positioned in each half of said oligonucleotide analogue at a distance to the closest part of the signalling pair that is equal to or approximately equal to the distance of the other hydrophobic molecule and its distance to the other part of said signalling pair.

It is an even more preferred embodiment of the present invention to provide an oligonucleotide analogue comprising a two part signalling pair where each part is positioned in each end of said oligonucleotide analogue and at least two hydrophobic molecules according to the present invention, where all hydrophobic molecules are positioned in relation to each other so that when the probe is unbound all hydrophobic molecules will have hydrophobic interactions with at least one other hydrophobic molecule and this hydrophobic interaction will bring the two parts of said signalling pair in close proximity.

Above mentioned properties may for example be achieved by positioning of the hydrophobic nucleotides as described above.

In some embodiments of the present invention it is preferred that there is at least one nucleotide or nucleotide analogue separating hydrophobic nucleotide analogues from all other hydrophobic nucleotide analogues in the same oligonucleotide analogue sequence. This is due to the fact that if there is a too high concentration of hydrophobic molecules in a small area of an oligonucleotide, this tends to reduce the affinity towards a target sequence.

As some hydrophobic molecules, especially those with conjugated π-electrons but also others, are able to quench fluorescence from a fluorophore by either a FRET like mechanism or a non-FRET like collision mechanism, it is even more preferred that there is at least 1, for example 2, such as 3 nucleotide or nucleotide analogue separating said hydrophobic nucleotide from all other hydrophobic nucleotides and from any part of the signalling pair. In this way quenching and affinity reduction by the hydrophobic molecules is minimised.

The oligonucleotide analogues may comprise any kind of nucleotides and/or nucleotide analogues, such as the nucleotides and/or nucleotide analogues described herein above. Accordingly, the oligonucleotide analogue may comprise one or more selected from the group consisting of subunits of DNA, RNA, PNA, Homo-DNA, b-D-Altropyranosyl-NA, b-D-Glucopyranosyl-NA, b-D-Allopyranusyl-NA, HNA, MNA, ANA, LNA, CNA, CeNA, TNA, (2'-NH)-TNA, (3'-NH)-TNA, α-L-Ribo-LNA, α-L-Xylo-LNA, β-D-Xylo-LNA, α-D-Ribo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo[4.3.0]-DNA, Bicyclo[3.2.1]-DNA, Bicyclo[4.3.0]amide-DNA, β-D-Ribopyranosyl-NA, α-L-Lyxopyranosyl-NA, 2'-R-RNA, 2'-OR-RNA, α-L-RNA, α-D-RNA, β-D-RNA and mixtures thereof.

As hydrophobic molecules are not easily dissolved in water, and the hybridisations and/or measurements according to the present invention will take place in an aqueous solution, there is an upper limit to the number of hydrophobic molecules that can be comprised in a Stemless Beacon.

Hence it is a preferred embodiment of the present invention to provide an oligonucleotide analogue comprising at least one hydrophobic group according to the present invention that is easily dissolved into the aqueous buffer used in the assay.

It is a more preferred embodiment of the present invention to provide an oligonucleotide analogue where there are a maximum of 50% hydrophobic nucleotides according to the present invention compared to the number of nucleobases. That means that there can be a maximum of one hydrophobic nucleotide according to the present invention present in an oligonucleotide analogue for every two nucleobases present in said oligonucleotide analogue.

It is an even more preferred embodiment of the present invention to provide an oligonucleotide analogue where there are a maximum of for example between 5% and 50%, such as between 5% and 45%, for example between 10% and 45%, such as between 12% and 45% hydrophobic groups according to the present invention compared to the number of nucleobases of said oligonucleotide analogue.

The solubility in water will be dependent on the hydrophobicity of the hydrophobic molecule. If the hydrophobic molecule is pyrene, it is preferred that the oligonucleotide analogue comprises at the most 1 hydrophobic nucleotide per 3 nucleotides/nucleotide analogues. If the hydrophobic molecule is more hydrophobic than pyrene (i.e. has a higher log P value) it is preferred that the oligonucleotide analogue comprises at the most 1 hydrophobic nucleotide per 4 nucleotides/nucleotide analogues. If the hydrophobic molecule is less hydrophobic than pyrene (i.e. has a lower log P value) it is preferred that the oligonucleotide analogue comprises at the most 1 hydrophobic nucleotide per 2 nucleotides/nucleotide analogues.

However as we are introducing hydrophobic molecules and it is important that the Stemless Beacon of the present invention is soluble in an aqueous solution, it is preferred if the backbone monomer unit is charged after insertion into the oligonucleotide analogue of the Stemless beacon. Therefore it is an even more preferred embodiment that the backbone monomer units of an oligonucleotide analogue according to the present invention are selected from the group of backbone monomer units with charged backbones such as DNA, RNA, HNA, MNA, ANA, LNA, CNA, CeNA, TNA, (2'-NH)-TNA, (3'-NH)-TNA, α-L-Ribo-LNA, α-L-Xylo-LNA, β-D-Xylo-LNA, α-D-Ribo-LNA, [3.2.1]-LNA, Bicyclo-DNA, 6-Amino-Bicyclo-DNA, 5-epi-Bicyclo-DNA, α-Bicyclo-DNA, Tricyclo-DNA, Bicyclo[4.3.0]-DNA, Bicyclo[3.2.1]-DNA, Bicyclo[4.3.0]amide-DNA, β-D-Ribopyranosyl-NA, α-L-Lyxopyranosyl-NA, 2'-R-RNA, α-L-RNA or α-D-RNA, β-D-RNA and mixtures thereof and hybrids thereof, as well as phosphorous atom modifications thereof, especially modifications that leaves the backbone charged.

The Stemless Beacons of this invention are particular well suited for the detection, identification and quantification of target sequences in closed tube assays, also designated homogenous assays. This also includes asymmetric and competitive PCR assays, as well as assays comprising PCR openers, blockers and many other modified PCR assays. Furthermore as some of the Stemless Beacons presented here are nuclease resistant, they are also particularly well suited for detection, identification and quantification of target sequences in cells, tissues or organisms, whether living or not. In yet another embodiment, the present invention is also directed to an array comprising two or more support bound Stemless Beacons suitable for detecting, identifying or quantifying a target sequence of interest. Stemless Beacons are convenient because they provide a means to rapidly interrogate numerous samples of interest without using a secondary detection system.

High affinity of synthetic nucleic acids towards target nucleic acids may greatly facilitate detection assays and furthermore synthetic nucleic acids with high affinity towards target nucleic acids may be useful for a number of other purposes, such as gene targeting and purification of nucleic acids. Oligonucleotide analogues comprising hydrophobic groups have in some cases been shown to increase affinity for homologous complementary nucleic acids.

It is an advantage of some of the oligonucleotide analogues according to the present invention that the melting temperature of a hybrid consisting of an oligonucleotide analogue comprising at least one hydrophobic molecule and an essentially complementary DNA (DNA hybrid) can be significantly higher than the melting temperature of a duplex consisting of said essentially complementary DNA and a DNA complementary thereto.

Accordingly, oligonucleotide analogues according to the present invention may form hybrids with DNA with higher affinity than naturally occurring nucleic acids. The melting temperature is preferably increased with 1 to 30° C., for example from 5 to 20° C., such as from 10° C. to 15° C., for example from 2° C. to 5° C., such as from 5° C. to 10° C., such as from 15° C. to 20° C., for example from 20° C. to 25° C., such as from 25° C. to 30° C., for example more than 30° C. higher.

In another embodiment of the present invention an oligonucleotide analogue comprising one or more hydrophobic molecules according to the present invention may form a triple stranded structure (triplex-structure) consisting of said oligonucleotide analogue bound by either Hoogstein or reverse Hoogstein base pairing to a homologous complementary nucleic acid or nucleic acid analogue or oligonucleotide or oligonucleotide analogue.

In another preferred embodiment of the present invention said oligonucleotide analogue may increase the melting temperature of said Hoogstein base pairing in said triplex-structure.

In yet another even more preferred embodiment of the present invention said oligonucleotide analogue may increase the melting temperature of said Hoogstein base pairing in said triplex-structure in a manner not dependent on the presence of specific sequence restraints like purine-rich•pyrimidine-rich nucleic acid or nucleic acid analogue duplex target sequences. Accordingly, said Hoogstein basepairing in said triplex-structure has significantly higher melting temperature than the melting temperature of said Hoogstein basepairing to said duplex target if said oligonucleotide or oligonucleotide analogue had no hydrophobic molecules.

Accordingly, oligonucleotide analogues according to the present invention may form triplex-structures with homologous complementary nucleic acid or nucleic acid analogue or oligonucleotide or oligonucleotide analogue with higher affinity than naturally occurring nucleic acids. The melting temperature is preferably increased with from 2-50° C., such as from 2-40° C., such as from 2 to 30° C., for example from 5 to 20° C., such as from 10° C. to 15° C., for example from 2° C. to 5° C., such as from 5° C. to 10° C., for example from 10° C. to 15° C., such as from 15° C. to 20° C., for example from 20° C. to 25° C., such as from 25° C. to 30° C., for example from 30° C. to 35° C., such as more than 35° C.

Triplex-formation may or may not proceed in strand invasion, a process where the Hoogstein base-paired third strand invades the target duplex and displaces part of or the entire identical strand to form Watson-Crick base pairs with the complementary strand. This can be exploited for several purposes.

If the oligonucleotide analogue is to be used for detection of a polymorphic site, it is preferred that the polymorphic site is positioned central in the oligonucleotide analogues, preferably within the 10, such as within the 8, for example within the 6, such as within the 4 most centrally positioned nucleotides and/or nucleotide analogues of the oligonucleotide analogue.

Multiplexing

It is often advantageous to receive a positive signal when detecting, identifying or quantifying a target sequence. The researcher is often better of to ask the question "what genotype is present in the sample?" instead of just asking "is genotype A present in the sample?" It is therefore important that correct controls are included in the experiments. A control for a quantification reaction could for example be to quantify one or more house holding genes. Likewise a control for a mutation specific probe could be a probe specific for the wild type. If the control could be added to the same reaction container in the assay it would be ensured that (at least most of) the conditions of the control and the assay are the same, and therefore this is often advantageous over running parallel experiments. When more than one experiment is included in an assay, it is said to be a multiplexing assay.

The specificity of probes is also very dependent on the nature of the mismatch. SantaLucia demonstrated a clear trend in order of decreasing stability: "G-C">"A-T">"G•G">"G•T"≧"G•A">"T•T"≧"A•A">"T•C"≧"A•C"≧"C•C", meaning that "G" is the most promiscuous nucleobase, since it forms the strongest base pair and the strongest mismatches (SantaLucia & Hicks (2004) *Annu. Rev. Biophys. Biomol. Struct.* 33: 415-440). On the other hand, "C" is the most discriminating nucleobase, since it forms the strongest pair and the three weakest mismatches followed by "A". Hence the order of specificity of the single nucleotides is as follows: "C">"A">"T">"G". As described above, the methylation status of DNA is translated into a "C"/"T" mismatch in bisulphite converted DNA on one strand and conversely a "G"/"A" mismatch on the complementary strand after PCR amplification of the converted DNA and many mutations are also "C" to "T" transitions. It would therefore be most discriminatory if one probe (for example specific for methylated DNA) comprises the highly selective "C" base at the polymorphic site, and the other probe (specific for unmethylated DNA) comprises an "A" at the polymorphic site. Whilst this is most efficient, it means that the two probes will be highly homologous to each other. Properly designed oligonucleotide analogues according to the present invention, bind stronger to their fully complementary DNA target than to the not fully complementary probe for the other genetic variant. Pairs of oligonucleotide analogues comprising hydrophobic molecules positioned in one probe so they would be positioned in close proximity to hydrophobic molecules of the other probe if said homologous complementary (but not fully complementary) probes were to hybridise are extremely well suited to this application (see FIG. 5).

It is therefore an embodiment of the present invention to provide at least two oligonucleotide analogues comprising at least one hydrophobic molecule, such as a hydrophobic nucleotide and a signalling pair each according to the present invention to the same assay container, where said at least two oligonucleotide analogues are individually complementary to different target sequences. Said target sequences may be a target sequence and a mutant sequence thereof.

It is an even more preferred embodiment of the present invention to provide at least two oligonucleotide analogues comprising at least one hydrophobic molecule, such as a hydrophobic nucleotide and a signalling pair according to the present invention that are able to distinguish between a target nucleic acid or target nucleic acid analogue and at least one known mutant sequence thereof. The variation between the target sequence and the known mutant sequence can be a mutation, methylation status, deletion, insertion or a similar small change.

It is an aspect of the present invention that the signals from the labelling pair on Stemless Beacons, if used in the same assay container, can be distinguished from each other, while other physical differences like melting temperature or physical spotting can be used to distinguish between oligonucleotide analogues (such as Stemless Beacons) in other embodiments.

Multiplexing of two or more oligonucleotide analogues (such as Stemless Beacons) in one tube using one common set of primers is another aspect of the present invention. The possibility for a higher degree of complexity of multiplexing is possible on many of the newer real-time PCR instruments, where up to 5 or 6 different fluorophores can be measured at a time. Multiplexing with oligonucleotide analogues (such as Stemless Beacons) according to the present invention will be easier than with most other technologies, firstly because of the shorter length of the oligonucleotide analogues of the invention (such as Stemless Beacons) compared to normal Molecular Beacons due to the lack of a "stem" region, reducing the risk of non-specific hybridisation and furthermore because hydrophobic molecules added internally in a sequence will reduce the risk of that sequence acting as a non-specific template permitting spurious primer extension.

It is therefore also a preferred embodiment of the present invention to provide at least two oligonucleotide analogues all comprising at least one hydrophobic molecule, such as a hydrophobic nucleotide and a signalling pair according to the present invention that are able to distinguish between sequences comprising a single polymorphic site. Where said oligonucleotide analogues are present during an amplification reaction. The amplification reaction is preferentially taken place in a "closed tube".

It is an even more preferred embodiment of the present invention to provide two oligonucleotide analogues both comprising at least one hydrophobic molecule and a signalling pair according to the present invention that are able to distinguish between a target sequence and a single point mutation of said target sequence, where said oligonucleotide analogues are present during an amplification reaction and homologous complementary to their respective strands of said amplified sequence. The amplification reaction is preferentially taken place in a "closed tube". If said mutation is a methylation difference, a "C" to "T", "T" to "C", "A" to "G" or "G" to "A" transition, it is most preferred if one Stemless beacon comprise the highly selective "C" base at the polymorphic site, and the other probe comprises an "A" at the polymorphic site.

Additional Methods and Assay Conditions
Determining the Presence, Identification and Quantifying by Hybridization The presence, identification and quantification of a target sequence and/or a mutant sequence according to the invention may be determined by the strength, presence or absence of a hybridisation specific signal.

The determination of the extent of hybridization may be carried out by any of the methods well known in the art. If there is no detectable hybridization, the extent of hybridization is said to be 0. The oligonucleotide analogues according to the present invention comprise hydrophobic moieties and signalling pairs, which may be used to detect hybridization directly.

The oligonucleotide analogues, which may be used as probes for detection of presence, identification and/or quantification, should be capable of specific interaction with their target nucleic acids and/or nucleic acid analogues. When discriminating between target sequences and mutant sequences, the difference in melting or affinity temperature is a parameter that may be commonly used. When using this strategy oligonucleotide analogues comprising at least one hydrophobic molecule and a signalling pair according to the present invention provide a tool for the efficient discrimination. When at least one of the nucleotides in said oligonucleotide analogue is not hybridized the melting temperature of that hybrid will be lower than the melting temperature of a comparable hybrid wherein all nucleotides are hybridized.

Corresponding target nucleic acids and/or nucleic acid analogues or oligonucleotide analogues according to present invention may be labelled by any of several methods used to detect the presence of hybridized oligonucleotide analogues. The choice of using the oligonucleotide analogues according to the present invention with or without more than one signalling pair may depend on required sensitivity, the specificity as well as other factors. The choice label depends on the sensitivity, ease of conjugation with the probe, stability requirements, and available instrumentation.

Situations can be envisioned in which the detection probe comprise DNA or RNA. Such probes can be labelled in various ways depending on the choice of label. Radioactive probes are typically made using commercially available nucleotides containing the desired radioactive isotope. The radioactive nucleotides can be incorporated into probes by several means such as by nick translation of double-stranded probes; by copying single-stranded M 13 plasmids having specific inserts with the Klenow fragment of DNA polymerase in the presence of radioactive dNTP; by transcribing cDNA from RNA templates using reverse transcriptase in the presence of radioactive dNTP; by transcribing RNA from vectors containing SP6 promoters or T7 promoters using SP6 or T7 RNA polymerase in the presence of radioactive NTP;

normal PCR including hot dNTPs; by tailing the 3' ends of probes with radioactive nucleotides using terminal transferase; or by phosphorylation of the 5' ends of probes using [$^{32}$P]-ATP and polynucleotide kinase.

Non-radioactive probes are often labelled by indirect means. Generally, one or more ligand molecule(s) is/are covalently bound to the probe. The ligand(s) then binds to an anti-ligand molecule, which is either inherently detectable or covalently bound to a signal system, such as a detectable enzyme, a fluorescent compound, or a chemiluminescent compound. Ligands and anti-ligands may be varied widely. Where a ligand has a natural anti-ligand, for example, biotin, thyroxine, and cortisol, it can be used in conjunction with the labelled, naturally occurring anti-ligands. Alternatively, any haptenic or antigenic compound can be used in combination with an antibody.

As mentioned an oligonucleotide analogue according to the present invention is also conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include, but is not limited to, fluorescein and its derivatives, rhodamine and its derivatives, dansyl, umbelliferone, etc. Chemiluminescent compounds include luciferin, AMPPD ([3-(2'-spiroamantane)-4-methoxy-4-(3'-phosphoryloxy)-phenyl-1,2-dioxetane]) and 2,3-dihydrophthalazinediones, e.g., luminol.

The amount of labelled probe that is present in the hybridization medium or extraction solution may vary widely. Generally, substantial excesses of probe over the stoichiometric amount of the target nucleic acid will be employed to enhance the rate of binding of the probe to the target DNA. By exploiting the high-affinity annealing properties and/or the hydrophobic interactions of oligonucleotide analogues according to the present invention towards certain nucleic acids, it may not be necessary to use substantial excesses of probe. Treatment with ultrasound by immersion of the reaction vessel into commercially available sonicators can often accelerate the hybridization rates.

In some embodiments of the present invention, unlabelled species or excess label is removed before detection is carried out. Removal is often done by affixing either probe or target to a solid support (described herein above), where after washing can easily be done. After hybridization at a temperature and time period appropriate for the particular hybridization solution used, the support to which the capturing probe (oligonucleotide analogue according to this invention): corresponding target DNA hybridization complex is attached, is introduced into a wash solution typically containing similar reagents (e.g., sodium chloride, buffers, organic solvents and detergent), as provided in the hybridization solution. These reagents may be at similar concentrations as the hybridization medium, but often they are at lower concentrations when more stringent washing conditions are desired. The time period for which the support is maintained in the wash solutions may vary from seconds to several hours or more. Either the hybridization or the wash medium can be stringent. After appropriate stringent washing, the correct hybridization complex may now be detected in accordance with the nature of the label.

The Stemless Beacons are conjugated directly with the label. For example where the label is fluorescent, the Stemless Beacons with associated hybridization complex substrate is detected by first irradiating with light of a particular wavelength. The sample absorbs this light and then emits light of a different wavelength, which is picked up by a detector (Physical Biochemistry, Freifelder, D., W. H. Freeman & Co. (1982), pp. 537-542). Where the label is radioactive, the sample is exposed to X-ray film or a phosphor imager screen etc. Where the label is an enzyme, the sample is detected by incubation on an appropriate substrate for the enzyme. The signal generated may be a coloured precipitate, a coloured or fluorescent soluble material, or photons generated by bioluminescence or chemiluminescence.

When the label is an enzyme preferably the enzyme is capable of catalysing the production of a coloured precipitate to indicate a positive reading, preferred enzymes according to the invention may be selected from the group consisting horseradish peroxidase, alkaline phosphatase, calf intestine alkaline phosphatase, glucose oxidase and beta-galactosidase. For example, alkaline phosphatase will dephosphorylate indoxyl phosphate, which will then participate in a reduction reaction to convert tetrazolium salts to highly coloured and insoluble formazans.

Detection of a hybridization complex may require the binding of a signal-generating complex to a hybrid of corresponding target and oligonucleotide analogue. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, attaching fluorescent or enzyme molecules or radioactive labels to the antibodies generates a signal (Tijssen, P. "Practice and Theory of Enzyme Immunoassays," Laboratory Techniques in Biochemistry and Molecular Biology, Burdon, R. H., van Knippenberg, P. H., Eds., Elsevier (1985), pp. 9-20.)

Several kinds of fluorescence can be used for detection, including excimers, exciplexes, FRET complexes and charge-transfer complexes.

Some interesting assays are hybridization and fluorescence based detection assays involving probes of oligonucleotide or oligonucleotide analogue comprising hydrophobic molecules affixed to a solid support. In these cases an affixed probe is hybridized to a corresponding target nucleic acid or corresponding target nucleic acid analogue, and a signal is thereby generated. Afterwards excess or unbound nucleic acid or nucleic analogue strands are removed by stringent washes and remaining labels are detected. This method is well suited for genotyping point mutations and expression profiles.

Detection and Differentiating Between Target Nucleic Acids, Target Nucleic Acid Analogues and Mutants Sequences by Melting Temperature The present invention relates to oligonucleotide analogues comprising at least one hydrophobic molecule and a signalling pair.

In one embodiment of the present invention said oligonucleotide analogue has a significantly higher affinity for its target nucleic acid sequence, than for any other nucleic acid sequences present in the mixture.

In a preferred embodiment of the present invention, the detection procedure is dependent on temperature, including assays where washing procedures are used to remove nucleic acids or nucleic acid analogues with a lower affinity for said oligonucleotide analogue than the target nucleic acid or target nucleic acid analogue has.

In another preferred embodiment of the present invention high melting temperature indicates the presence of target nucleic acid in the mixture.

In an even more preferred embodiment the detection of hybridization is carried out after stringent washing procedures and a positive signal indicates the presence of target nucleic acid in the mixture.

The determination of the extent of hybridization may be carried out by any of the methods well known in the art. The oligonucleotide analogues, comprising at least one hydrophobic molecule according to the present invention, may be used to detect hybridization directly.

In one embodiment of the present invention, several non-identical oligonucleotides and/or oligonucleotide analogues comprising hydrophobic molecule(s) and signalling pairs according to the present invention may be used at one time to address different target nucleic acids or nucleic acid analogues in a mixture, thus facilitating the detection of a number of nucleic acids or nucleic acid analogues corresponding to the number of said oligonucleotides and/or oligonucleotide analogues.

Detection, Quantification and/or Differentiating Between Target Nucleic Acids, Target Nucleic Acid Analogues and the Mutants Sequences Using Spectral Properties The present invention relates to oligonucleotide analogues comprising at least one hydrophobic molecule and a signalling pair, wherein said signalling pair comprises monomer fluorescence and/or intramolecular excimer and/or intramolecular exciplex and/or intramolecular FRET complex and/or an intramolecular charge transfer complex.

In a preferred embodiment an oligonucleotide analogue comprise a signalling pair where one part of said signalling pair is positioned in or close to one end of said oligonucleotide analogue and the other part of said signalling pair is positioned in or close to the other end of said oligonucleotide analogue. Furthermore said oligonucleotide analogue comprise at least two hydrophobic molecules one in each half of said oligonucleotide analogue, and said hydrophobic molecules are, when unbound to a target nucleic acid, capable of facilitating significantly better interaction of said signalling pair than the interaction of a signalling pair in an oligonucleotide or oligonucleotide analogue lacking said hydrophobic groups consisting of the same nucleotide sequence as said oligonucleotide or oligonucleotide analogue. Thus the oligonucleotide analogue comprising at least two hydrophobic molecules will have a higher signal or a lower background signal than the corresponding oligonucleotide or oligonucleotide analogue not comprising the hydrophobic molecules.

Method of Detecting the Presence of Corresponding Target Nucleic Acids and/or Target Nucleic Acid Analogues and the Mutants Hereof It is one object of the present invention to provide methods of detecting a nucleic acid or nucleic acid analogue comprising a specific target sequence, which may differ from any other sequences by at least one nucleobase, wherein the method comprises the steps of
  a) providing a mixture of nucleic acids and/or nucleic acid analogues, which is desirable to test for the mutation; and
  b) providing an oligonucleotide analogue, comprising at least one hydrophobic molecule and a signalling pair, capable of hybridising with said specific sequence; and
  c) incubating said oligonucleotide analogue with the mixture comprising nucleic acids or nucleic acid analogues under conditions allowing for hybridisation; and
  d) washing away sequences that have less affinity to said oligonucleotide analogue than the target sequence; and
  e) determining the presence or absence the target sequence.

Furthermore, the invention provides methods of differentiating between a nucleic acid or nucleic acid analogue comprising a specific target sequence and a nucleic acid comprising a mutant sequence.

Preferably, either hybridization, measuring or separation is carried out under high-stringency conditions. For example separation in solution may be done e.g. by electrophoresis or chromatography.

More preferably there is only hybridization between the oligonucleotide or oligonucleotide analogue, comprising at least one hydrophobic molecule and a signalling pair according to the present invention, and the corresponding target nucleic acid and/or nucleic acid analogue when hybridization is carried out under high-stringency conditions.

In yet another preferred embodiment, an oligonucleotide analogue comprising at least one hydrophobic molecule according to the present invention is complementary to the target nucleic acid and/or the target nucleic acid analogue.

In still another preferred embodiment, an oligonucleotide analogue comprising at least one hydrophobic molecule according to the present invention is complementary to the mutant of the target nucleic acid and/or the target nucleic acid analogue In a further preferred embodiment, at least two oligonucleotide analogues comprising at least one hydrophobic molecule according to the present invention are individually complementary to a target sequence and at least one known mutant sequence hereof.

In a more preferred embodiment more oligonucleotide analogues comprising at least one hydrophobic molecule according to the present invention are used to differentiate between target nucleic acid and/or target nucleic acid analogue and all other known nucleic acids that vary in as little as one position. The variation between the target nucleic acids and the closes looking nucleic acid can for example be mutations, methylation status, deletion, insertion or similar small changes. In the most preferred embodiment more oligonucleotide analogues comprising at least one hydrophobic molecule according to the present invention are used to differentiate between target nucleic acid and/or the target nucleic acid analogue and known types of single point mutations hereof.

In a preferred embodiment differentiation between target nucleic acids and/or target nucleic acid analogues and the mutants hereof is carried out by the use of intermolecular excimers, exciplexes, FRET complexes and/or charge-transfer complexes.

Method of Detecting the Presence of Corresponding Target Nucleic Acids and/or Target Nucleic Acid Analogues and the Mutants Hereof Using Melting Temperature It is one object of the present invention to provide methods of detecting a nucleic acid or nucleic acid analogue comprising a specific target sequence, which may differ from any other sequences by at least one nucleobase, wherein the method comprises the steps of
  a) providing a mixture of nucleic acids and/or nucleic acid analogues, which is desirable to test for the mutation; and
  b) providing a Stemless Beacons comprising at least one hydrophobic molecule and a signalling pair capable of hybridising with said specific sequence; and
  c) incubating said Stemless Beacon with the mixture comprising nucleic acids or nucleic acid analogues under conditions allowing for determination of melting and/or affinity temperature; and
  d) determining the presence or absence the target sequence.

In another preferred embodiment two Stemless Beacons, each comprising at least one hydrophobic molecule and a signalling pair according to the present invention are used, one specific for the target nucleic acid and one specific for the mutant nucleic acid.

In a more preferred embodiment said two Stemless Beacons, generate signals that can be distinguished from one another.

In an even more preferred embodiment a high melting and/or affinity temperature of the target nucleic acid specific oligonucleotides or oligonucleotide analogues, comprising at least one hydrophobic molecule and a signalling pair according to the present invention means that the target nucleic acid is present and a high melting and/or affinity temperature of the mutant nucleic acid specific oligonucleotides or oligonucleotide analogues, comprising at least one hydrophobic molecule and a signalling pair according to the present invention means that the mutant nucleic acid is present.

Method for Detection Including Enzymatic Step

The presence, identification or quantification of a target sequence and/or mutant sequence according to the present invention may be performed by a method including an enzymatic step.

Accordingly, in one embodiment the present invention relates to methods for detecting, identifying and/or quantifying a target sequence and/or a mutant sequence.

A more preferred embodiment of the present invention relates to methods for detecting, identifying and/or quantifying a target sequence and/or a mutant sequence, which comprises the steps of
  g) providing a mixture of nucleic acids and/or nucleic acid analogues, which is desirable to use for detecting, identifying and/or quantifying of target sequences or a mutant sequence; and
  h) providing a set of primers and an oligonucleotide analogue according to the present invention wherein said primers and said oligonucleotide analogue are capable of hybridizing with said target sequence and/or the mutant sequence; and
  i) incubating said primers and oligonucleotide or oligonucleotide analogue with said mixture of nucleic acids and/or nucleic acid analogues under conditions allowing for hybridization of said primers to said nucleic acids and/or nucleic acid analogues; and
  j) using said hybridized target sequence for templating extension of the 3' end of said primer with nucleotides or nucleotide analogues or oligonucleotides or oligonucleotide analogues; and
  k) hybridizing said oligonucleotide or oligonucleotide analogue comprising at least one hydrophobic molecule and determine the signal strength of said signalling pair, and
  l) optionally repeating step c) to e)

Preferably, hybridization is carried out under high-stringency conditions.

More preferably there is only hybridization between the oligonucleotide or oligonucleotide analogue, comprising at least one hydrophobic molecule according to the present invention, and the corresponding target nucleic acid and/or nucleic acid analogue when hybridization is carried out under high-stringency conditions.

Another aspect is that the signal strength of the signalling pair can be correlated to the presence, identification and/or quantity of said target and/or mutant sequence by a person skilled in the art.

In one embodiment the method is detecting a target and/or mutant sequence, which differ from the target sequence by at least one nucleobase, preferably which differ from the target sequence by in the range from 1 to 5 nucleobases.

In an even more preferred embodiment two oligonucleotides or oligonucleotide analogues, each comprising at least one hydrophobic molecule and a signalling pair according to the present invention are used, one specific for the target nucleic acid and one specific for the mutant nucleic acid.

In another embodiment of the present invention the oligonucleotide or oligonucleotide analogues according to the present invention or nucleic acids and/or nucleic acid analogues may be affixed to a solid support. Separation is then typically done by one or more washing steps under high-stringency conditions.

Some enzymes used for amplification are capable of degrading an oligonucleotide or oligonucleotide analogue if this is hybridised during amplification of the target nucleic acid. Such degradation can be used for detection of the presence of target nucleic acid.

It is therefore a preferred embodiment to provide an oligonucleotide or oligonucleotide analogue according to the present invention, where said oligonucleotide or oligonucleotide analogue is susceptible to nuclease activity by the enzyme used for amplification.

However enzymatic degradation also removes or lowers the possibility for doing an end-point melting and/or affinity measurement and hence the ability to verify the result by such a measurement.

It is therefore a more preferred embodiment of the present invention to provide an oligonucleotide or oligonucleotide analogue, comprising at least one hydrophobic molecule and a signalling pair according to the present invention, where the at least one hydrophobic molecule is positioned so that it would greatly inhibit enzymatic degradation of said oligonucleotide or oligonucleotide analogue by the used enzyme.

It is a more preferred embodiment of the present invention to provide an oligonucleotide or oligonucleotide analogue, comprising at least one hydrophobic molecule and a signalling pair according to the present invention, where the at least one hydrophobic molecule is positioned so that it would greatly inhibit enzymatic degradation of said oligonucleotides or oligonucleotide analogues by the used enzyme and so that the signal-to-noise ratio is enhanced when compared to the corresponding oligonucleotide or oligonucleotide analogue not comprising said hydrophobic group.

It is an even more preferred embodiment of the present invention if said oligonucleotide or oligonucleotide analogue are reasonably unchanged by said enzymatic step(s) and can be used for further verifications or reused for measurement.

Determining the Quantity of a Target Nucleic Acid and the Presence or Absence of a Mutation at a Polymorphic Site In one embodiment of the present invention the quantity of a target and mutant sequence is determined by the spectral properties of an assay comprising an oligonucleotide analogue comprising at least one hydrophobic molecule and a signalling pair after hybridization.

The detection can either detect the labelling pair attached to said oligonucleotide analogue or indirectly by detecting another label.

The presence or absence of a mutation according to the present invention may be determined using a number of different assays. Preferably, the assays involve either determining melting temperature or determining spectral properties or a mixture of both.

Accordingly, in one embodiment of the present invention the presence or absence of the mutation is determined by determining the spectral properties of the oligonucleotide analogue comprising at least one hydrophobic molecule after hybridization.

The spectral properties may be fluorescence properties, for example the spectral properties may be selected from the group consisting of monomer fluorescence excimer fluorescence, exciplex fluorescence, FRET and charge-transfer complex UV absorption band.

It is also possible to determine more than one spectral property, for example the spectral properties may be two or more selected from the group consisting of monomer fluorescence excimer fluorescence, exciplex fluorescence, FRET and charge transfer complex_fluorescence, in particular the spectral properties may be monomer fluorescence and excimer or exciplex or FRET or charged transfer fluorescence.

As discussed herein above, when the at least two parts in a signalling pair in an oligonucleotide analogue comprising at least one hydrophobic molecule are positioned in relation to each other so that they can form an intramolecular excimer, an intramolecular exciplex, FRET or a charge transfer complex, then when nucleobase pairs separating these two parts do base-pair that will preferably result in that said parts are not able to interact and hence form an intramolecular excimer, an intramolecular exciplex, FRET or a charge transfer complex. The hydrophobic molecules should ensure a significantly better interaction of the parts of a signalling pair in an oligonucleotide analogue that is unhybridized to its target sequence to make the intramolecular excimer, intramolecular exciplex, FRET or charge transfer complex stronger than without the presence of the hydrophobic molecules, so that when nucleobase pairs separating said two parts of the signalling pair do base-pair, the change in the intramolecular excimer, intramolecular exciplex, FRET or charge transfer complex should be significantly greater than if the hydrophobic molecule(s) are not present.

Accordingly, when the parts in a signalling pair in an oligonucleotide analogue comprising at least one hydrophobic molecule are positioned in relation to each other so that they can form intramolecular excimer, an intramolecular exciplex, FRET or a charge transfer complex, low or essentially no excimer fluorescence, exciplex fluorescence, FRET or charge-transfer complex UV emission band may be indicative of the absence of a target nucleic acid, and high excimer fluorescence, exciplex fluorescence, FRET or charge-transfer complex UV emission band may be indicative of the presence of a target nucleic acid or visa versa.

EXAMPLES

The following examples illustrate selected embodiments of the invention and should not be regarded as limiting for the invention.

In the examples the following abbreviations are used:
ODN: Oligodeoxynucleotide

Example 1

In this example is shown how molecules are drawn to calculate their SMILES notation and ALOGPs value using the program ALOGPS 2.1.

The molecules are visualized by using ACD/Labs 8.00 Release. Product version 8.17, Build 04, May 2005.

The hydrophobic molecules ALOGPs values are calculated with the attachment of a methyl group, where the molecule is normally attached to a linker or backbone monomer unit when said molecule is comprised in a nucleotide analogue, such as a hydrophobic nucleotide. The attachment points shown here are not meant to be limiting in any way. The reason for attaching a methyl group is because a linker or backbone monomer unit is often attached to a group that is highly dipolar when it is not fully substituted such as the N—H bond. This would then give the wrong impression on the hydrophobicity if for example said N—H bond is not present in the nucleotide or pseudonucleotide comprising the hydrophobic molecule.

ALOGPs values of natural nucleobases with a methyl group added at the normal site of conjugation to the backbone monomer unit:

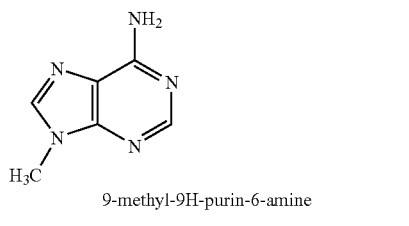

9-methyl-9H-purin-6-amine

SMILES: C12=NC=NC(N)=C1N=CN2C

ALOGPS = -0.12

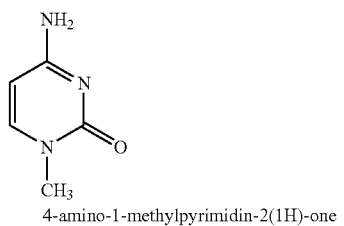

4-amino-1-methylpyrimidin-2(1H)-one

SMILES: C1(=O)N(C)C=CC(N)=N1

ALOGPs = -0.63

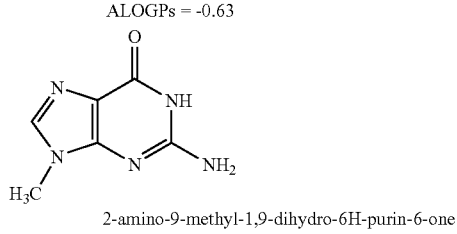

2-amino-9-methyl-1,9-dihydro-6H-purin-6-one

SMILES: C12=C(N=CN1C)C(=O)NC(N)=N2

ALOGPS = -0.93

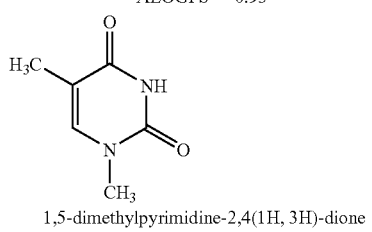

1,5-dimethylpyrimidine-2,4(1H, 3H)-dione

SMILES: C1(=O)N(C)C=C(C)C(=O)N1

ALOGPs = -0.63

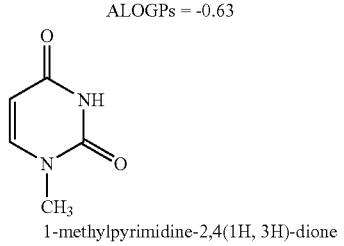

1-methylpyrimidine-2,4(1H, 3H)-dione

SMILES: C1(=O)N(C)C=CC(=O)N1

ALOGPs = -0.85

The structures above from left to right are the methylated nucleobases: Adenine, Cytosine, Guanine, Thymine and Uracil. As it can be seen from the above all nucleobases have an ALOGPs value below 0 and hence are not hydrophobic molecules according to the present invention.

ALOGPs values of hydrophobic, aromatic intercalators with a methyl group added at the normal site of conjugation to a linker or backbone monomer unit. The positioning of the methyl group is not important in the examples shown here. Any of these may be hydrophobic molecules according to the invention:

ALOGPs:

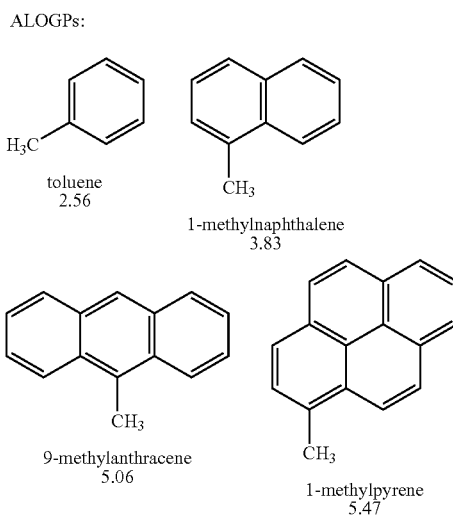

As can be seen from the above, the larger the conjugated systems are the higher ALOGPs value.

ALOGPs values of hydrophobic, heteroaromatic intercalators with a methyl group added at the normal site of conjugation to a linker or backbone monomer unit. Any of these may be hydrophobic molecules according to the invention.

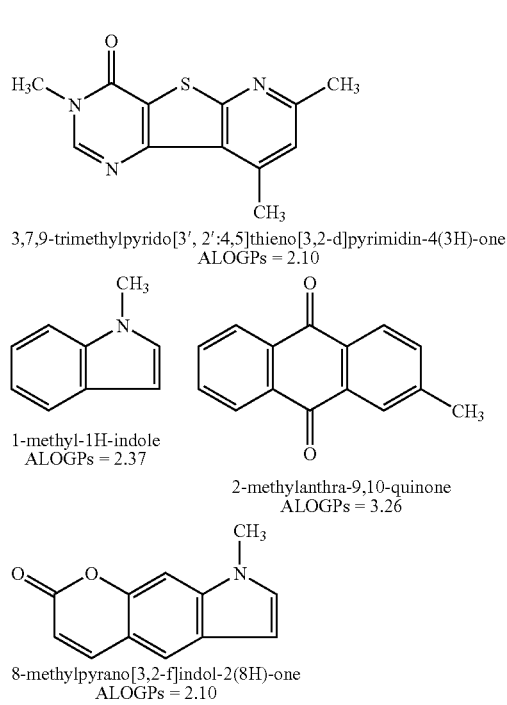

ALOGPs values of hydrophobic, alkanes and alkenes.

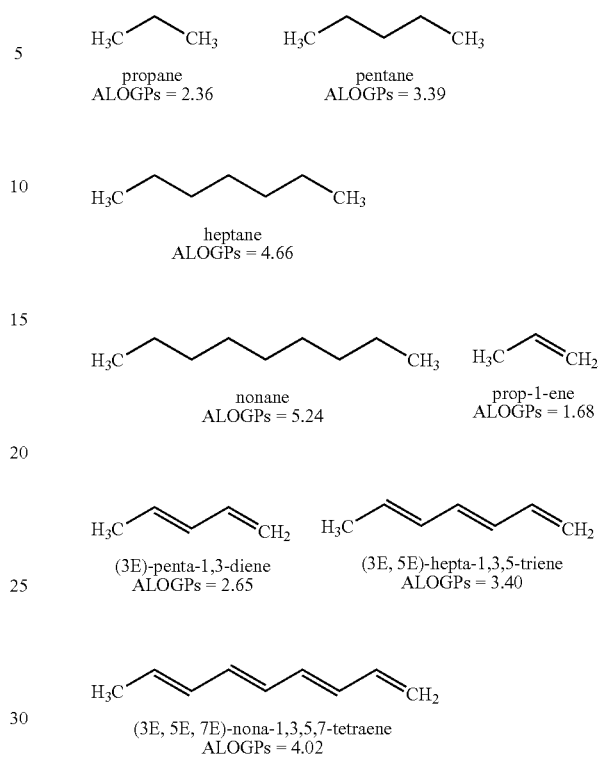

As can be seen the ALOGPs value increases with increasing length of alkanes and alkenes.

ALOGPs values and SMILES notation of the hydrophobic part of some Blackhole quenchers, BHQ:

BHQ0

SMILES: C3(N═NC2═CC(C)═══C(N═NC1═CC═══C(N(C)C)C ═══C1)C═C2)═══C(C)C═CC═══C3

ALOGPs = 6.46

It can be seen that the quenchers illustrated above are hydrophobic and all the shown examples have a ALOGPs value over 2. This is the reason why a hydrophobic molecule according to the present invention can increase the interaction of a fluorophore and a hydrophobic quencher in respective ends of a Stemless Beacon by being positioned in the same half as the fluorophore. Hydrophobic interactions between the quencher and the hydrophobic molecule can bring the fluorophore and quencher into close proximity—reducing the background fluorescence.

ALOGPs values and SMILES notation for the signal generating part of some fluorophores:

BHQ1

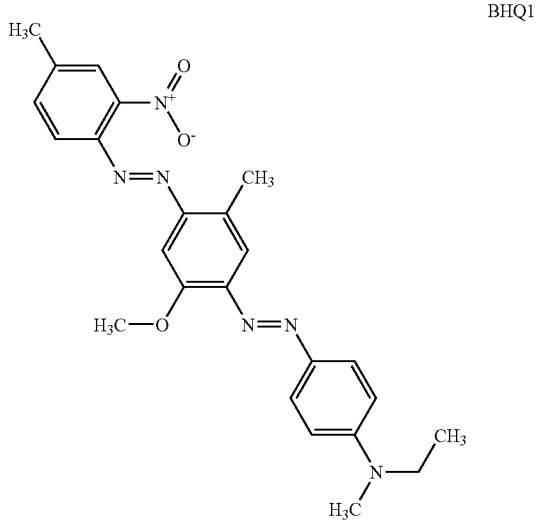

SMILES: C3(N=NC2=CC(OC)=C(N=NC1=CC=C(N(C)CC)C=C1)C=C2C)=C(N(=O)=O)C=C(C)C=C3
ALOGPs = 6.64

BHQ2

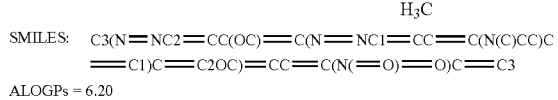

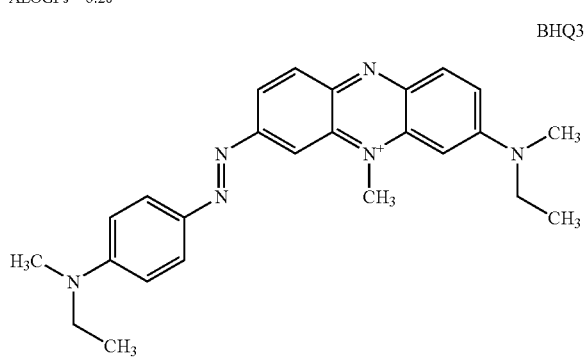

SMILES: C3(N=NC2=CC(OC)=C(N=NC1=CC=C(N(C)CC)C=C1)C=C2OC)=CC=C(N(=O)=O)C=C3
ALOGPs = 6.20

BHQ3

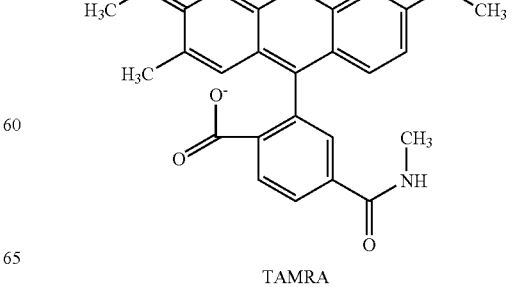

SMILES: C12=CC(N(CC)C)=CC=C1N=C4C(=[N+]2C)C=C(N=NC3=CC=C(N(C)CC)C=C3)C=C4
ALOGPs = 2.37

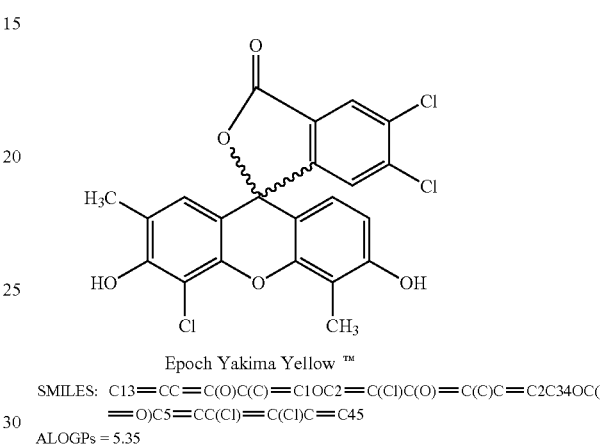

Epoch Yakima Yellow ™
SMILES: C13=CC=C(O)C(C)=C1OC2=C(Cl)C(O)=C(C)C=C2C34OC(=O)C5=CC(Cl)=C(Cl)C=C45
ALOGPs = 5.35

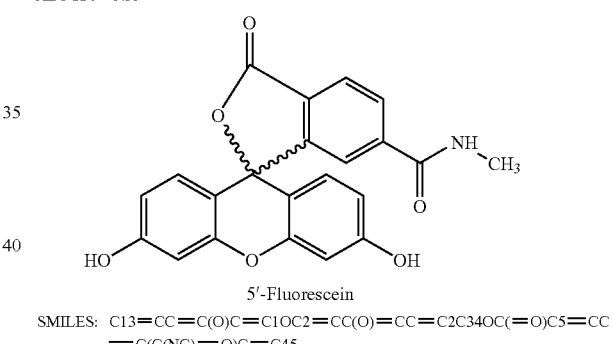

5'-Fluorescein
SMILES: C13=CC=C(O)C=C1OC2=CC(O)=CC=C2C34OC(=O)C5=CC=C(C(NC)=O)C=C45
ALOGPs = 2.48

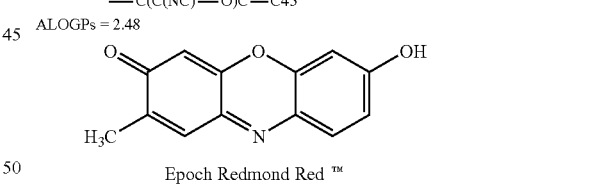

Epoch Redmond Red ™
SMILES: C13=CC=C(O)C=C1OC2=CC(=O)C(C)=CC2=N3
ALOGPs = 2.08

TAMRA

-continued

SMILES: C13═CC═C(N(C)C)C═C1OC2═CC(═[N+](C)C)C(C)═CC2
═C3C4═C(C([O-])═O)C═CC(C(═O)NC)═C4

ALOGPs = -0.15

It can be seen that some of the fluorophores illustrated above are hydrophobic according to the present invention with ALOGPs values above 0. Hydrophobic molecules according to the present invention can increase the interaction of a hydrophobic fluorophore and a quencher in respective ends of a Stemless Beacon by being positioned in the same half as the quencher. Hydrophobic interactions between the fluorophore and the hydrophobic molecule will lower the background fluorescence.

Example 2

Low Background Fluorescence

The measurement was done as a melting temperature experiment on a Mx3000, Stratagene Real-time PCR instrument in a 96-well plate. The measurements were done in a buffer solution reflecting the buffer solutions used in a normal Real-time PCR reaction. The buffer contained 4 mM $MgCl_2$, 50 mM KCl, 10 mM TRIS-HCl, pH=8.0. 1 μL of the Stemless Beacon (5 pmol/μL) and 2 μL of the DNA target sequence (5 pmol/μL) and 22 μL of the buffer mentioned above. First the mixtures were heated to 95° C. for 1 min to denature the secondary structures followed by annealing of the duplexes at 35° C. and ramping up to 95° C. while measuring the signal for every degrees change. Results are shown in FIG. 2, and other details like the sequences of the Stemless Beacons can be seen in the legend to said Figure.

As can be seen from FIG. 2, the Stemless Beacon has significantly reduced background fluorescence compared to the Stemless DNA probe (fluorescence of unbound probe) with both probes having the same maximum fluorescence (at 35° C.). It is also clear that the background fluorescence (or noise) of the Stemless Beacons comprising hydrophobic molecules is low over the entire temperature range, while the background fluorescence of the DNA based probe is higher at lower temperature. This is properly due to the reduced movement of the probe at lower temperature resulting in less frequent "collisions" of the fluorophore and quencher.

The two probes in the example are designed to distinguish between a methylated and unmethylated target of a bisulphite treated DNA sample. The preferred reading temperature for that probe during a RT-PCR run is midway between the melting temperature of the probe against the fully matched target (67° C.) and the mismatched target (56° C.), so in this case it would be 62° C. It is therefore important that the probe has a good signal-noise ratio at the reading temperature. The Signal-Noise ratio is calculated as follows:

$$\frac{\text{Signal(Probe + Matched target) at annealing} - \text{Buffer signal at annealing}}{\text{Signal(Probe + Mismatched target) at annealing} - \text{Buffer signal at annealing}}$$

In the example shown in FIG. 1 the signal-to-noise ratios at 62° C. would be:

$$S/N \text{ ratio Stemless DNA } \frac{43.2 - 0.2}{20.7 - 0.2} = \underline{2.1}$$

$$S/N \text{ ratio Stemless Beacon } \frac{41.1 - 0.2}{5.9 - 0.2} = \underline{7.0}$$

Example 3

High Affinity and Specificity of Some Stemless Beacons

The Measurements were carried out as described in example 2 above. Result and sequence information can be found in FIG. 3 and in the legend to said figure. The results are shown as the first derivative of the signal against temperature.

Figure 3:
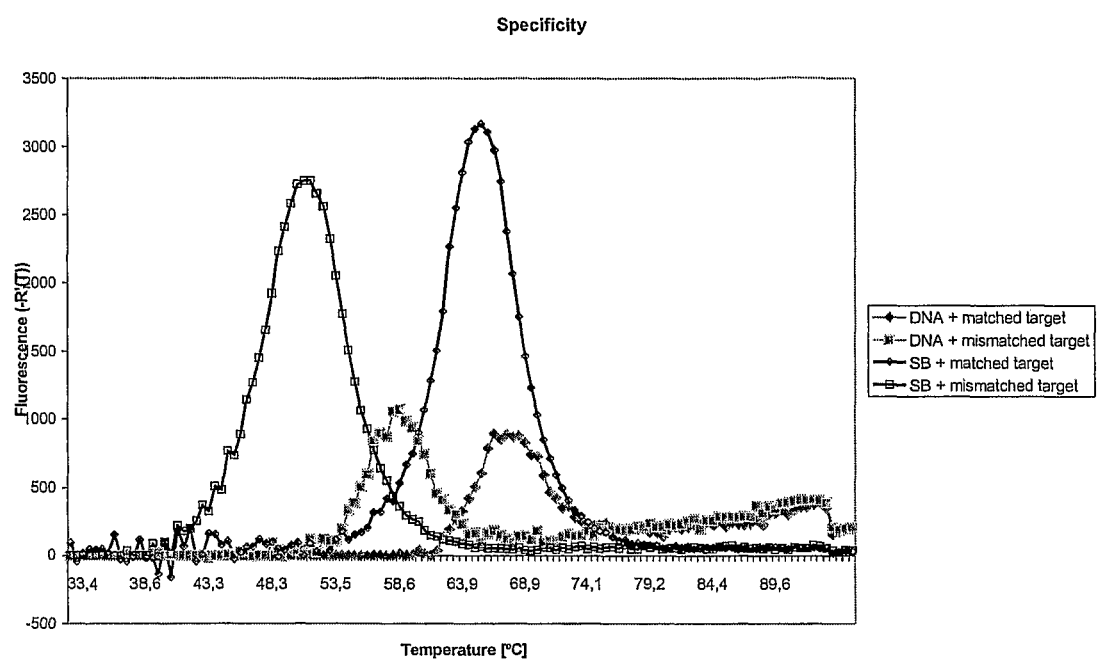

FIG. 3 demonstrates that Stemless Beacons with insertions of intercalating hydrophobic molecules can be designed to achieve a higher specificity than their DNA counterparts. In the example shown the Stemless Beacon, SB, hybridizes at 63.7° C. and 49.9° C. with its matched and mismatched targets respectively giving a 13.8° C. difference, while the DNA hybridizes at 64.9° C. and 57.1° C. with its matched and mismatched target respectively giving only 7.8° C. difference. The specificity is therefore 77% higher for this Stemless Beacon over a Stemless DNA probe having the same affinity for a target sequence, measured as the difference in affinity to a matched versus a mismatched target.

Example 4

Test and Optimisation of Primers and Probes During PCR Assay

The protocol described in this example is for distinguishing between two genotypes A and B using Real-Time PCR instruments that are capable of making multiple readings (more than 4 readings in a cycle). Instruments in this category includes Stratagenes real-time PCR instrument Mx3000P, which has been used in this study.

By using the procedure described below it is possible to test if the primers work at the selected annealing temperature with the template whilst also optimising the reading temperature for both probes individually. The measurement itself can be used for distinguishing between closely related genotypes.

1. To an optical PCR-tube add 10 μL of 2×PCR Mastermix, 1 μL of the forward primer (10 pmol/μL), 1 μL of the reverse primer (10 pmol/μL), 1 μL of the Stemless Beacon (5 pmol/μL) specific for genotype A, 1 μL of the Stemless Beacon (5 pmol/μL) specific for genotype B, 5 μL of $H_2O$ and 1 μL of DNA (100 pG-20 nG/μL).
2. If available make two tubes for each target of interest as described above, one with Genotype A, and one with genotype B. If these controls are not available, just prepare the tubes with an unknown sample.
3. Close the tubes with optical lids (if using a Real-time PCR machine that measures the fluorescence through the lid, as most models do) or just a standard lid, if using a machine that reads through the side or bottom of the tube.

Figure 6:
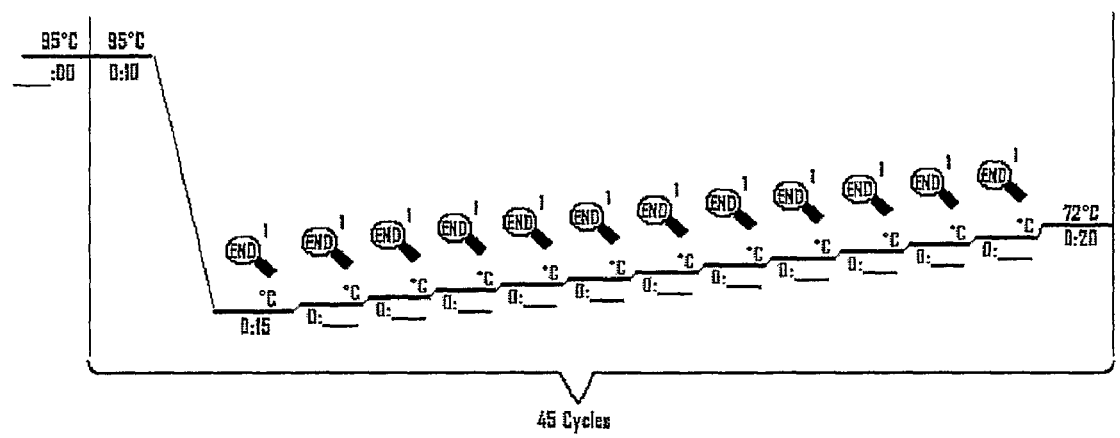

4. Place the tubes in the Real-time PCR machine and run the following program (illustrated in FIG. 6):
   a. If using a hot-start polymerase, activate this according to manufactures description, otherwise just heat at 95° C. for 1 min. to get rid of secondary structures; and
   b. Follow the activation by 45 cycles using the following steps:
      i. Denature at 95° C. for 30 sec; and
      ii. Anneal the primers and probes (e.g. at 50° C.) for 1:00 min, endpoint or continuously fluorescence measurement; and
      iii. Increase the temperature by 2° C. and make endpoint fluorescence measurement. Use as short a time interval as possible (dependent on the number and positions of samples); and
      iv. Repeat step ii until approx. 70° C. is reached; and
      v. Elongate at 72° C. for 30 sec; and
5. Analyse data—The optimal fluorescence reading temperature for that probe to use in future Real-time PCR experiments of that target is where the Stemless Beacon hybridised to the fully complementary target only and has as high a signal as possible. A separate reading temperature is found for both probes.

An example of the difference in fluorescence at different temperature stages and how this protocol is used for optimising the future RT-PCR runs of that particular target can be seen in FIG. 8. This example also illustrates multiplexing with two Stemless Beacons in a single closed tube.

Example 5

Test and Optimisation of Primers and Probes, Endpoint Determination

This section describes how an endpoint affinity measurement can be used for optimising Stemless Beacons according to the present invention and for distinguishing between two genotypes A and B. This method is especially suitable on Real-Time PCR instruments with high ramp rates such as e.g. Corbett Research's Rotorgene™ 3000, Applied Biosystems 7500 Fast Real-Time PCR System, and other fast ramping Real-Time PCR instruments with a ramp (cooling) rate of ≧3° C./sec, but can also be carried out on standard Real-time PCR instruments. Measurements based on this procedure in this example were carried out on a Corbett Research's Rotorgene™ 3000.

Figure 7:
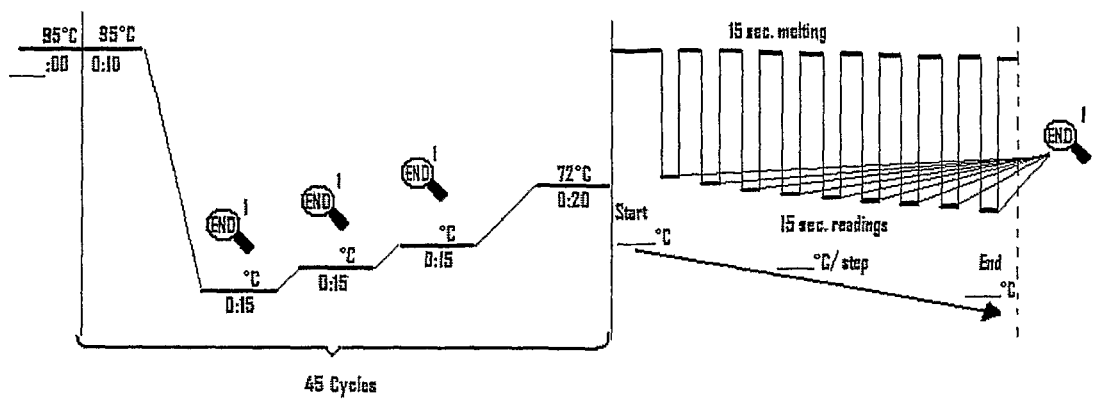

1. To an optical PCR-tube is added 10 μL of 2×PCR Mastermix, 1 μL of the forward primer (10 pmol/μL), 1 μL of the reverse primer (10 pmol/μL), 1 μL of a the Stemless Beacon (5 pmol/μL) specific for genotype A, 1 μL of a the Stemless Beacon (5 pmol/μL) specific for genotype B, 5 μL of H₂O and 1 μL of DNA (100 pG-20 nG/μL); and
2. If available make two tubes for each target of interest as described above, one with genotype A comprising DNA, and one with genotype B comprising DNA. If these controls are not available, just prepare the tubes with an unknown sample; and
3. Close the tubes with optical lids (if using a Real-time PCR machine that measures the fluorescence through the lid, as most models do) or just a standard lid, if using a machine that reads through the side of the tube as the Rotorgene™, Corbett Research Pty Ltd, Australia, does; and
4. Place the tubes in the Real-time PCR machine and run the following program (illustrated in FIG. 7):
   a. If using a hot-start polymerase, activate this according to manufactures description, otherwise just heat at 95° C. for 1 min. to get rid of secondary structures; and
   b. Follow the activation by 45 cycles of amplification using the following steps (see Note 8):
      i. Denature at 95° C. for 10 sec; and
      ii. Anneal the primers and probes (e.g. at 50° C.) for 15 sec, read endpoint fluorescence; and
      iii. Optionally read fluorescence at additional one or two temperatures; and
      iv. Elongate at 72° for 20 sec; and
   b. Make an endpoint affinity test the following way:
      i. Denature at 95° C. for 15 sec; and
      ii. 15 sec annealing at 1° C. lower than the previous annealing, starting at 72° C. Read endpoint fluorescence; and
      iii. Repeat above two steps 27 times (72° C. to 45° C.); and
5. Analyse data—The best fluorescence reading temperatures to use in future Real-time PCR experiment of that target is midway between the temperatures where the fluorescence of the Stemless Beacon hybridised to the fully complementary target starts to "take off" and the temperature where the fluorescence of the Stemless Beacon hybridised to the mismatched target starts to "take off". The found temperatures can be used as reading points in future measurements using the same setup. Affinity measurement like the one described here is a very sensitive way to distinguish between similar targets.

Figure 9:
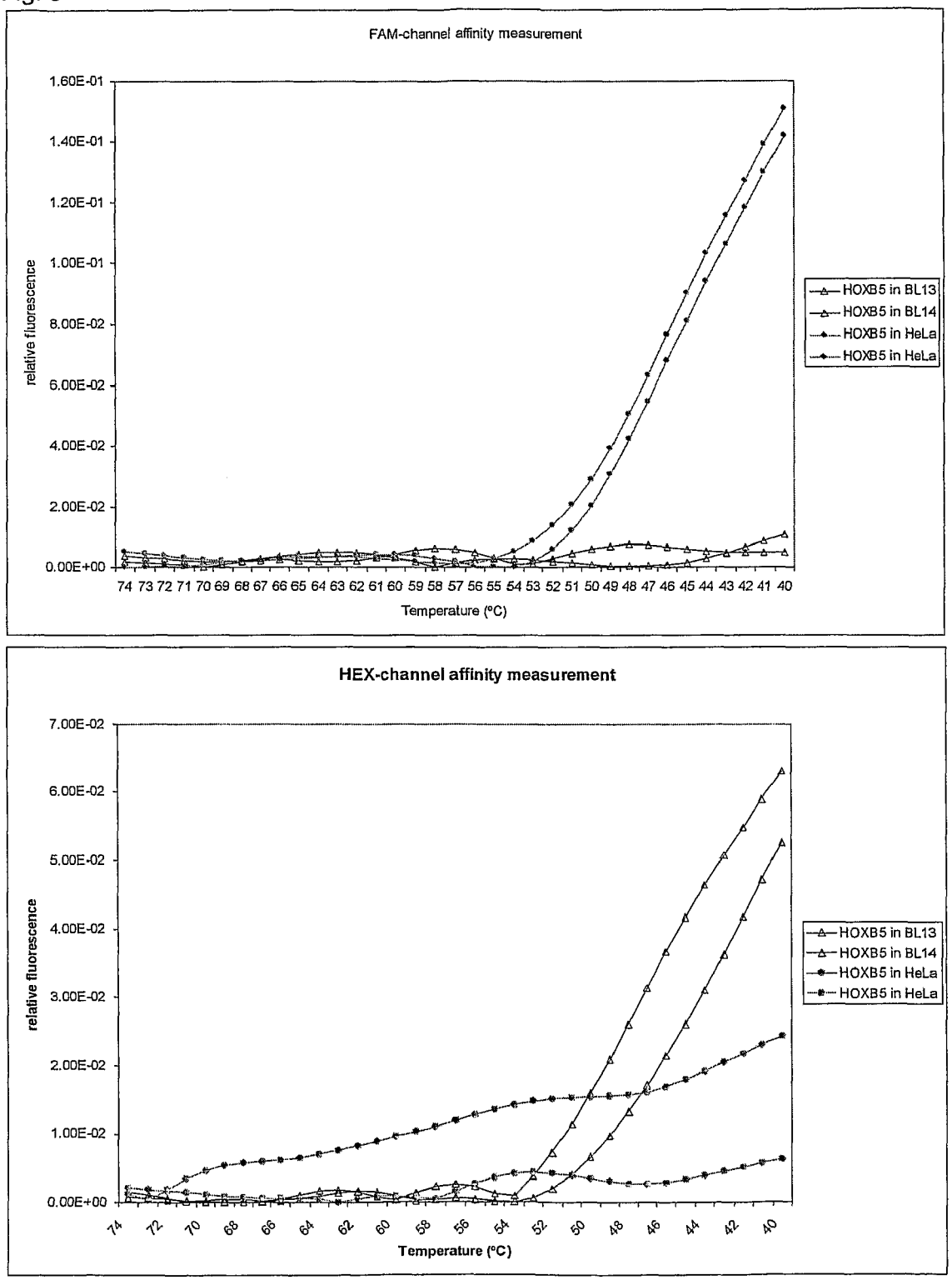

An example of how the endpoint, affinity measurement can be used for optimisation of future RT-PCR runs for the same target and how the affinity measurement is very powerful in distinguishing between two very similar targets can be seen in FIG. 9.

Example 6

Detection of Methylation Status of a Single CpG in HOXB5

A test was setup to see if it was possible to distinguish between methylated, unmethylated and the "heterozygote" of a single CpG site in the gene HOXB5. Measurements in this example were carried out on a Corbett Research's Rotorgene™ 3000.

Target, Primers and Probes

```
                                          [SEQ ID NO. 10]
Forward primer:
5'-1TTTGTTTAGAGGTTAAAGTTAATTTTT

[SEQ ID NO. 11]
Reverse primer:
5'-1TCAAAAAATAATTCATACTCTATAATTAC

[SEQ ID NO. 12]
Unmethylated specific probe:
HEX-TT1AAAAAC1CAATTC1AAT1A-BHQ1

[SEQ ID NO: 13]
Methylated specific probe:
FAM-TT1GAATCG1GTTT1T-BHQ1
```

The target sequence was comprised in a pre-amplified bisulphite treated DNA (outer primers:

```
                              [SEQUENCE ID NO. 14]
5'-1GGGAGTTAGTAGGGAGGTAGT
and

[SEQUENCE ID NO. 15]
5'-1TAAAAAATCACRTACTTTTATTAACC)
``` from either HeLa or BL13. Sequencing data had previously shown that HeLa to be methylated at the polymorphic site of interest, while BL13 was shown to be unmethylated. 36 samples of comprising target DNA were prepared 12 of each: pure HeLa, pure BL13 or a 1:1 mixture of HeLa and BL13 bisulphite treated DNA. The target was used in 4 different dilutions 3 of each; diluted 10, 100, 1,000 or 100,000 times. The label 1 means the inserted pseudonucleotide, i.e. the hydrophobic nucleotide (Phosphoramidite of (S)-1-(4,4'-dimethoxytriphenylmethyloxy)-3-pyrenemethyloxy-2-propanol) comprising the hydrophobic and intercalating molecule pyrene. FAM and Hex are fluorophores and BHQ1 is a quencher.

QPCR Setup

| | |
|---|---|
| Forward primer | 1 µL (10.0 pmol/µL) |
| Reverse primer | 1 µL (10.0 pmol/µL) |
| Probe (FAM) | 1 µL (12.5 pmol/µL) |
| Probe (Hex) | 1 µL (12.5 pmol/µL) |
| H$_2$O | 5 µL |
| 2 × Mastermix, Promega | 10 µL |
| DNA template | 1 µL (see above for dilution information) |

Real-Time PCR Profile

Figure 14A:
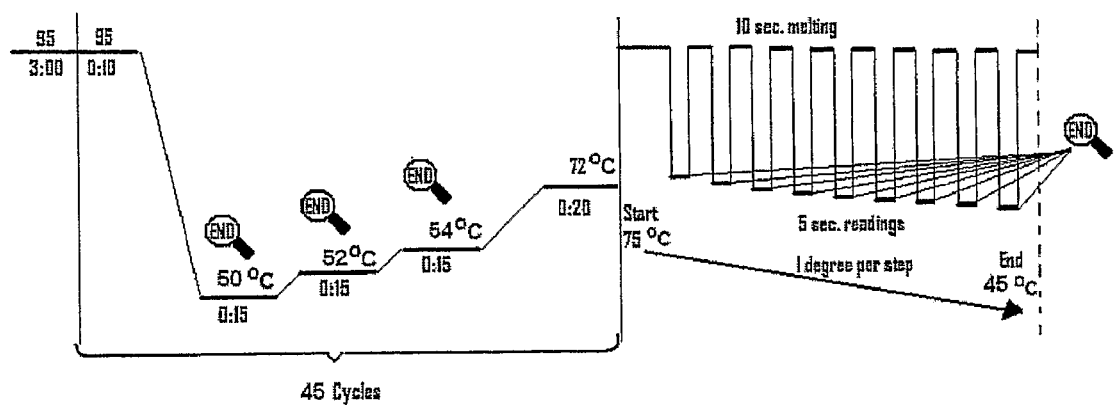

The real-time PCR profile used is depicted in FIG. 14A.

Results

Using either the fluorescence measurements during the real-time PCR it was possible to correctly assign all except one samples. All samples were assigned correctly using the affinity analysis. One sample didn't amplify.

Example 7

Detection of a SNP in Nucleotide 2074 of Human Andrenogen Receptor

A test was setup to see if the used combination of probes would be able to distinguish between the wildtype and the A→G transition mutant. Measurements in this example were carried out on the Real-time PCR machine Rotorgene™ 3000 from Corbett Research.

Target, Primers and Probes

```
                                  [SEQ ID NO. 16]
Forward primer      5'-TCCCACATCCTGCTCAAG

[SEQ ID NO. 17]
Reverse primer      5'-ATCTCTGCCATCATTTCCG

[SEQ ID NO. 18]
Wt specific probe   FAM-T1CAAA1AGTGA1ACTG1AT-BHQ1

[SEQ ID NO. 19]
Mut. specific probe HEX-2TCAAA2AGCGA2ACTG2AT-BHQ1
```

In this experiment the mut. specific probe was added together with wt. specific probe in a homogenous assay. The label 1 means the inserted pseudonucleotide or hydrophobic nucleotide (Phosphoramidite of (S)-1-(4,4'-dimethoxytriphenylmethyloxy)-3-pyrenemethyloxy-2-propanol) compris- ing the hydrophobic, intercalating molecule pyrene (with the number XII from the description above). The label 2 means the inserted pseudonucleotide or hydrophobic nucleotide (Phosphoramidite of 3-(1-O-(4,4'-dimethoxytriphenylmethyl)-2-O-(2-cyanoethyl diisopropylamidophosphite)-1,2-butandiol)-4-N-(7,9-Dimethyl-3H-pyrido[3',2':4,5]thieno[3,2-d]pyrimidin-4-one)) (comprising the intercalating hydrophobic group with the number XXVI from the description above). FAM and Hex are fluorophores and BHQ1 is a quencher.

The template: 2 samples of each with cDNA extracted from either LNCap (mutant) and/or THP (wt) (6 samples overall).

QPCR Setup

| | |
|---|---|
| Forward primer | 1 µL (10.0 pmol/µL) |
| Reverse primer | 1 µL (10.0 pmol/µL) |
| Probe (FAM) | 1 µL (12.5 pmol/µL) |
| Probe (Hex) | 1 µL (12.5 pmol/µL) |
| H$_2$O | 5 µL |
| 2 × Mastermix, Promega | 10 µL |
| DNA template | 1 µL |

Real-Time PCR Profile

Figure 14B:
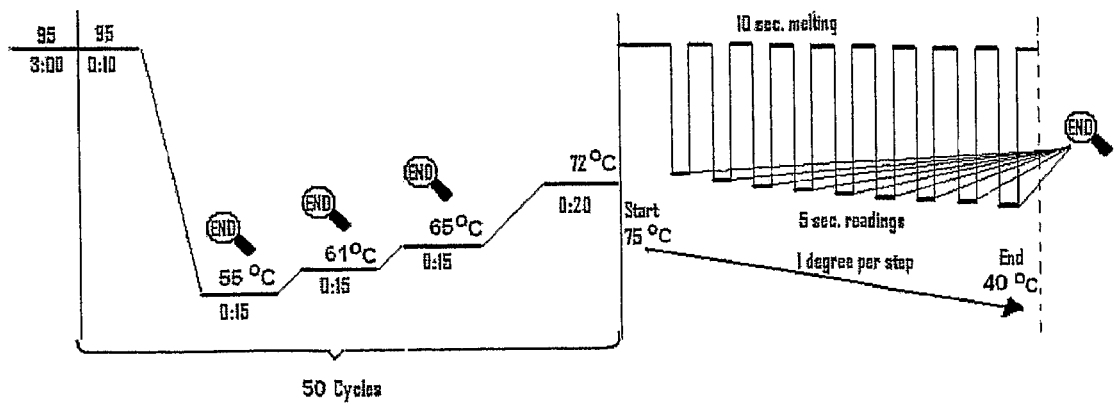

The Real-Time PCR profile used is depicted in FIG. 14B.

Results

At 55° C. wt specific probe binds to both the wild type target and the mutant, while the mut. Specific probe is hybridising specifically to its target.

At 61° C. wt the threshold can be adjusted so that only a specific signal from wt probe is obtained, while the mut. specific probe worked fine.

At 65° C. the wt. specific probe is only binding to its specific target, while the mut. Specific probe is no longer binding.

End-point affinity measurements on FAM channel showed that there is an approximately 5 degree window (from 61 to 66° C.) where the wt specific probe is only hybridizing to the THP cDNA and not the LNCap.

End-point affinity measurements on HEX channel showed that it was very easy to distinguish binding to the fully complementary target over the single nucleotide mismatched target using the mut. Specific probe with a window of at least 10° C. at temperatures above 55° C.

Conclusions

The probes used in combination are able to detect a A→G transition found at nucleotide 2074 in the human Andrenogen receptor. The FAM-labelled probe is specific in the 61 to 66° C. window, while the HEX labelled probe is specific at temperatures between 55 and 63° C.

It is again shown that an end-point affinity study as described herein can be used for the specific detection of very small changes in a nucleic acid. The method is a homogenous one, where the amplification can be done at its optimal conditions followed by the affinity measurement.

Example 8

Real-Time PCR and Positioning of Hydrophobic Nucleotides

Introduction

This example illustrates the fluorescent signal strength in relation to the positioning of hydrophobic nucleotides.

Materials

| Reagents | Vol/reaction | Concentrations |
|---|---|---|
| Forward primer | 2.00 µL | 2 nmol/mL |
| Reverse Primer | 2.00 µL | 2 nmol/mL |
| 2 × Promega Mastermix | 10.00 µL | — |
| pCH110 betagal WT template Pubmed ID 595693 | 2.00 µL | Variable |
| Betagal probe | 4.00 µL | 1 nmol/mL |
| Total vol/reaction | 20.00 µL | — |

Probes, Primers of Target Sequences

```
                                             [SEQ ID NO: 20]
Bgalprob_01:  5'-Fam 1AC CGA CCC AGC GCC C1 BHQ1-3'

[SEQ ID NO: 21]
Bgalprob_02   5'-Fam A1C CGA CCC AGC GCC 1C BHQ1-3'

[SEQ ID NO: 22]
Bgalprob_03:  5'-Fam AC1 CGA CCC AGC GC1 CC BHQ1-3'
```

1=Hydrophobic nucleotide of the structure X—Y-Q where X is a backbone monomer unit linked to the oligo by phosphordiester bonds and of the structure —O—$CH_2$—$CH_2$—O—, Y is a —$CH_2$—O—$CH_2$— linker and Q is 1'-pyrene.
Primere

```
                                             [SEQ ID NO: 23]
Bgal_SNP01_F: 5'-CGG TTA CGA TGC GCC CAT CTA CAC-3'

[SEQ ID NO: 24]
Bgal_SNP01_R: 5'-CAG CAC CAT CAC CGC GAG GC-3'
```

Results/Conclusion

As can be seen from FIG. 10, the positioning of IPNs as neighbours to the signaling pair reduces the fluorescent signal significant. However just having one nucleotide between the signaling pair and the first hydrophobic nucleotide improves the signal significant and having two nucleotides between produces even a higher signal. It is therefore a preferred embodiment of the present invention not to have hydrophobic nucleotides as next nearest neighbours to the (fluorophore part) signaling pair.

Example 9

End-Point Addition and Detection of Target

Introduction

This example illustrates how the addition of probes to a target nucleic acid can be used for the detection of the presence of said target nucleic acid.
Materials and Methods First a target nucleic acid was amplified using the specified primers and mastermix:

| Reagents | Vol/reaction | Concentrations |
|---|---|---|
| Forward primer | 2.00 µL | 2 nmol/mL |
| Reverse Primer | 2.00 µL | 2 nmol/mL |
| 2 × Promega Mastermix | 10.00 µL | — |
| $H_2O$ | 4.00 µL | |
| pCH110 betagal WT template Pubmed ID 595693 | 2.00 µL | Variable |
| Total vol/reaction | 20.00 µL | — | and subjecting the mixture for the amplification profile indicated below:

| Cycle | Cycle Point |
|---|---|
| Hold @ 95° c., 2 min 0 secs | |
| Cycling (50 repeats) | Step 1 @ 94° c., hold 10 secs |
| | Step 2 @ 60° c., hold 30 secs, acquiring to Cycling A([Green][1][1]) |

After the amplification profile, there was added 2.00 µL of the following probes to their respective amplification reactions (No 11 of the table below is the addition of no probe).

```
                                             [SEQ ID NO: 25]
Bgalprob_02   5'-Fam A1C CGA CCC AGC GCC 1C BHQ1-3'

[SEQ ID NO: 26]
Bgalprob_03:  5'-Fam AC1 CGA CCC AGC GC1 CC BHQ1-3'

[SEQ ID NO: 27]
Bgalprob_05:  5'-Fam ACC G1A CCC AGC 1GC CC BHQ1-3'

[SEQ ID NO: 28]
Bgalprob_ref: 5'-Fam ACC GAC CCA GCG CCC BHQ1-3'
```

1=Hydrophobic nucleotide of the structure X—Y-Q where X is a backbone monomer unit linked to the oligo by phosphordiester bonds and of the structure —O—$CH_2$—$CH_2$—O—, Y is a —$CH_2$—O—$CH_2$— linker and Q is 1'-pyrene.

And finally an affinity measurement, using the profile shown in the bottom of FIG. 11, was done.
Results and Conclusion From FIG. 11 it is clear that all the presented probes can be used for end-point detection of a target nucleic acid using the presented affinity measurement profile. It is also clear that the stemless beacons comprising hydrophobic nucleotides have a higher affinity to the target nucleic acid and a higher fluorescent signal strength than the DNA based probe.
Additional By comparing the following probes in a similar reaction:

```
                                             [SEQ ID NO: 29]
Bgalprob_01:  5'-Fam 1AC CGA CCC AGC GCC C1 BHQ1-3'

[SEQ ID NO: 30]
Bgalprob_05:  5'-Fam ACC G1A CCC AGC 1GC CC BHQ1-3'

[SEQ ID NO: 31]
Bgalprob_ref: 5'-Fam ACC GAC CCA GCG CCC BHQ1-3'
```

1=Hydrophobic nucleotide of the structure X—Y-Q where X is a backbone monomer unit linked to the oligo by phosphordiester bonds and of the structure —O—$CH_2$—$CH_2$—O—, Y is a —$CH_2$—O—$CH_2$— linker and Q is 1'-pyrene.

Figure 12:
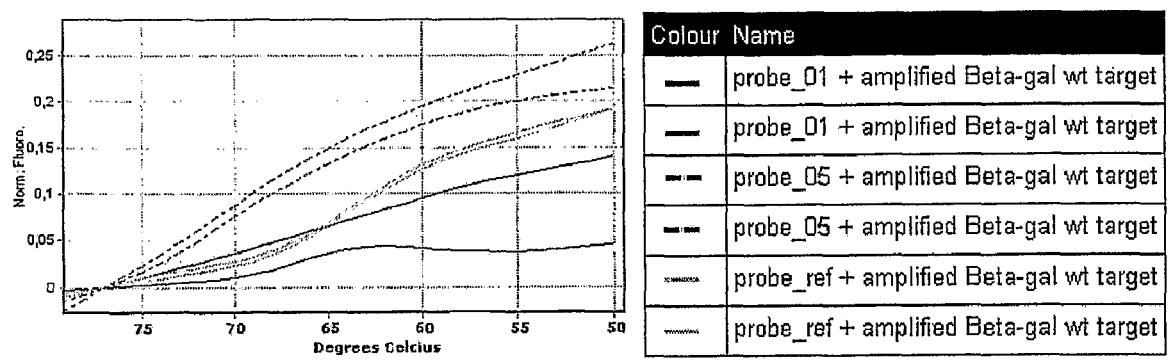
FIG. 12 shows results obtained as described in example 9.

It can be seen from FIG. 12, that the positioning of hydrophobic nucleotides as neighbours to the signaling pair reduces the fluorescent signal significant in this type of measurement also.

Example 10

Affinity of Stemless Probes to Single Stranded Oligo Target

Introduction

This example illustrates how stemless beacons comprising hydrophobic modifications of the structure: X—Y-Q where X is a backbone monomer unit linked to the oligo by phosphordiester bonds and of the structure —O—$CH_2$—$CH_2$—O—, Y is a —CH$_2$—O—CH$_2$— linker and Q is 1'-pyrene, will have higher affinity towards a fully complementary target sequence than a probe not comprising said hydrophobic modifications.

Materials and Methods

The following probes were tested:

```
                                                 [SEQ ID NO: 32]
Bgalprob_1:   5'-Fam 1AC CGA CCC AGC GCC C1 BHQ1-3'

[SEQ ID NO: 33]
Bgalprob_2    5'-Fam A1C CGA CCC AGC GCC 1C BHQ1-3'

[SEQ ID NO: 34]
Bgalprob_5:   5'-Fam ACC G1A CCC AGC 1GC CC BHQ1-3'

[SEQ ID NO: 35]
Bgalprob_6:   5'-Fam ACC GA1 CCC AG1 CGC CC BHQ1-3'

[SEQ ID NO: 36]
Bgalprob_7:   5'-Fam ACC GAC 1CC A1G CGC CC BHQ1-3'

[SEQ ID NO: 37]
Bgalprob_ref: 5'-Fam ACC GAC CCA GCG CCC BHQ1-3'
```

Oligo Target Sequence:

Bgal_WT_tar:   5'-AAC GGG CGC TGG GTC GGT TAC-3'

Profile

| Cycle |
|---|

Hold @ 94° c., 1 min 0 secs
Melt (25-90° c.), hold secs on the 1st step, hold 5 secs on next steps,
Melt A([Green][1][1])

Mixture

| | | |
|---|---|---|
| Oligo target | 2.00 µL | 1 nmol/mL |
| Betagal probe_1 to_8 plus_ref | 2.00 µL | 1 nmol/mL |
| Buffer (280 mM NaCl, 20 mM Na$_2$HPO$_4$) | 10.00 µL | |
| H$_2$O | 6.00 µL | |

Results and Conclusion

Figure 13:
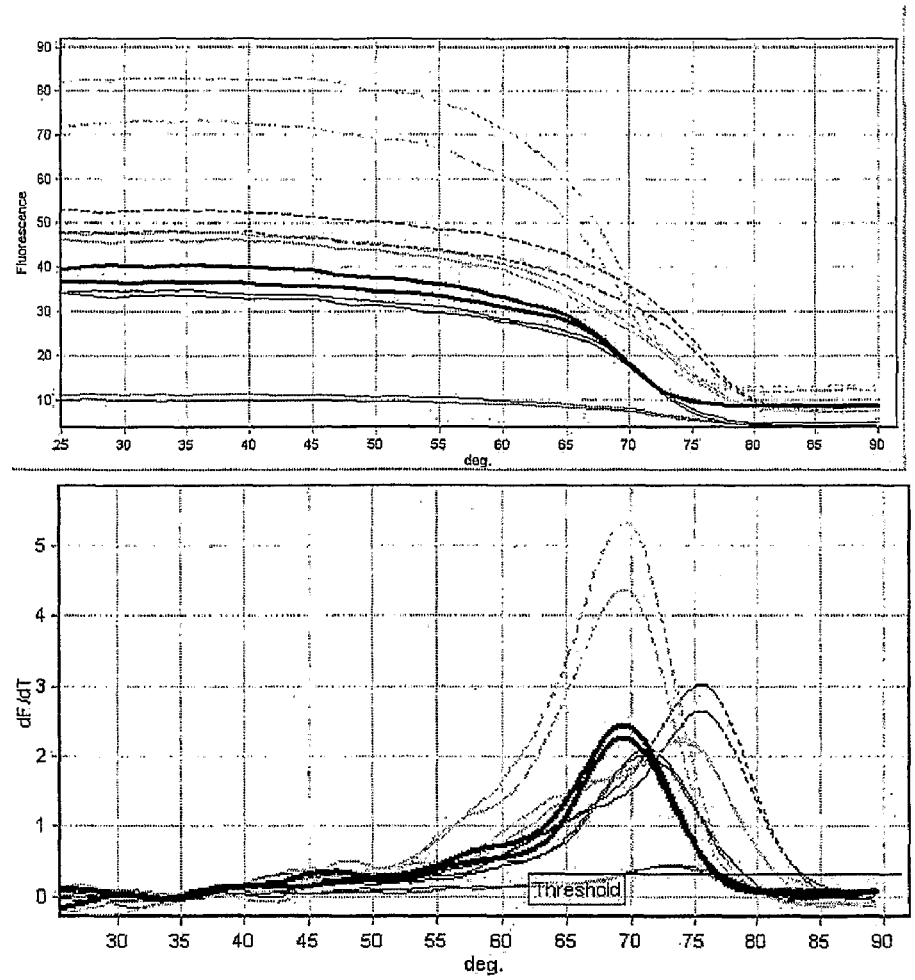
FIG. 13 shows the results obtained as described n example 10. The curves shows the results using the following probes:
-Probe_01-Probe_02-Probe_05-Probe_06-Probe_07
−Probe_ref FIGS. 14A and B illustrates real-time PCR profiles, which may be useful for the methods according to the invention.

It can be seen from FIG. 13 that all stemless beacons have the similar or higher affinity for the complementary oligo nucleotide target compared to the corresponding DNA. Furthermore it can be calculated that all of the stemless beacons presented in this example (exclusive probe_1) have a similar or higher signal-to-noise ratio than the DNA probe without hydrophobic modifications (signal at 25 degrees divided by signal at 90 degrees).

Signal-to-Noise Ratios:

| Probe number | Signal (25° C.) | Signal (90° C.) | Signal-to-noise |
|---|---|---|---|
| _2 | 34.12 | 4.7 | 7.26 |
| _5 | 50.57 | 7.81 | 6.48 |
| _6 | 77.01 | 12.85 | 5.99 |
| _7 | 46.92 | 7.98 | 5.88 |
| _ref (DNA) | 38.11 | 8.65 | 4.41 |

The invention claimed is:

1. An oligonucleotide analogue comprising a consecutive sequence of n nucleotides and/or nucleotide analogues and at least two hydrophobic nucleotides, wherein said oligonucleotide analogue is covalently linked to a signalling pair, wherein the hydrophobic nucleotide has the general structure

X—Y-Q wherein

X is a nucleotide or nucleotide analogue or a backbone monomer unit capable of being incorporated into the backbone of a nucleic acid or nucleic acid analogue, Q is a hydrophobic molecule which is not taking part in Watson-Crick hydrogen bonding; and Y is a linker moiety linking said nucleotide or nucleotide analogue or backbone monomer unit and said hydrophobic molecule; and wherein n is an integer of at least 4; and wherein the at least two hydrophobic nucleotides are positioned at the most 9 nucleotides and/or nucleotide analogues from at least one end of the oligonucleotide analogue; and wherein the hydrophobic nucleotide closest to the 3' end and the hydrophobic nucleotide closest to the 5' end of the oligonucleotide analogue are positioned in approximately the same distance from the respective parts of the signalling pair, and wherein the signalling pair consists of a two part system, wherein one part is positioned at the most 6 nucleotides and/or nucleotide analogues from the 5' end and the other part is positioned at the most 6 nucleotides or nucleotide analogues from the 3' end of the oligonucleotide analogue;

wherein the parts of the signalling pair are not identical to the hydrophobic nucleotide, with the proviso that when one part of the signalling pair is positioned as a dangling end at the 5' end of the oligonucleotide analogue, then the first nucleotide or nucleotide analogue at the 5' end is not a hydrophobic nucleotide and when one part of the signalling pair is positioned as a dangling end at the 3' end of the oligonucleotide analogue, then the first nucleotide or nucleotide analogue at the 3' end is not a hydrophobic nucleotide.

2. The oligonucleotide analogue according to claim 1 wherein at least one hydrophobic molecule, Q, has a logP value above 0 when a methyl group is added at the position of attachment to the linker, Y.

3. The oligonucleotide analogue according to claim 1, wherein at least one hydrophobic molecule, Q, is selected from the group consisting of polyaromates and heteropolyaromates optionally substituted with one or more selected from the group consisting of hydroxyl, bromo, fluoro, chloro, iodo, mercapto, thio, cyano, alkylthio, heterocycle, aryl, heteroaryl, carboxyl, carboalkoyl, alkyl, alkenyl, alkynyl, nitro, amino, alkoxyl and amido.

4. The oligonucleotide analogue according to claim 1, wherein the signaling pair is capable of a change in a detectable signal depending on the physical distance between the parts of the pair.

5. The oligonucleotide analogue according to claim 4, wherein one part of the signaling pair is a fluorophore and the other part of said signaling pair is a quencher, wherein said fluorophore and said quencher are capable of forming an intramolecular FRET complex.

6. The oligonucleotide analogue according to claim 1, wherein at least two of said hydrophobic nucleotides are positioned in opposite halves of said oligonucleotide analogue.

7. The oligonucleotide analogue according to claim 6, wherein the hydrophobic molecules of the hydrophobic nucleotides are capable of having hydrophobic interactions with each other thereby bringing the two parts of the signalling pair into close proximity within 40 Å.

8. The oligonucleotide nucleotide analogue according to claim 7, wherein no hydrophobic nucleotide is positioned closer to the 5' end than a part of the signalling pair and no hydrophobic nucleotide is positioned closer to the 3' end than the other part of the signalling pair.

9. The oligonucleotide analogue according to claim 1, wherein the oligonucleotide is immobilized to a solid support.

10. A method of detecting and/or quantifying hybridisation between an oligonucleotide analogue according to claim 1 and a target sequence during amplification, said method comprising the steps of a) providing a mixture of nucleic acids, which potentially comprises a target sequence; and b) providing an amplification buffer comprising an amplification enzyme, a set of primers, and an oligonucleotide analogue according to claim 1, wherein said primers and said oligonucleotide analogue are capable of hybridizing with said target sequence or a sequence complementary thereto, said amplification enzyme is capable of extending a primer in a template directed manner and said amplification buffer provides conditions for the amplification enzyme to perform such an extension in the presence of primers and template; and c) incubating the primers and oligonucleotide analogue with the mixture of nucleic acids under conditions allowing for hybridization of said primers; and d) extending the 3' end of said hybridized primers using the target sequence as template using said amplification enzyme; and e) incubating the nucleic acids, extension products and the oligonucleotide analogue under conditions allowing for hybridisation; and f) detecting hybridisation and optionally quantifying hybridisation; and g) optionally repeating step c) to f).

11. The method according to claim 10, wherein nuclease activity removes the most 5' part of the signaling pair.

12. The method according to claim 10, wherein the oligonucleotide analogue is complementary to said target sequence and able to differentiate between said target and any other sequences.

13. The method according to claim 10, wherein at least two oligonucleotide analogues according to claim 1 are provided, wherein one of said oligonucleotide analogues is complementary to one genotype of the target sequence and the other of said oligonucleotide analogues is complementary to another genotype of said target sequence.

14. The method according to claim 13, wherein the two genotypes differ by a single nucleotide polymorphism at a polymorphic site and wherein one oligonucleotide analogue comprises a "C"-nucleobase at the polymorphic site and the other oligonucleotide analogue comprises an "A"-nucleobase at the polymorphic site.

* * * * *

SEQUENCE LISTING

```
<160> NUMBER OF SEQ ID NOS: 40

<210> SEQ ID NO 1
<211> LENGTH: 18
<212> TYPE: DNA
<213> ORGANISM: Artificial sequence
<220> FEATURE:
<223> OTHER INFORMATION: Synthetic

<400> SEQUENCE: 1
aaaaatcccg cgaactcc                                              18

<210> SEQ ID NO 2
<211> LENGTH: 20
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Hydrophobic nucleotide
<220> FEATURE:
<221> NAME/KEY: misc_feature
<222> LOCATION: (6)..(6)
<223> OTHER INFORMATION: Hydrophobic nucleotide
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
```

```
<222> LOCATION: (17)..(17)
<223> OTHER INFORMATION: Hydrophobic nucleotide

<400> SEQUENCE: 2
anaaanatcc cgncganact                                               20

<210> SEQ ID NO 3
<211> LENGTH: 17
<212> TYPE: DNA
<213> ORGANISM: Artificial sequence
<220> FEATURE:
<223> OTHER INFORMATION: Synthetic
<220> FEATURE:
<221> NAME/KEY: misc_featUre
<222> LOCATION: (2)..(2)
<223> OTHER INFORMATION: HydrophobiC nucleotide
<220> FEATURE:
<221> NAME/KEY: misc_featUre
<222> LOCATION: (6)..(6)
<223> OTHER INFORMATION: Hydrophobic nucleotide
<220> FEATURE:
<221> NAME/KEY: misc_feature
<222> LOCATION: (11)..(11)
<223> OTHER INFORMATION: Hydrophobic nucleotide
<220> FEATURE:
<221> NAME/KEY: misc_feature
<222> LOCATION: (16)..(16)
<223> OTHER INFORMATION: Hydrophobic nucleotide

<400> SEQUENCE: 3
tnaggngcgt nttttnt                                                  17

<210> SEQ ID NO 4
<211> LENGTH: 19
<212> TYPE: DNA
<213> ORGANISM: Artificial sequence
<220> FEATURE:
<223> OTHER INFORMATION: Synthetic

<400> SEQUENCE: 4
attttagggc gttttttg                                                 19

<210> SEQ ID NO 5
<211> LENGTH: 25
<212> TYPE: DNA
<213> ORGANISM: Artificial sequence
<220> FEATURE:
<223> OTHER INFORMATION: Synthetic

<400> SEQUENCE: 5
ccgcaaaaaa acgccctaaa atccc                                         25

<210> SEQ ID NO 6
<211> LENGTH: 25
<212> TYPE: DNA
<213> ORGANISM: Artificial sequence
<220> FEATURE:
<223> OTHER INFORMATION: Synthetic

<400> SEQUENCE: 6
ccgcaaaaaa acaccctaaa atccc                                         25

<210> SEQ ID NO 7
<211> LENGTH: 20
<212> TYPE: DNA
<213> ORGANISM: Artificial sequence
<220> FEATURE:
<223> OTHER INFORMATION: Synthetic
<220> FEATURE:
<221> NAME/KEY: misc_feature
```

```
<222> LOCATION: (2)..(2)
<223> OTHER INFORMATION: Hydrophobic nucleotide
<220> FEATURE:
<221> NAME/KEY: misc_feature
<222> LOCATION: (6)..(6)
<223> OTHER INFORMATION: Hydrophobic nucleotide
<220> FEATURE:
<221> NAME/KEY: misc_feature
<222> LOCATION: (13)..13)
<223> OTHER INFORMATION: Hydrophobic nucleotide
<220> FEATURE:
<221> NAME/KEY: misc_feature
<222> LOCATION: (17)..(17)
<223> OTHER INFORMATION: Hydrophobic nucleotide

<400> SEQUENCE: 7
anaaanatcc cgncganact                                               20

<210> SEQ ID NO 8
<211> LENGTH: 16
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Hydrophobic nucleotide
<220> FEATURE:
<221> NAME/KEY: misc_feature
<222> LOCATION: (10)..(10)
<223> OTHER INFORMATION: Hydrophobic nucleotide
<220> FEATURE:
<221> NAME/KEY: misc_feature
<222> LOCATION: (15)..(15)
<223> OTHER INFORMATION: Hydrophobic nucleotide

<400> SEQUENCE: 8
ttngaatcgn gtttnt                                                   16

<210> SEQ ID NO 9
<211> LENGTH: 22
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 9
ttnaaaaacn caattcnaat na                                            22

<210> SEQ ID NO 10
<211> LENGTH: 28
<212> TYPE: DNA
<213> ORGANISM: Artificial sequence
<220> FEATURE:
<223> OTHER INFORMATION: Synthetic
<220> FEATURE:
<221> NAME/KEY: misc_feature
```

```
<222> LOCATION: (1)..(1)
<223> OTHER INFORMATION: Hydrophobic nucleotide

<400> SEQUENCE: 10
ntttgtttag aggttaaagt taattttt                                          28

<210> SEQ ID NO 11
<211> LENGTH: 30
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Hydrophobic nucleotide

<400> SEQUENCE: 11
ntcaaaaaat aattcatact ctataattac                                        30

<210> SEQ ID NO 12
<211> LENGTH: 22
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Hydrophobic nucleotide
<220> FEATURE:
<221> NAME/KEY: misc_featUre
<222> LOCATION: (10)..(10)
<223> OTHER INFORMATION: Hydrophobic nucleotide
<220> FEATURE:
<221> NAME/KEY: misc_feature
<222> LOCATION: (17)..(17)
<223> OTHER INFORMATION: Hydrophobic nucleotide
<220> FEATURE:
<221> NAME/KEY: misc_featUre
<222> LOCATION: (21)..(21)
<223> OTHER INFORMATION: Hydrophobic nucleotide

<400> SEQUENCE: 12
ttnaaaaacn caattcnaat na                                                22

<210> SEQ ID NO 13
<211> LENGTH: 16
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Hydrophobic nucleotide
<220> FEATURE:
<221> NAME/KEY: misc_featUre
<222> LOCATION: (10) (10)
<223> OTHER INFORMATION: Hydrophobic nucleotide
<220> FEATURE:
<221> NAME/KEY: misc_feature
<222> LOCATION: (15)..(15)
<223> OTHER INFORMATION: Hydrophobic nucleotide

<400> SEQUENCE: 13
ttngaatcgn gtttnt                                                       16

<210> SEQ ID NO 14
<211> LENGTH: 22
<212> TYPE: DNA
<213> ORGANISM: Artificial sequence
```

```
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Hydrophobic nucleotide

<400> SEQUENCE: 14
ngggagttag tagggaggta gt                                               22

<210> SEQ ID NO 15
<211> LENGTH: 27
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Hydrophobic nucleotide

<400> SEQUENCE: 15
ntaaaaaatc acrtactttt attaacc                                          27

<210> SEQ ID NO 16
<211> LENGTH: 18
<212> TYPE: DNA
<213> ORGANISM: Artificial sequence
<220> FEATURE:
<223> OTHER INFORMATION: Synthetic

<400> SEQUENCE: 16
tcccacatcc tgctcaag                                                    18

<210> SEQ ID NO 17
<211> LENGTH: 19
<212> TYPE: DNA
<213> ORGANISM: Artificial sequence
<220> FEATURE:
<223> OTHER INFORMATION: Synthetic

<400> SEQUENCE: 17
atctctgcca tcatttccg                                                   19

<210> SEQ ID NO 18
<211> LENGTH: 20
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Hydrophobic nucleotide
<220> FEATURE:
<221> NAME/KEY: misc_feature
<222> LOCATION: (7)..(7)
<223> OTHER INFORMATION: Hydrophobic nucleotide
<220> FEATURE:
<221> NAME/KEY: misc_feature
<222> LOCATION: (13)..(13)
<223> OTHER INFORMATION: Hydrophobic nucleotide
<220> FEATURE:
<221> NAME/KEY: misc_feature
<222> LOCATION: (18)..(18)
<223> OTHER INFORMATION: Hydrophobic nucleotide

<400> SEQUENCE: 18
tncaaanagt ganactgnat                                                  20
```

```
<210> SEQ ID NO 19
<211> LENGTH: 20
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Hydrophobic nucleotide
<220> FEATURE:
<221> NAME/KEY: misc_feature
<222> LOCATION: (7)..(7)
<223> OTHER INFORMATION: Hydrophobic nucleotide
<220> FEATURE:
<221> NAME/KEY: misc_feature
<222> LOCATION: (13)..(13)
<223> OTHER INFORMATION: Hydrophobic nucleotide
<220> FEATURE:
<221> NAME/KEY: misc_feature
<222> LOCATION: (18)..(18)
<223> OTHER INFORMATION: Hydrophobic nucleotide

<400> SEQUENCE: 19
ntcaaanagc ganactgnat                                                   20

<210> SEQ ID NO 20
<211> LENGTH: 17
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Hydrophobic nucleotide
<220> FEATURE:
<221> NAME/KEY: misc_feature
<222> LOCATION: (17)..(17)
<223> OTHER INFORMATION: Hydrophobic nucleotide

<400> SEQUENCE: 20
naccgaccca gcgcccn                                                      17

<210> SEQ ID NO 21
<211> LENGTH: 17
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Hydrophobic nucleotide
<220> FEATURE:
<221> NAME/KEY: misc_feature
<222> LOCATION: (16)..(16)
<223> OTHER INFORMATION: n is a, c, g, or t

<400> SEQUENCE: 21
anccgaccca gcgccnc                                                      17

<210> SEQ ID NO 22
<211> LENGTH: 17
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Hydrophobic nucleotide
<220> FEATURE:
<221> NAME/KEY: misc_feature
```

<222> LOCATION: (15)..(15)
<223> OTHER INFORMATION: Hydrophobic nucleotide

<400> SEQUENCE: 22
acncgaccca gcgcncc                                              17

<210> SEQ ID NO 23
<211> LENGTH: 24
<212> TYPE: DNA
<213> ORGANISM: Artificial sequence
<220> FEATURE:
<223> OTHER INFORMATION: Synthetic

<400> SEQUENCE: 23
cggttacgat gcgcccatct acac                                      24

<210> SEQ ID NO 24
<211> LENGTH: 20
<212> TYPE: DNA
<213> ORGANISM: Artificial sequence
<220> FEATURE:
<223> OTHER INFORMATION: Synthetic

<400> SEQUENCE: 24
cagcaccatc accgcgaggc                                           20

<210> SEQ ID NO 25
<211> LENGTH: 17
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Hydrophobic nucleotide
<220> FEATURE:
<221> NAME/KEY: misc_feature
<222> LOCATION: (16)..(16)
<223> OTHER INFORMATION: Hydrophobic nucleotide

<400> SEQUENCE: 25
anccgaccca gcgccnc                                              17

<210> SEQ ID NO 26
<211> LENGTH: 17
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Hydrophobic nucleotide
<220> FEATURE:
<221> NAME/KEY: misc_feature
<222> LOCATION: (15)..(15)
<223> OTHER INFORMATION: HydrophobiC nucleotide

<400> SEQUENCE: 26
acncgaccca gcgcncc                                              17

<210> SEQ ID NO 27
<211> LENGTH: 17
<212> TYPE: DNA
<213> ORGANISM: Artificial sequence
<220> FEATURE:
<223> OTHER INFORMATION: Synthetic
<220> FEATURE:
<221> NAME/KEY: misc_feature

```
<222> LOCATION: (5)..(5)
<223> OTHER INFORMATION: Hydrophobic nucleotide
<220> FEATURE:
<221> NAME/KEY: misc_feature
<222> LOCATION: (13) (13)
<223> OTHER INFORMATION: Hydrophobic nucleotide

<400> SEQUENCE: 27
accgnaccca gcngccc                                                17

<210> SEQ ID NO 28
<211> LENGTH: 15
<212> TYPE: DNA
<213> ORGANISM: Artificial sequence
<220> FEATURE:
<223> OTHER INFORMATION: Synthetic

<400> SEQUENCE: 28
accgacccag cgccc                                                  15

<210> SEQ ID NO 29
<211> LENGTH: 17
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Hydrophobic nucleotide
<220> FEATURE:
<221> NAME/KEY: misc_feature
<222> LOCATION: (17)..(17)
<223> OTHER INFORMATION: Hydrophobic nucleotide

<400> SEQUENCE: 29
naccgaccca gcgcccn                                                17

<210> SEQ ID NO 30
<211> LENGTH: 17
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Hydrophobic nucleotide
<220> FEATURE:
<221> NAME/KEY: misc_feature
<222> LOCATION: (13)..(13)
<223> OTHER INFORMATION: Hydrophobic nucleotide

<400> SEQUENCE: 30
accgnaccca gcngccc                                                17

<210> SEQ ID NO 31
<211> LENGTH: 15
<212> TYPE: DNA
<213> ORGANISM: Artificial sequence
<220> FEATURE:
<223> OTHER INFORMATION: Synthetic

<400> SEQUENCE: 31
accgacccag cgccc                                                  15

<210> SEQ ID NO 32
<211> LENGTH: 17
<212> TYPE: DNA
<213> ORGANISM: Artificial sequence
```

```
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Hydrophobic nucleotide
<220> FEATURE:
<221> NAME/KEY: misc_feature
<222> LOCATION: (17)..(17)
<223> OTHER INFORMATION: Hydrophobic nucleotide

<400> SEQUENCE: 32
naccgaccca gcgcccn                                                  17

<210> SEQ ID NO 33
<211> LENGTH: 17
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Hydrophobic nucleotide
<220> FEATURE:
<221> NAME/KEY: misc_feature
<222> LOCATION: (16)..(16)
<223> OTHER INFORMATION: Hydrophobic nucleotide

<400> SEQUENCE: 33
anccgaccca gcgccnc                                                  17

<210> SEQ ID NO 34
<211> LENGTH: 17
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Hydrophobic nucleotide
<220> FEATURE:
<221> NAME/KEY: misc_feature
<222> LOCATION: (13)..(13)
<223> OTHER INFORMATION: Hydrophobic nucleotide

<400> SEQUENCE: 34
accgnaccca gcngccc                                                  17

<210> SEQ ID NO 35
<211> LENGTH: 17
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Hydrophobic nucleotide
<220> FEATURE:
<221> NAME/KEY: misc_feature
<222> LOCATION: (12)..(12)
<223> OTHER INFORMATION: Hydrophobic nucleotide

<400> SEQUENCE: 35
accgnaccca gncgccc                                                  17

<210> SEQ ID NO 36
<211> LENGTH: 17
<212> TYPE: DNA
<213> ORGANISM: Artificial sequence
```

```
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Hydrophobic nucleotide
<220> FEATURE:
<221> NAME/KEY: misc_feature
<222> LOCATION: (11)..(11)
<223> OTHER INFORMATION: Hydrophobic nucleotide

<400> SEQUENCE: 36
accgacncca ngcgccc                                              17

<210> SEQ ID NO 37
<211> LENGTH: 15
<212> TYPE: DNA
<213> ORGANISM: Artificial sequence
<220> FEATURE:
<223> OTHER INFORMATION: Synthetic

<400> SEQUENCE: 37
accgacccag cgccc                                                15

<210> SEQ ID NO 38
<211> LENGTH: 21
<212> TYPE: DNA
<213> ORGANISM: Artificial sequence
<220> FEATURE:
<223> OTHER INFORMATION: Synthetic

<400> SEQUENCE: 38
aacgggcgct gggtcggtta c                                         21

<210> SEQ ID NO 39
<211> LENGTH: 24
<212> TYPE: DNA
<213> ORGANISM: Artificial sequence
<220> FEATURE:
<223> OTHER INFORMATION: Synthetic

<400> SEQUENCE: 39
gcgggagttc gcgggatttt ttag                                      24

<210> SEQ ID NO 40
<211> LENGTH: 24
<212> TYPE: DNA
<213> ORGANISM: Artificial sequence
<220> FEATURE:
<223> OTHER INFORMATION: Synthetic

<400> SEQUENCE: 40
gtgggagttt gtgggatttt ttag                                      24
```